(12) United States Patent
Miller et al.

(10) Patent No.: US 11,661,476 B2
(45) Date of Patent: May 30, 2023

(54) METHODS AND COMPOSITIONS FOR BIORENEWABLE POLYESTERS DERIVED FROM CAMPHORIC ACID

(71) Applicant: University of Florida Research Foundation, Inc., Gainesville, FL (US)

(72) Inventors: Stephen A. Miller, Gainesville, FL (US); Olivier Nsengiyumva, Washington, DC (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 17 days.

(21) Appl. No.: 17/414,173

(22) PCT Filed: Feb. 14, 2020

(86) PCT No.: PCT/US2020/018266
§ 371 (c)(1),
(2) Date: Jun. 15, 2021

(87) PCT Pub. No.: WO2020/168177
PCT Pub. Date: Aug. 20, 2020

(65) Prior Publication Data
US 2022/0033574 A1  Feb. 3, 2022

Related U.S. Application Data

(60) Provisional application No. 62/953,695, filed on Dec. 26, 2019, provisional application No. 62/805,875, filed on Feb. 14, 2019.

(51) Int. Cl.
*C08G 63/199* (2006.01)
*C07C 67/08* (2006.01)
*C07D 307/20* (2006.01)

(52) U.S. Cl.
CPC ............ *C08G 63/199* (2013.01); *C07C 67/08* (2013.01); *C07D 307/20* (2013.01); *C08G 2230/00* (2013.01)

(58) Field of Classification Search
CPC .. C07C 67/08; C07D 307/20; C08G 2230/00; C08G 63/199; C08G 63/183; C08G 63/66
See application file for complete search history.

(56) References Cited

U.S. PATENT DOCUMENTS

| | | | | |
|---|---|---|---|---|
| 3,644,295 A * | 2/1972 | Price et al. | ............... | C08K 5/42 8/588 |
| 5,093,025 A * | 3/1992 | Koide | ................ | C09K 19/3809 528/274 |
| 6,180,025 B1 * | 1/2001 | Schoenfeld | ............ | C09D 5/032 252/299.01 |
| 2012/0276477 A1 * | 11/2012 | Wosnick | ............ | G03G 9/08755 430/109.4 |
| 2012/0276478 A1 * | 11/2012 | Wosnick | ............ | G03G 9/08755 430/109.4 |
| 2016/0370723 A1 * | 12/2016 | Ozawa | ................ | C08G 63/672 |
| 2019/0002630 A1 | 1/2019 | Nguyen et al. | | |
| 2019/0023839 A1 | 1/2019 | Miller et al. | | |
| 2022/0033574 A1 * | 2/2022 | Miller | .................... | C08G 63/66 |

FOREIGN PATENT DOCUMENTS

DE  1720821  *  7/1971

OTHER PUBLICATIONS

Th. Rieckmann et al "Poly(Ethylene Terephthalate) Polymerization—Mechanism, Catalysis, Kinetics, Mass Transfer and Reactor Design", Chapter II, Modern Polyesters: Chemistry and Technology of Polyesters and Copolyesters. Edited by J. Scheirs and T. E. Long, 2003 John Wiley & Sons, Ltd (Year: 2003).*
Chengcai Pang et al "Copolymerization of Natural Camphor-Derived Rigid Diol with Various Dicarboxylic Acids: Access to Biobased Polyesters with Various Properties", ACS Macro Lett. 2019, 8, 1442-1448 (Year: 2019).*
Olivier Nsengiyumva et al. "Synthesis, characterization, and water-degradation of biorenewable polyesters derived from natural camphoric acid", Green Chem., 2019, 21, 973 (Year: 2019).*
Ramesh M. Gohil "Properties and Strain Hardening Character of Polyethylene Terephthalate Containing Isosorbide", Polymer Engineering and Science—2009 (Year: 2009).*
Chaima Bouyahya et al "Isosorbide and 2,5-Furandicarboxylic Acid Based (Co)Polyesters: Synthesis, Characterization, and Environmental Degradation", Polymers 2022, 14, 3868 (Year: 2022).*
International Search Report and Written Opinion for PCT/US2020/018266 dated Jun. 24, 2020.
Pubchem, Compound Summary for SID 272740524, Available Date:Dec. 11, 2015 [retrieved on Apr. 1, 2020]. Retrieved from the Internet: <URL: https://pubchem.ncbi.nlm.nih.gov/substance/272740524> entire document.

(Continued)

*Primary Examiner* — Frances Tischler
*Assistant Examiner* — Gennadiy Mesh
(74) *Attorney, Agent, or Firm* — Thomas|Horstemeyer, LLP

(57) ABSTRACT

In one aspect, the disclosure relates to biorenewable polyesters and polyester copolymers derived from camphoric acid, methods of making same, and articles comprising same. The disclosed biorenewable polyesters can have a Mn of from about 5,000 Da to about 500,000 Da. Also disclosed herein is the preparation of various monomers useful in the reactions disclosed herein, e.g., cis-1,4-anhydroerythritol and bis(2-hydroxyethyl) camphorate. In various aspects, the disclosed biorenewable polyesters and polyester copolymers can be used to the production of various articles utilizing a conventional polyester or polyester copolymer, that is, to replace, in part or in whole, a conventional nonbiorenewable polyester or polyester copolymer. This abstract is intended as a scanning tool for purposes of searching in the particular art and is not intended to be limiting of the present disclosure.

2 Claims, 79 Drawing Sheets

(56) References Cited

OTHER PUBLICATIONS

Nsengiyumva et al., Synthesis, characterization, and water-degradation of biorenewable polyesters derived from natural camphoric acid, Green Chemistry, vol. 21, Iss. 5, Feb. 14, 2019 [retrieved on May 11, 2020]. Retrieved from the Internet: <URL: https://pubs.rsc.org/en/content/articlelanding/2019/GC/CBGC03990A>, abstract.

* cited by examiner

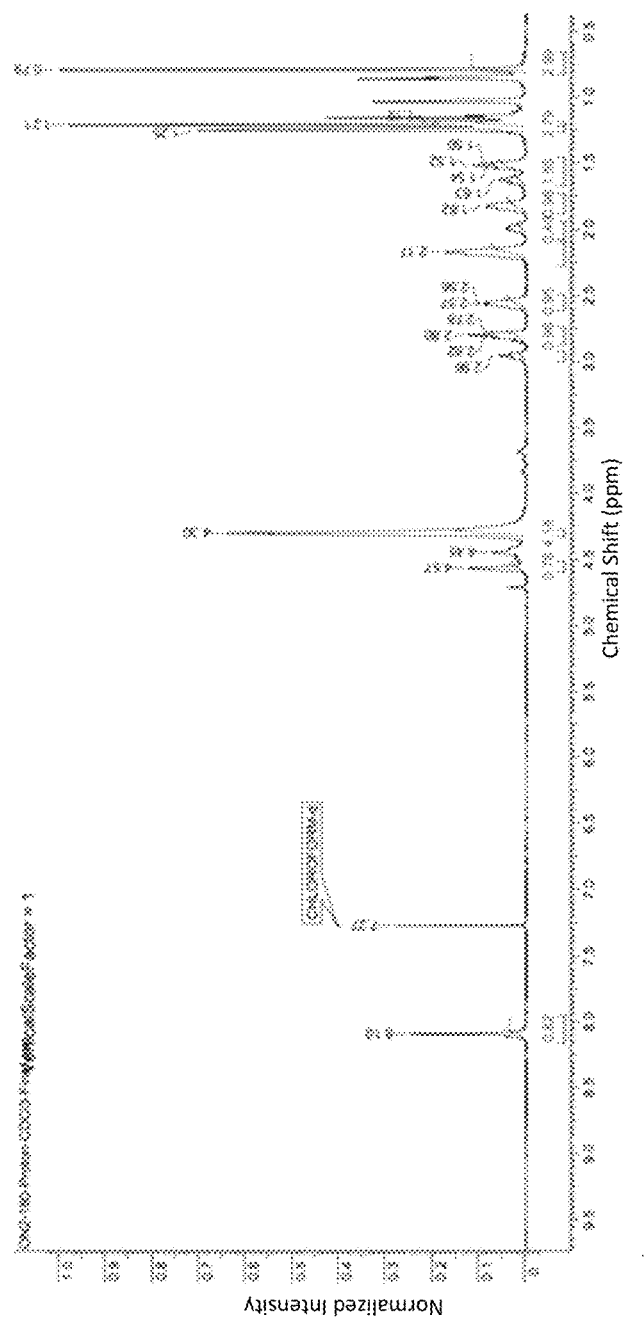

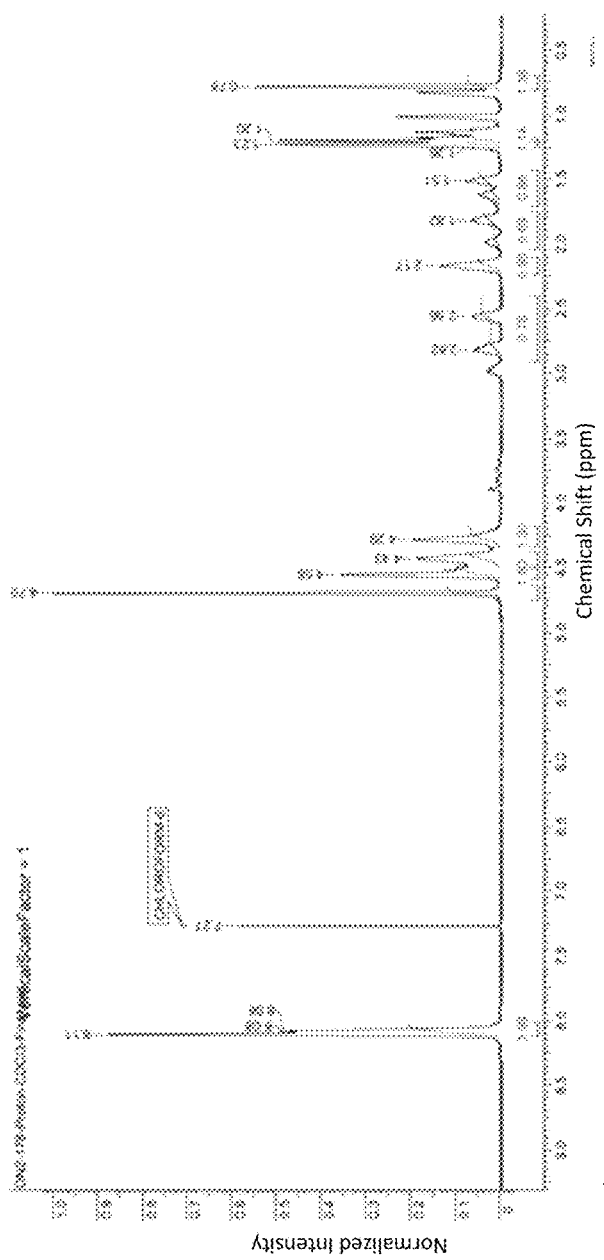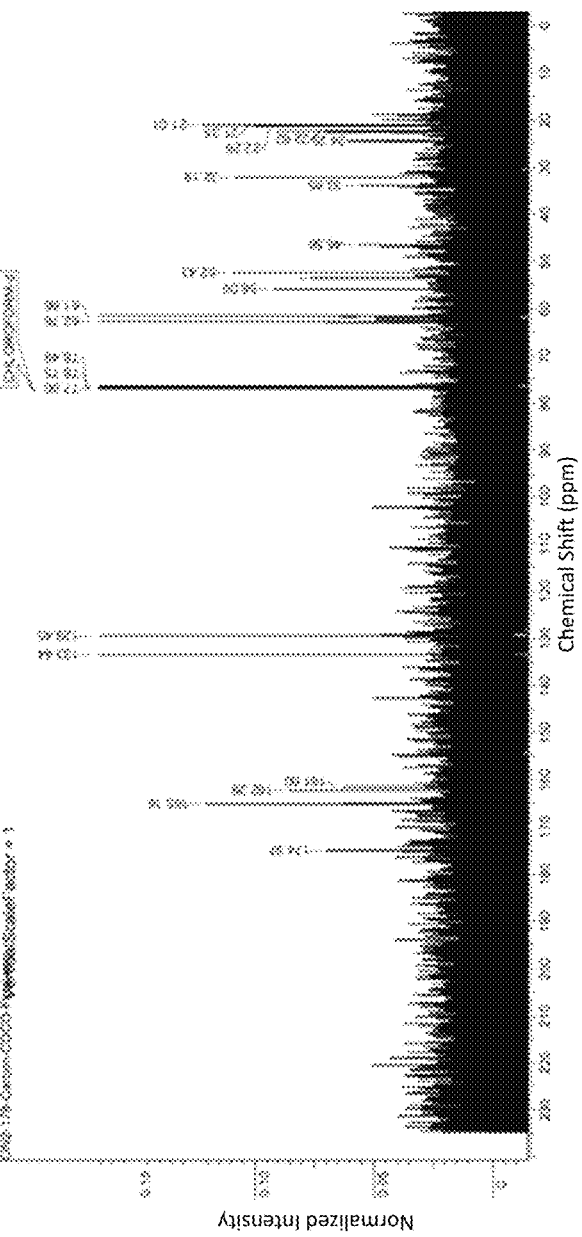

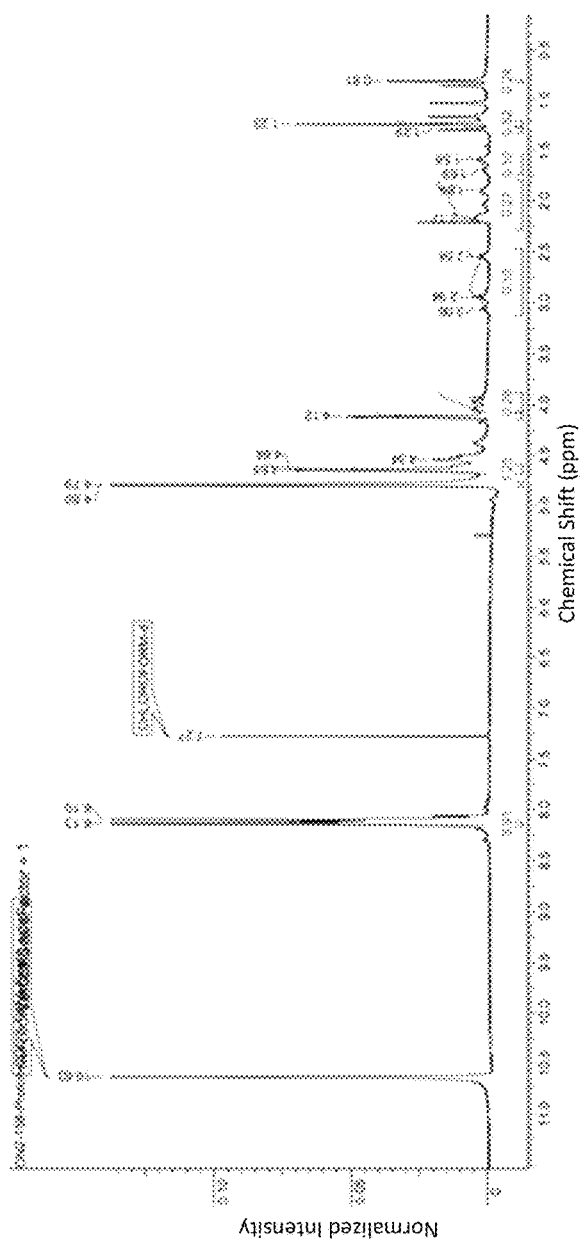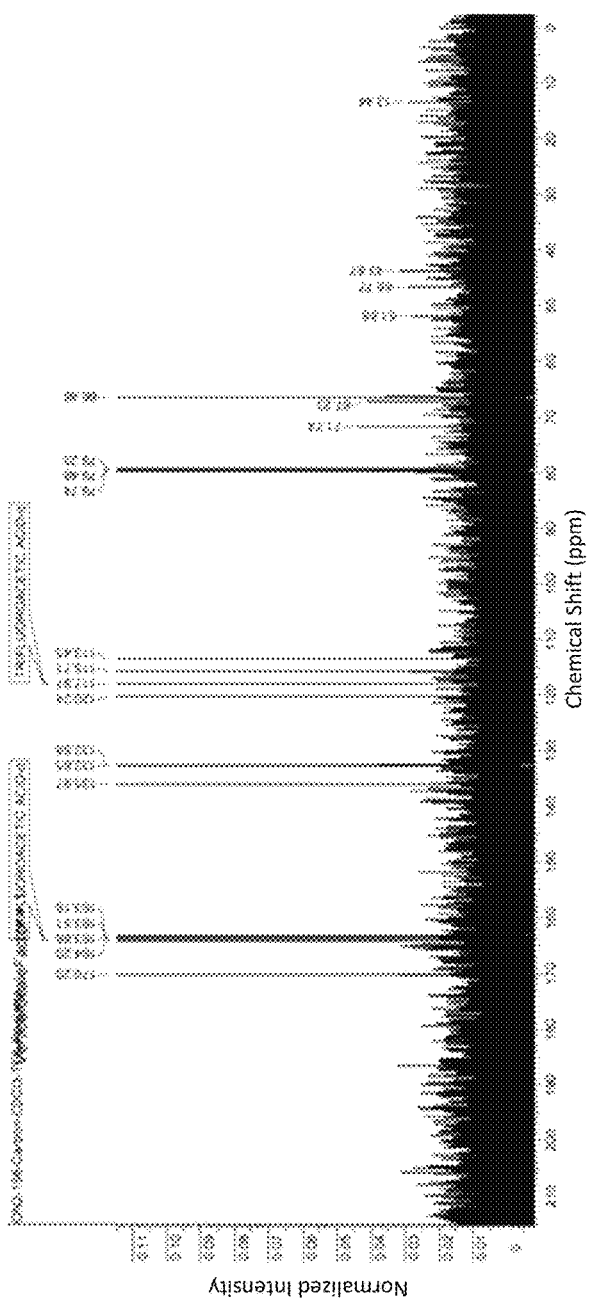

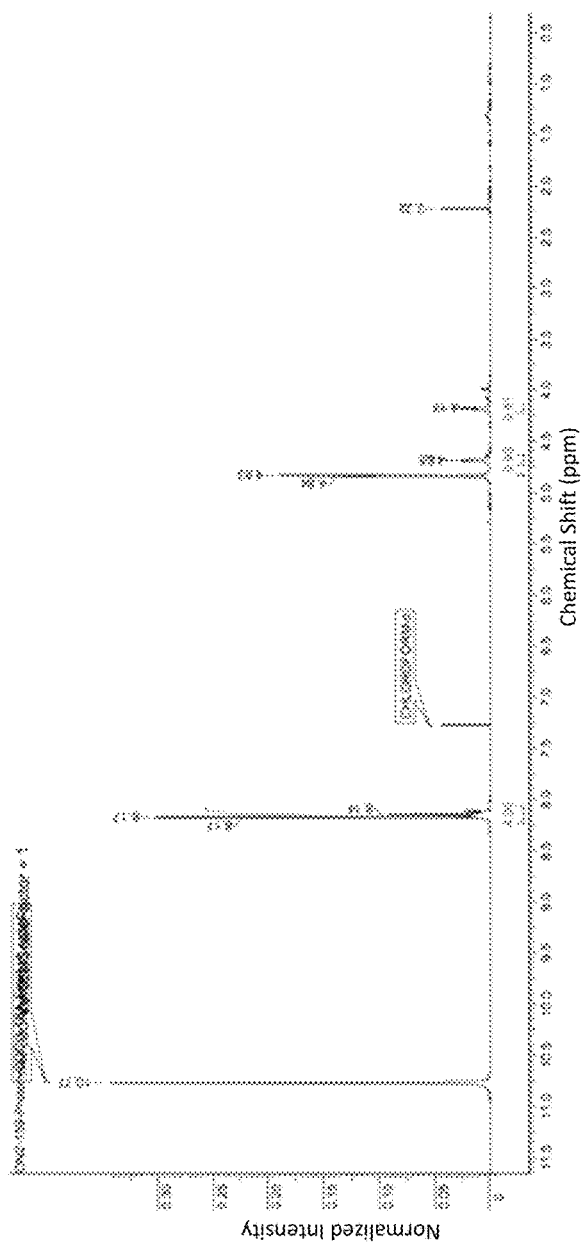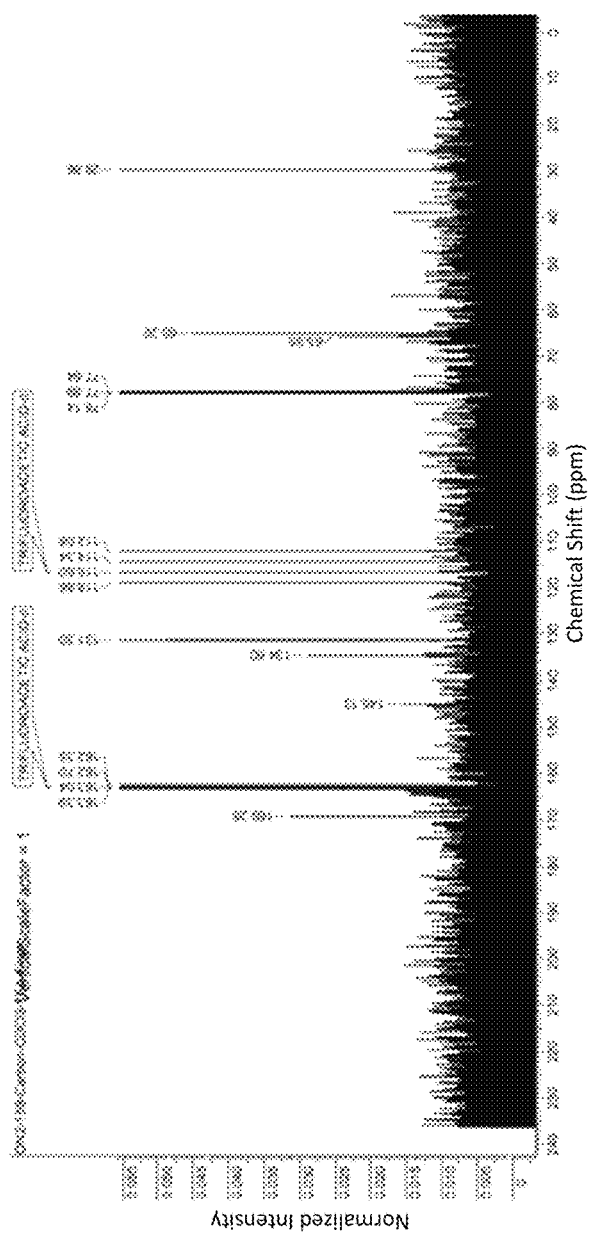

METHODS AND COMPOSITIONS FOR BIORENEWABLE POLYESTERS DERIVED FROM CAMPHORIC ACID

CROSS-REFERENCE TO RELATED APPLICATIONS

This application claims the benefit of U.S. Provisional Application Nos. 62/805,875 and 62/953,695, respectively filed on Feb. 14, 2019 and Dec. 26, 2019, each of which is incorporated herein by reference in its entirety.

STATEMENT REGARDING FEDERALLY SPONSORED RESEARCH OR DEVELOPMENT

This application is the 35 U.S.C. § 371 national stage of PCT application having serial number PCT/US2020/018266, filed on Feb. 14, 2020. This application also claims priority to U.S. provisional application Nos. 62/805,875 and 62/953,695, respectively filed on Feb. 14, 2019 and Dec. 26, 2019, each of which is incorporated herein by reference in its entirety.

BACKGROUND

Over the last 100 years, the commercial plastics industry has enjoyed fantastic growth via a somewhat small array of fossil fuel monomers. Many polymers have been commercialized and the success of these high volume materials can be attributed to a great balance of low production cost and good thermal and mechanical properties (Refs. 1, 2). However, their increased production and usage is accompanied by a plethora of negative environmental impacts—notably, low recycling rates and poor environmental degradation behavior (Refs. 3, 4). Additionally, the fossil fuel resources for these commercial polymers are dwindling (Refs. 5-7). This depletion of resources and the steady increase in demand for materials herald the need for sustainable polymers.

To confront these problems, many researchers have designed and synthesized novel polymers with a variety of functional groups derived from renewable resources (Refs. 10-15). Polyesters are particularly attractive because they are potentially both renewable and degradable. The ester functionality is prone to water-degradation (hydrolysis) or biodegradation and it has been of great interest during the past few decades (Refs. 16-18). Polylactic acid (PLA), arguably the most successful, is a fully biorenewable polyester, made from corn starch or other carbohydrates (FIG. 1). However, it still suffers from a low glass transition temperature ($T_g$) of 55° C. and it usually does not degrade apart from industrial composting conditions (Refs. 19-21). In pursuit of improved biorenewable polyesters, there are reports of utilization of abundantly available biobased monomers such as ferulic acid (Refs. 22-24) or itaconic acid (Ref. 25) striving to mimic the thermal properties of extant commercial polymers such as PLA or polyethylene terephthalate (PET; FIG. 1).

A biobased monomer that of potential use is camphoric acid (FIG. 1). Oxidation of the bicyclic terpene (1R)-(+)-camphor affords (1R,3S)-(+)-camphoric acid which, importantly, retains a conformationally rigid five-membered ring. Previous work has demonstrated the importance of main-chain cyclics (Ref. 26) or aromatics (Refs. 22,23) for conferring high $T_g$ values. Natural (+)-camphor itself can be obtained via the distillation of wood from the camphor laurel tree (*Cinnamomum camphora*) found in Borneo, Taiwan, and East Africa, but also naturalized in many other parts of the world including North America (Refs. 27-28). Among all commercial aroma chemicals, camphor is one of the most widespread, garnering 100+ million US dollars in annual sales. Its commercial popularity led to the common industrial production process (near 17,000 tons per year, see Ref. 29) via the readily available monoterpene α-pinene, found in the turpentine oil of wood pulp (Refs. 30-34). The commodity price of camphor is approximately $3.00 per kg (Ref. 35).

In organic synthesis, camphor-derived compounds have been extensively used as chiral templates in enantioselective synthesis, among other specific applications (Refs. 41-48). Yet, minimal work has been reported demonstrating the polymerization of camphor-derived monomers (Refs. 36-40). Because of its bioavailability and potential for scalability, camphor is an ideal building block for constructing novel polymers.

Despite advances in research directed to polyesters prepared from biobased monomers, there is still a scarcity of polyesters utilizing biobased camphoric acid monomers. These needs and other needs are satisfied by the present disclosure.

SUMMARY

In accordance with the purpose(s) of the present disclosure, as embodied and broadly described herein, the disclosure, in one aspect, relates to polyesters derived from natural camphoric acid, methods of making same, and articles comprising same.

Disclosed are polyester polymers having a structure represented by a formula:

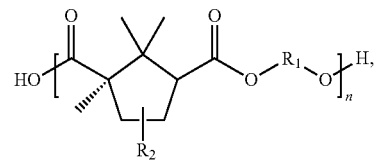

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; and wherein n is a value such that the Mn has a value from about 5,000 Da to about 500,000 Da. In some aspects, $R_2$ is hydrogen.

Disclosed are polyester polymers having a structure represented by a formula:

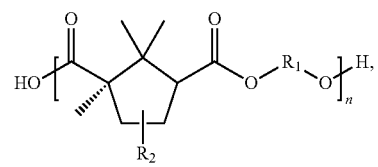

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; and wherein n is a value such that the MW has a value from about 5,000 Da to about 500,000 Da. In some aspects, $R_2$ is hydrogen.

Disclosed are polyester polymers having a structure represented by a formula:

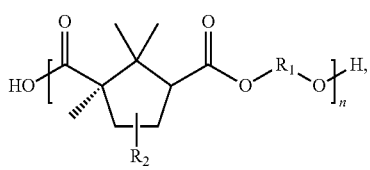

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; and wherein n is a value such that the critical molecular weight (Me) has a value from about 5,000 Da to about 500,000 Da. In some aspects, $R_2$ is hydrogen.

In still other aspects, the polymer is selected from:

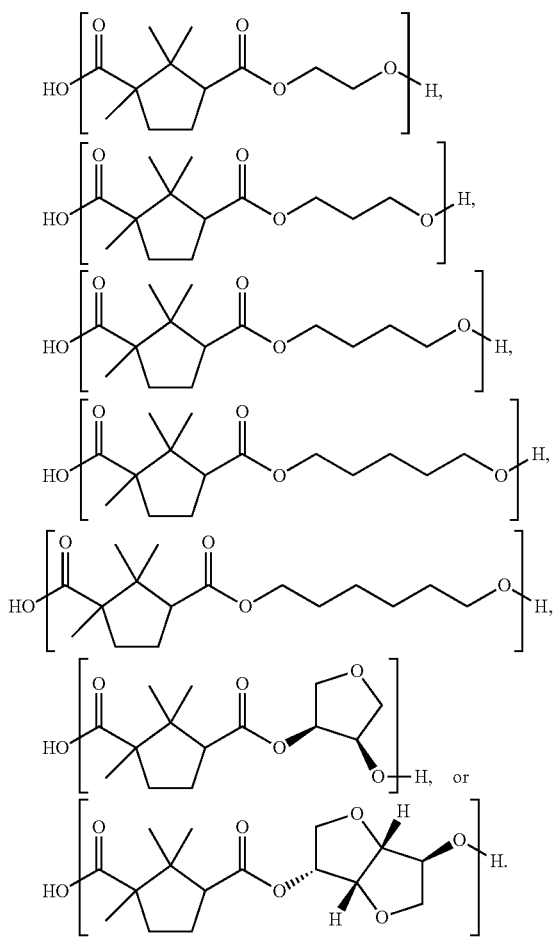

In other aspects, the polymer is selected from:

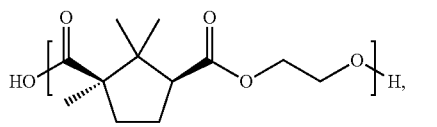

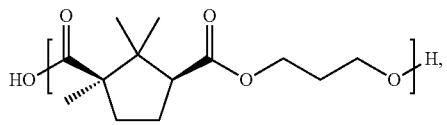

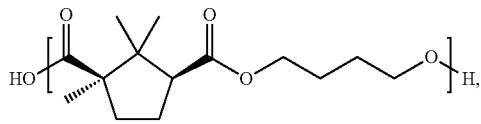

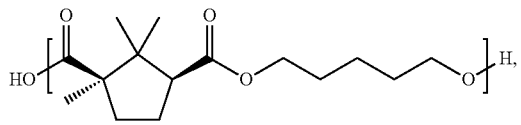

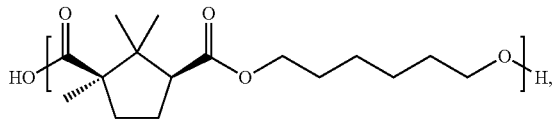

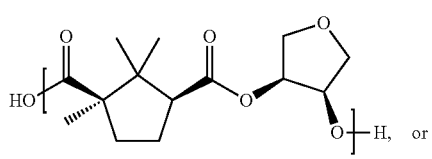

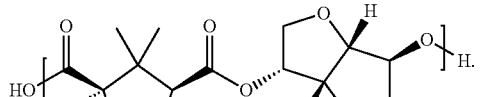

Also disclosed are polyester polymers having a structure represented by a formula:

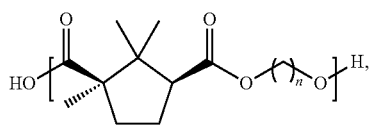

wherein n is an integer from 1-12.

Also disclosed are polyester copolymers having a structure represented by a formula:

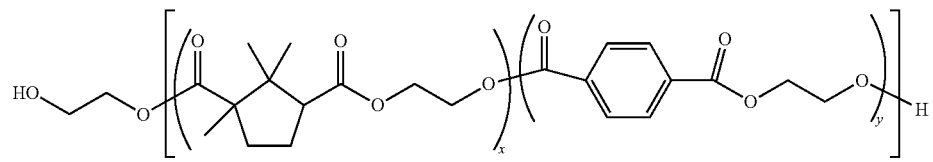

Also disclosed are polyester copolymers having a structure represented by a formula:

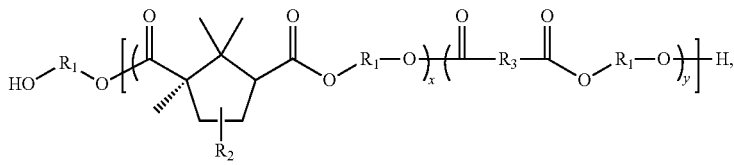

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; wherein $R_3$ is arylene; and wherein x and y are values such that the Mn for the polyester polymer has a value from about 5,000 Da to about 500,000 Da.

Also disclosed are polyester copolymers having a structure represented by a formula:

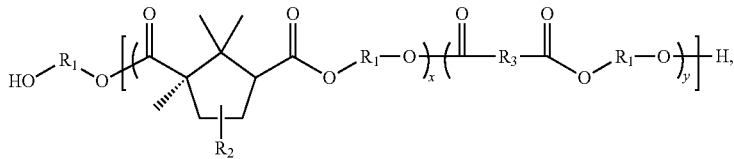

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; wherein $R_3$ is arylene; and wherein x and y are values such that the MW for the polyester polymer has a value from about 5,000 Da to about 500,000 Da.

Also disclosed are polyester copolymers having a structure represented by a formula:

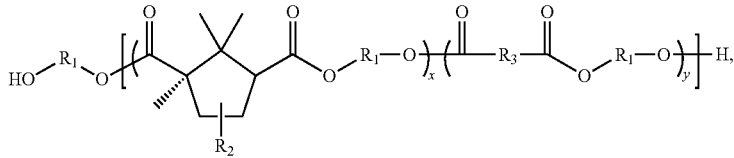

wherein $R_1$ is C1-C12 alkanediyl or C3-C12 cycloalkanediyl; wherein each occurrence of $R_2$ is independently selected from hydrogen, C1-C12 alkanediyl, and C3-C12 cycloalkanediyl; wherein $R_3$ is arylene; and wherein x and y are values such that the critical molecular weight (Me) for the polyester polymer has a value from about 5,000 Da to about 500,000 Da.

Also disclosed are methods of making the disclosed polyester polymers, the method comprising: providing camphoric acid,
providing a diol having a structure represented by a formula:

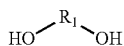

providing a catalyst; and reacting the camphoric acid analogue and the diol in the presence of the catalyst for a suitable period of time at a suitable temperature to provide a polyester of any one of the above aspects; wherein $R_1$ is C1-C12 alkanediyl or C3-C12 cycloalkanediyl; and wherein each occurrence of $R_2$ is independently selected from hydrogen, C1-C12 alkanediyl, and C3-C12 cycloalkanediyl. In some aspects, R, is C2-C8 alkyl or C2-C6 alkyl.

In some aspects, the diol has a structure selected from a formula:

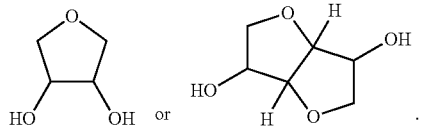 [SMILES: OC1COCC1O ; OC1COC2C(O)COC12]

In some aspects, the diol has a structure selected from a formula:

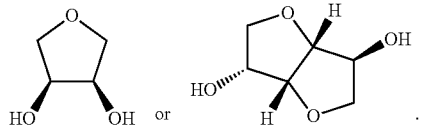 [SMILES: O[C@@H]1COC[C@@H]1O ; O[C@@H]1CO[C@H]2[C@@H]1OC[C@@H]2O]

In other aspects, the diol has a structure selected from a formula: HO—$(CH_2)_2$—OH, HO—$(CH_2)_3$—OH, HO—$(CH_2)_4$—OH, HO—$(CH_2)_5$—OH, HO—$(CH_2)_6$—OH, HO—$(CH_2)_7$—OH, HO—$(CH_2)_8$—OH, HO—$(CH_2)_9$—OH, or HO—$(CH_2)_{10}$—OH.

In any of these aspects, the camphoric acid has a structure represented by a formula:

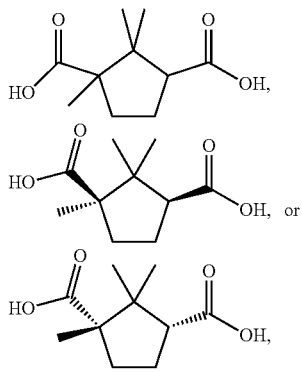

or a mixture thereof.

Also disclosed are articles including or made from the disclosed polyester polymers or polyester copolymers.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 4A shows Scheme 1. The scheme shows that natural (+)-camphor is readily oxidized to camphoric acid, which is then subjected to polymerization with a variety of diols to afford linear polyesters. Various species can catalyze polyesterification. FIG. 4B shows Scheme 2 for the copolymerization of bis(hydroxyethyl) camphorate (BHEC, from camphoric acid) and bis(hydroxyethyl) terephthalate (BHET, from terephthalic acid) as described herein below and in Table 3 (see note "a").

FIG. 5A shows a gel permeation chromatogram (GPC). FIG. 5B shows a differential scanning calorimetry (DSC) thermogram. FIG. 5C shows a thermogravimetric analysis (TGA) thermogram. FIG. 5D shows $^1$H NMR. FIG. 5E shows $^{13}$C NMR.

FIG. 6A shows a gel permeation chromatogram (GPC). FIG. 6B shows a differential scanning calorimetry (DSC) thermogram. FIG. 6C shows a thermogravimetric analysis (TGA) thermogram. FIG. 6D shows $^1$H NMR. FIG. 6E shows $^{13}$C NMR.

FIG. 7A shows a gel permeation chromatogram (GPC). FIG. 7B shows a differential scanning calorimetry (DSC) thermogram. FIG. 7C shows a thermogravimetric analysis (TGA) thermogram. FIG. 7D shows $^1$H NMR. FIG. 7E shows $^{13}$C NMR.

FIG. 8A shows a gel permeation chromatogram (GPC). FIG. 8B shows a differential scanning calorimetry (DSC) thermogram. FIG. 8C shows a thermogravimetric analysis (TGA) thermogram. FIG. 8D shows $^1$H NMR. FIG. 8E shows $^{13}$C NMR.

FIG. 9A shows a gel permeation chromatogram (GPC). FIG. 9B shows a differential scanning calorimetry (DSC) thermogram. FIG. 9C shows a thermogravimetric analysis (TGA) thermogram. FIG. 9D shows $^1$H NMR. FIG. 9E shows $^{13}$C NMR.

FIG. 10A shows a gel permeation chromatogram (GPC). FIG. 10B shows a differential scanning calorimetry (DSC) thermogram. FIG. 10C shows a thermogravimetric analysis (TGA) thermogram. FIG. 10D shows $^1$H NMR. FIG. 10E shows $^{13}$C NMR.

FIG. 11A shows a gel permeation chromatogram (GPC). FIG. 11B shows a differential scanning calorimetry (DSC) thermogram. FIG. 11C shows a thermogravimetric analysis (TGA) thermogram. FIG. 11D shows $^1$H NMR. FIG. 11E shows $^{13}$C NMR.

FIG. 12A shows a gel permeation chromatogram (GPC). FIG. 12B shows a differential scanning calorimetry (DSC) thermogram. FIG. 12C shows a thermogravimetric analysis (TGA) thermogram. FIG. 12D shows $^1$H NMR. FIG. 12E shows $^{13}$C NMR.

FIG. 13A shows a gel permeation chromatogram (GPC). FIG. 13B shows a differential scanning calorimetry (DSC) thermogram. FIG. 13C shows a thermogravimetric analysis (TGA) thermogram. FIG. 13D shows $^1$H NMR. FIG. 13E shows $^{13}$C NMR.

FIGS. 14A-E show characterization of poly(BHEC/BHET) with 90% BHEC (where BHET is bis(2-hydroxyethyl terephthalate). FIG. 14A shows a gel permeation chromatogram (GPC). FIG. 14B shows a differential scanning calorimetry (DSC) thermogram. FIG. 14C shows a thermogravimetric analysis (TGA) thermogram. FIG. 14D shows $^1$H NMR. FIG. 14E shows $^{13}$C NMR.

FIG. 15A shows a gel permeation chromatogram (GPC). FIG. 15B shows a differential scanning calorimetry (DSC) thermogram. FIG. 15C shows a thermogravimetric analysis (TGA) thermogram. FIG. 15D shows $^1$H NMR. FIG. 15E shows $^{13}$C NMR.

FIG. 16A shows a gel permeation chromatogram (GPC). FIG. 16B shows a differential scanning calorimetry (DSC) thermogram. FIG. 16C shows a thermogravimetric analysis (TGA) thermogram. FIG. 16D shows $^1$H NMR. FIG. 16E shows $^{13}$C NMR.

FIG. 17A shows a gel permeation chromatogram (GPC). FIG. 17B shows a differential scanning calorimetry (DSC) thermogram. FIG. 17C shows a thermogravimetric analysis (TGA) thermogram. FIG. 17D shows $^1$H NMR. FIG. 17E shows $^{13}$C NMR.

FIGS. 18A-E show characterization of poly(BHEC/BHET) with 50% BHEC. FIG. 18A shows a gel permeation chromatogram (GPC). FIG. 18B shows a differential scanning calorimetry (DSC) thermogram. FIG. 18C shows a thermogravimetric analysis (TGA) thermogram. FIG. 18D shows $^1$H NMR. FIG. 18E shows $^{13}$C NMR.

FIG. 19A shows a gel permeation chromatogram (GPC). FIG. 19B shows a differential scanning calorimetry (DSC) thermogram. FIG. 19C shows a thermogravimetric analysis (TGA) thermogram. FIG. 19D shows $^1$H NMR. FIG. 19E shows $^{13}$C NMR.

FIG. 20A shows a gel permeation chromatogram (GPC). FIG. 20B shows a differential scanning calorimetry (DSC) thermogram. FIG. 20C shows a thermogravimetric analysis (TGA) thermogram. FIG. 20D shows $^1$H NMR. FIG. 20E shows $^{13}$C NMR.

FIG. 21A shows a gel permeation chromatogram (GPC). FIG. 21B shows a differential scanning calorimetry (DSC) thermogram. FIG. 21C shows a thermogravimetric analysis (TGA) thermogram. FIG. 21D shows $^1$H NMR. FIG. 21E shows $^{13}$C NMR.

FIGS. 22A-E show characterization of poly(BHEC/BHET) with 10% BHEC. FIG. 22A shows a gel permeation chromatogram (GPC). FIG. 22B shows a differential scanning calorimetry (DSC) thermogram. FIG. 22C shows a thermogravimetric analysis (TGA) thermogram. FIG. 22D shows $^1$H NMR. FIG. 22E shows $^{13}$C NMR.

FIGS. 23A-E show characterization of polyBHET. FIG. 23A shows a gel permeation chromatogram (GPC). FIG. 23B shows a differential scanning calorimetry (DSC) thermogram. FIG. 23C shows a thermogravimetric analysis (TGA) thermogram. FIG. 23D shows $^1$H NMR. FIG. 23E shows $^{13}$C NMR.

FIG. 27A shows $^1$H NMR and FIG. 27B shows $^{13}$C NMR.

FIG. 28A shows $^1$H NMR and FIG. 28B shows $^{13}$C NMR.

FIG. 29A shows polymers in vials on an orbital shaker. FIG. 29B shows a polyethylene camphorate sample after one day; significant gelation and/or degradation have not occurred. FIG. 29C shows a polyethylene camphorate sample after 14 days; the polyethylene camphorate at the bottom of the vials shows obvious signs of swelling and or gelation, having assumed a spherical shape.

FIG. 30A shows polyethylene camphorate in aqueous solution with pH=1. The peak mx at 22.79 minutes appears after the lowest molecular weight PMMA standard (22.4 minutes, 600 Da). FIG. 30B shows polyethylene camphorate in aqueous solution with pH=2. The peak max at 2.69 minutes appears after the lowest molecular weight PMMA standard (22.4 minutes, 600 Da).

Figure 1:
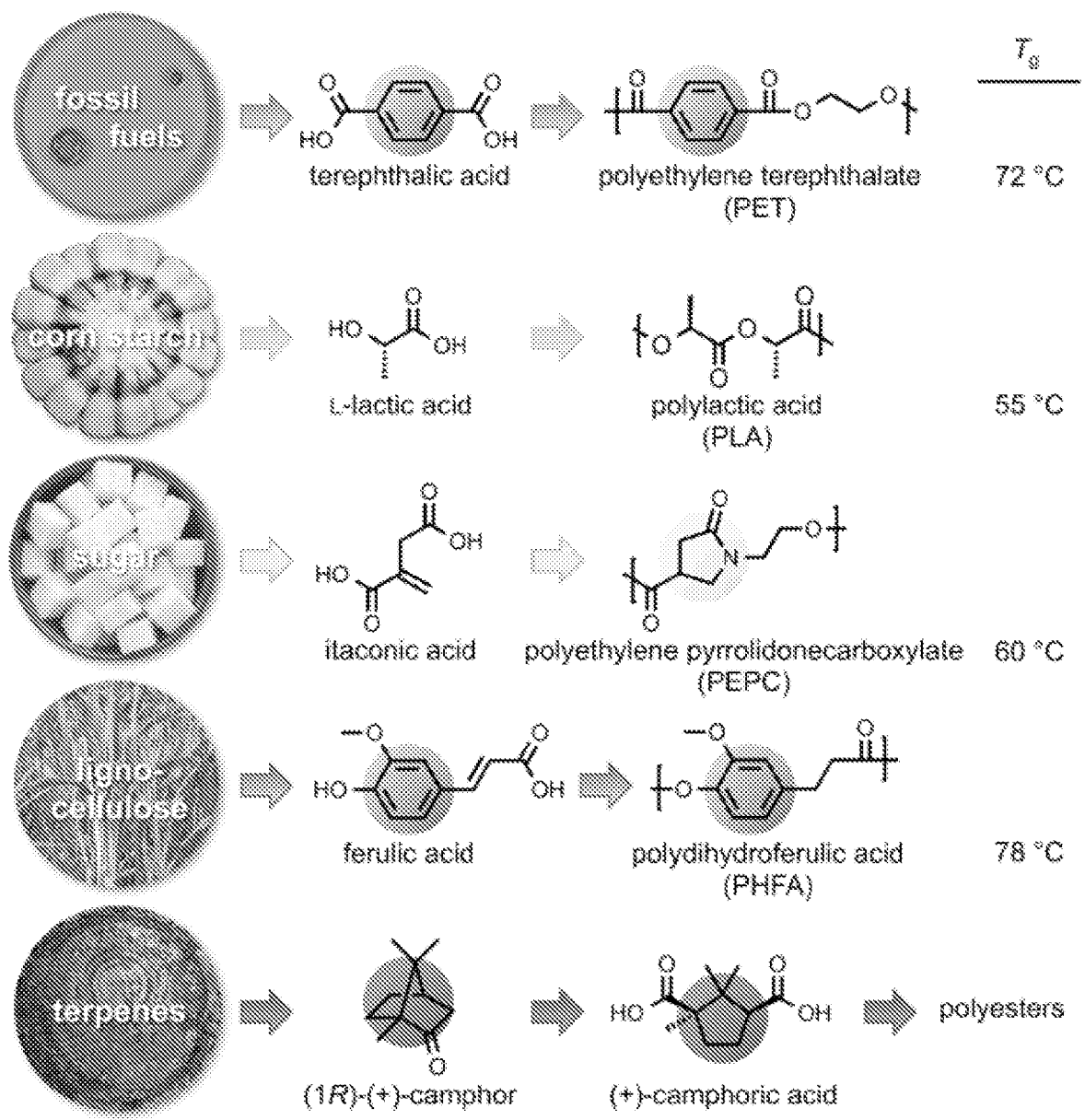
FIG. 1 is representative polyesters. Polyesters exhibit glass transition temperatures ($T_g$) rather dependent on structure, with rings generally conferring higher $T_g$ values. A standing challenge has been to employ inexpensive biobased feedstocks for the synthesis of high $T_g$ polyesters.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, nitrile, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

The term alkanediyl refers to branched or unbranched saturated hydrocarbon group of 1 to 24 carbon atoms bound by two different carbon atoms to the respective substituents. That is, unless particularly stated otherwise, the term alkanediyl as used herein means a divalent atomic group obtained by extracting two hydrogen atoms from a branched or unbranched saturated hydrocarbon group of 1 to 24 carbon atoms. The alkanediyl group can be cyclic or acyclic. The alkanediyl group can be branched or unbranched. The alkyl group can also be substituted or unsubstituted. For example, the alkanediyl group can be substituted with one or more groups including, but not limited to, alkyl, cycloalkyl, alkoxy, amino, nitrile, ether, halide, hydroxy, nitro, silyl, sulfo-oxo, or thiol, as described herein. A "lower alkanediyl" group is an alkanediyl group containing from one to six (e.g., from one to four) carbon atoms. The term alkanediyl group can also be a C1 alkanediyl, C1-C2 alkanediyl, C1-C3 alkanediyl, C1-C4 alkanediyl, C1-C5 alkanediyl, C1-C6 alkanediyl, C1-C7 alkanediyl, C1-C8 alkanediyl, C1-C9 alkanediyl, C1-C10 alkanediyl, and the like up to and including a C1-C24 alkanediyl.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein. In one aspect, the heterocycloalkyl group can be a lactam, including but not limited to an N-substituted lactam.

As used herein, the term, "cycloalkanediyl" refers to a divalent atomic group obtained by extracting two hydrogen atoms from a cycloalkane, i.e., a non-aromatic carbon-based ring composed of at least three carbon atoms. The cycloalkanediyl group can be substituted or unsubstituted. The cycloalkanediyl group can be substituted with one or more groups including, but not limited to, alkyl, cycloalkyl, alkoxy, amino, ether, halide, hydroxy, nitro, silyl, sulfo-oxo, or thiol as known to the skilled artisan.

As used herein, the term, "arylene" refers to divalent aromatic groups having in the range of 3 up to 14 carbon atoms (and optionally one or more heteroatoms such as N, S or O), and "substituted arylene" refers to arylene groups further bearing one or more substituents as set forth above.

As used herein, "weight average molecular weight" or Mw is an average molecular weight that takes the molecular weight of a chain into account when determining contribution to the molecular weight average. Thus, a longer polymer chain will contribute more to Mw than will a shorter polymer chain.

As used herein, "number average molecular weight" or Mn refers to the statistical average molecular weight of all polymer chains in a sample. In one aspect, Mn can be predicted by polymerization mechanism. In another aspect, for a given Mn, equal numbers of molecules exist on either side of Mn in the molecular weight distribution.

As used herein, "dispersity" or "polydispersity index" is a measure of the heterogeneity of sizes of polymers in a composition. Dispersity is represented by the symbol Đ, where Đ=Mw/Mn. Đ will always be greater than or equal to 1, but will be larger for polymer chains with widely varying chain lengths and will be closer to 1 for polymer chains with uniform chain length.

"Glass transition temperature" or $T_g$ is a reversible, gradual transition in an amorphous or semicrystalline material from a brittle, glassy state to a viscous, rubbery state as temperature increases. Some materials can have a melting temperature as well as a $T_g$; if so, $T_g$ is always lower than the melting temperature. In some aspects, the polymers disclosed herein have a $T_g$ but not a melting temperature.

In one aspect, as used herein, "crystalline" refers to a solid material with constituents arranged in an ordered microscopic structure with a crystal lattice extending in all directions. A crystalline material typically has a melting temperature. In some aspects, the polyester polymers and copolymers disclosed herein are not crystalline. In other aspects, some of the polyester polymers and copolymers disclosed herein are crystalline.

Unless otherwise specified, temperatures referred to herein are based on atmospheric pressure (i.e. one atmosphere).

Biorenewable Polyesters Derived from Camphoric Acid

Disclosed herein are biorenewable polyesters derived from camphoric acid. In one aspect, the polymers disclosed herein can be characterized by any technique known in the art including, for example, nuclear magnetic resonance spectroscopy ($^1$H NMR, $^{13}$C NMR, two-dimensional NMR techniques, or a combination thereof), differential scanning calorimetry, thermogravimetric analysis, gel permeation chromatography, and other suitable techniques.

In a further aspect, disclosed herein is the preparation of various monomers useful in the reactions disclosed herein. In one aspect, described herein is a method for preparation of the monomer cis-1,4-anhydroerythritol (erythritan). In a further aspect, erythritol can be melted in a flask with stirring. In one aspect, the erythritol is heated at 130° C. until all of the erythritol is melted. Following this, p-toluenesulfonic acid can be added to the melted erythritol and stirring can continue at an elevated temperature for from 1 to 4 hours, or for 1, 1.5, 2, 2.5, 3, 3.5, or about 4 hours, or a combination of any of the foregoing values, or a range encompassing any of the foregoing values. In one aspect, stirring is conducted for 2.5 hours. In a further aspect, stirring can be continued for an additional period of time at a lower temperature that is still above room temperature. In one aspect, the additional period of time can be from 30 to 90 minutes, or can be about 30, 40, 50, 60, 70, 80, or about 90 minutes, or a combination of any of the foregoing values, or a range encompassing any of the foregoing values. In one aspect, stirring is carried out for 1 hour. In another aspect, the temperature for this second stirring step can be from about 70 to about 110° C., or about 70, 75, 80, 85, 90, 95, 100, 105, or about 110° C., or a combination of any of the foregoing values, or a range encompassing any of the foregoing values. In one aspect, the temperature for the second stirring step is about 90° C. In another aspect, following both stirring steps, the reaction mixture can be cooled to room temperature and an aqueous base such as, for example, sodium bicarbonate can be added to quench the reaction. In some aspects, silica gel is further added to the quenched reaction mixture. In still another aspect, a solvent such as, for example, ethyl acetate can additionally be added to the reaction mixture and stirring can be carried out for a period of time. In one aspect, stirring is carried out for about 1 hour. In a further aspect, following stirring, solids can be removed from the aforementioned mixture by any appropriate means such as, for example, filtration. In some aspects, following filtration, additional ethyl acetate or other solvent can be used to wash the removed solids. Following filtration and washing, in some aspects, the solution can be concentrated and further purified by a method such as, for example, distillation. In some aspects, distillation is carried out under reduced pressure and at an elevated temperature.

In another aspect, disclosed herein is a method for synthesis of bis(2-hydroxyethyl) camphorate (BHEC). Further in this aspect, camphoric acid and ethylene glycol can be added to a flask. In one aspect, the camphoric acid is (1R,3S)-(+)-camphoric acid. In another aspect, the camphoric acid is (1S,3R)-(−)-camphoric acid. In still another aspect, the camphoric acid is a mixture of the two. In any of these aspects, a concentrated acid such as, for example, HCl, can be added to the flask containing camphoric acid and ethylene glycol. In any of these aspects, addition of HCl may result in the formation of solid particles. When solid particles form, ethylene glycol can be added until the mixture becomes homogeneous. In a further aspect, the reaction mixture can be heated to a temperature above room temperature such as, for example, from about 70 to about 110° C., or about 70, 75, 80, 85, 90, 95, 100, 105, or about 110° C., or a combination of any of the foregoing values, or a range encompassing any of the foregoing values. In one aspect, the mixture is heated to about 90° C. In a further aspect, the heating is continued overnight. In any of these aspects, following heating, neutralization is accomplished by adding a saturated solution of a base such as, for example, sodium hydroxide in ethylene glycol. In one aspect, neutralization can be tested by monitoring the pH of the reaction mixture, where a pH of 7 indicates neutralization has been completed. In a further aspect, following neutralization, ethylene glycol can be removed at elevated temperature (e.g., 120° C.) under reduced pressure. Following removal of ethylene glycol, acetone or another solvent can be added to the reaction vessel, forming solids. In one aspect, the solids are then filtered out of the solution and the acetone is evaporated to leave BHEC.

In still another aspect, disclosed herein are an apparatus and procedure for synthesizing the disclosed polymers. In a further aspect, polymerizations can be conducted in a round bottom flask connected to a rotary evaporation bump trap affixed to a Schlenk line. In one aspect, this apparatus is particularly convenient because condensation byproducts and volatiles (e.g., water) can be removed without changing the glassware configuration.

In one aspect, polymers are melted to remove them from the flask in which they are formed. In another aspect, the polymers are characterized as disclosed herein without further purification. In some aspects, rotoirregularity is introduced since camphoric acid includes two stereocenters. In a further aspect, additional $^1H$ and/or $^{13}C$ NMR peaks may be present that would not be found in a regioregular structure.

In some aspects, a dual catalyst process is used for polymerizations as disclosed herein. In a further aspect, the catalysts can be any useful catalysts but may include $Zn(OAc)_2$, $Sb_2O_3$, or a combination thereof. In one aspect, the catalysts are added simultaneously. In an alternative aspect, the catalysts are added sequentially. In any of these aspects, the polymerizations can be conducted neat (i.e., with no solvent) or can be conducted in a solvent. In a further aspect, camphoric acid and a diol (e.g., ethylene glycol, 1,3-propanediol, 1,4-butanediol, or another diol disclosed herein, including non-linear diols such as, for example, erythritan and/or isosorbide) are stirred under an inert atmosphere such as, for example, nitrogen, at elevated temperature. In one aspect, the temperature will depend on the properties of the diol and the conditions under which the reaction mixture remains in a liquid state.

In other aspects, no catalyst is used. Further in these aspects, camphoric acid and a diol as disclosed herein are added to the reaction apparatus along with p-toluenesulfonic acid. In any of these aspects, the polymerizations can be conducted neat (i.e., with no solvent) or can be conducted in a solvent. In a further aspect, stirring is conducted under an inert atmosphere at elevated temperature. In another aspect, the temperature will depend on the properties of the diol and the conditions under which the reaction mixture remains in a liquid state.

In any of the above aspects, a slight excess of diol is included to ensure full incorporation into the initially formed oligomers.

Exemplary procedures for preparing the monomers and polymers disclosed herein are provided in the Examples.

In one aspect, the polymers disclosed herein have Mn values (i.e., number average molecular weight) of from about 5,000 to about 25,000 Da, or of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000 Da, or a combination of any of the foregoing values, or a range encompassing any of the foregoing values. In one aspect, the Mn value is from about 7,300 Da to about 20,200 Da. In one aspect, longer diols may afford polymers with lower molecular weights (i.e., with Mn values from about 7,300 to about 8,300) regardless of the technique used (e.g., dual catalyst or p-toluenesulfonic acid).

In a further aspect, the polymers disclosed herein have Mw values (i.e., weight average molecular weight) of from about 15,000 to about 80,000 Da, or of about 15,000, 20,000, 25,000, 30,000, 35,000, 40,000, 45,000, 50,000, 55,000, 60,000, 65,000, 70,000, 75,000, or about 80,000 Da, or a combination of any of the foregoing values, or a range encompassing any of the foregoing values. In one aspect, the Mw value is from about 19,600 to about 75,700 Da.

In still another aspect, the dispersity values of the polymers disclosed herein can range from about 2 to about 5, or can be about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0, or a combination of any of the foregoing values, or a range encompassing any of the foregoing values. In one aspect, the dispersity values of the polymers range from about 2.7 to about 4.4.

In one aspect, the polymers disclosed herein have glass transition temperatures ($T_g$) of from about −20° C. to about 130° C., or of about −20, −15, −10, −5, 0, 5, 10, 15, 20, 25, 30, 35, 40, 45, 50, 55, 60, 65, 70, 75, 80, 85, 90, 95, 100, 105, 110, 115, 120, 125, or about 130° C., or a combination of any of the foregoing values, or a range encompassing any of the foregoing values. In one aspect, the $T_g$ can be −16° C. (1,6-hexanediol connector), 51° C. (ethylene glycol connector), 100° C. (erythritan connector), or 125° C. (isosorbide connector). In one aspect, $T_g$ decreases as diol length increases, for alkylene diols. In another aspect, connectors composed of rigid diols such as, for example, erythritan or isosorbide can have $T_g$ values of 100° C. or more. In another aspect, some or all of the polymers disclosed herein are not crystalline. Further in this aspect, no melting temperature is observed via differential scanning calorimetry for non-crystalline polymers.

In another aspect, T5 is defined herein as the temperature at which 5% mass loss under nitrogen is observed according to thermogravimetric analysis. In one aspect, the T5 decomposition temperature can be from about 300 to about 400° C., or can be about 300, 305, 310, 315, 320, 325, 330, 335, 340, 345, 350, 355, 360, 365, 370, 375, 380, 385, 390, 395, or about 400° C., or a combination of any of the foregoing values, or a range encompassing any of the foregoing values. In one aspect, the T5 decomposition temperature ranges from about 322° C. to about 368° C., or is about 322° C. or about 368° C.

In one aspect, although excess diol can be used herein to ensure complete reaction, molecular weight and dispersity parameters of diacid/diol copolymerizations may be sensitive to slight deviations of the ideal 1:1 reaction stoichiometry. Further in this aspect, BHEC (synthesis disclosed previously and expanded upon in the Examples) and bis (hydroxyethyl) terephthalate (BHET) can be copolymerized with varying feed fractions via transesterification with $Sb_2O_3$. In one aspect, BHEC incorporation can be lower than its feed fraction. Further in this aspect, BHEC may be more difficult to polymerize than BHET. Without wishing to be bound by theory, steric encumbrance may be able to hinder the reactivity of BHEC as compared to BHET.

In one aspect, BHET content of BHEC/BHET polyester copolymers can be from about 0% to about 95%, or can be about 0, 5, 10, 15, 20, 25, 30, 35, 40, 45, 50, 55, 60, 65, 70, 75, 80, 85, 90, or about 95%, or a combination of any of the foregoing values, or a range encompassing any of the foregoing values. In one aspect, BHET content can be about 17.1%, about 34.2%, about 47.3%, about 66%, bout 68.4%, 77.8%, about 80.2%, about 87.7%, or about 92.4%. In another aspect, the BHEC/BHET polyester copolymers disclosed herein have a bio-based content (e.g., camphoric acid level) of from about 5% to about 75%, or of about 5, 10, 15, 20, 25, 30, 35, 40, 45, 50, 55, 60, 65, 70, or about 75%, or a combination of any of the foregoing values, or a range encompassing any of the foregoing values. In another aspect, the polyester copolymers disclosed herein have a bio-based content of from about 6.5% to about 73.5%.

In one aspect, Mw of BHEC/BHET polyester copolymers can range from about 30,000 to about 60,000 Da, or can be about 30,000, 35,000, 40,000, 45,000, 50,000, 55,000, or about 60,000 or a combination of any of the foregoing values, or a range encompassing any of the foregoing values. In one aspect, the Mw can be about 33,100 or about 59,200 Da.

In one aspect, Mn of BHEC/BHET polyester copolymers can range from about 10,000 to about 25,000 Da, or can be about 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20.500, 21,000, 21,500, 22,000, 22,500, 23,000, 23,500, 24,000, 24,500, or about 25,000 Da, or a combination of any of the foregoing values, or a range encompassing any of the foregoing values. In one aspect, the Mn can be about 13,300, about 17,900, or about 23,800 Da.

In a further aspect, dispersity values of the BHEC/BHET polyester copolymers disclosed herein can be between about 2 and 3, or can be about 2.0, 2.1, 2.2, 2.3, 2.4, 2.5, 2.6, 2.7, 2.8, 2.9, or about 3.0, or a combination of any of the foregoing values, or a range encompassing any of the foregoing values. In one aspect, the dispersity value can be 2.3 or can be 2.9.

In still another aspect, $T_g$ of the BHEC/BHET polyester copolymers disclosed herein can be between about 35 and about 75° C., or can be about 35, 40, 45, 50, 55, 60, 65, 70, or about 75° C., or a combination of any of the foregoing values, or a range encompassing any of the foregoing values. In one aspect, the $T_g$ value can be about 41° C. or can be about 71° C. Without wishing to be bound by theory, a higher BHEC content results in a lower $T_g$, while a higher BHET content results in a higher $T_g$. In a further aspect, with higher BHET incorporation (i.e., 80% or greater), the polymers may become crystalline. When polymers are crystalline, the melting temperature can be from about 175° C. to about 235° C., or can be about 175, 180, 185, 190, 195, 200, 205, 210, 215, 220, 225, 230, or about 235° C., or a combination of any of the foregoing values, or a range encompassing any of the foregoing values. In one aspect, the melting temperature is about 180° C. or is about 229° C.

In still another aspect, T5 for the BHEC/BHET polyester copolymers can be from about 330 to about 375° C., or can be about 330, 335, 340, 345, 350, 355, 360, 365, 370, or about 375° C., or a combination of any of the foregoing values, or a range encompassing any of the foregoing values. In one aspect, T5 is about 335° C. or is about 371° C.

Uses for the Biorenewable Polyesters Derived from Camphoric Acid

In one aspect, disclosed herein are articles made from or incorporating at least a portion of the polyester polymers and/or polyester copolymers disclosed herein.

In a further aspect, the disclosed biorenewable polyester polymers and/or polyester copolymers can be used in the manufacture of an article comprising a conventional polyester or polyester copolymer and replacing in whole or in part a conventional polyester or polyester copolymer in said articles. The article can comprise on wt % basis replacement of a given percentage of the conventional polyester or polyester copolymer with a disclosed biorenewable polyester polymer and/or polyester copolymer of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%; or a range utilize as an upper and lower bound any of two of the foregoing values.

In some aspects, the polyester polymers and/or polyester copolymers disclosed herein can be used to mimic polymers already in industrial use. Without wishing to be bound by theory, the polyester polymers and polyester copolymers disclosed herein may share similar behavior with other polymers having similar glass transition temperatures ($T_g$). In one aspect, for example, polylactic acid has a $T_g$ of 55° C., so a polyester polymer or copolymer disclosed herein having a $T_g$ from about 50° C. to about 60° C. can be used in place of polylactic acid in some applications. In another aspect, polystyrene has a $T_g$ of about 95° C., so a polyester polymer or copolymer disclosed herein having a $T_g$ of from about 90° C. to about 100° C. can be used in place of polystyrene in some applications. In still another aspect, polymethylmethacrylate has a $T_g$ of about 105° C., so a polyester polymer or copolymer disclosed herein having a $T_g$ of from about 100° C. to about 110° C. can be used in place of polymethylmethacrylate in some applications. In still other aspects, polyester polymers and/or copolymers disclosed herein can be mixed with one another or with existing polymers to fine tune the properties of the resulting materials.

In another aspect, the disclosed biorenewable polyester polymers and/or polyester copolymers disclosed herein can be used in applications including food sources, cosmetics, sewage treatment including coagulation and flocculation agents, stabilizing agents in plastics, plasma substitutes, rheologoy modifiers, latex coatings, encapsulation, pharmaceuticals and drug delivery, cementitious materials and/or adhesives, sealants, waterproofing and/or sealants, chromatography and other separations, fibers and textiles, construction materials, oil field cementing and drilling, energy absorption and reinforcement applications, cushioning, insulation, and the like.

REFERENCES

References are cited herein throughout using the format of reference number(s) enclosed by parentheses corresponding to one or more of the following numbered references. For example, citation of references numbers 1 and 2 immediately herein below would be indicated in the disclosure as (Refs. 1 and 2).

Ref 1. A. Gandini, Biocatalysis in Polymer Chemistry, ed. K. Loos, Wiley-VCH Verlag GmbH & Co. kGaA, Weinheim, Germany, 2011, pp. 1-33.
Ref 2. F. Rodriguez, C. Cohen, C. K. Ober, L. A. Archer, Principles of Polymer Systems, Taylor & Francis, New York, 2003, p. 4.
Ref 3. S. A. Miller, ACS Macro Lett., 2013, 2, 550-554.
Ref 4. C. J. Moore, Environ. Res., 2008, 108, 131-139.
Ref 5. R. G. Miller and S. R. Sorrell, Philos Trans A Math Phys Eng Sci., 2014, 372, 1-27.
Ref 6. J. Rass-Hansen, H. Falsig, B. Jorgensen and C. H. Christensen, J. Chem. Technol. Biotechnol., 2007, 82, 329-333.
Ref 7. P. B. Weisz, Phys. Today, 2004, 57, 47-52.
Ref 8. D. K. Schneiderman and M. A. Hillmyer, Macromolecules, 2017, 50, 3733-3749.
Ref 9. H. T. H. Nguyen, P. Qi, M. Rostagno, A. Feteha and S. A. Miller, J. Mater. Chem. A, 2018, 6, 9298-9331.
Ref 10. R. Mulhaupt, Macromol. Chem. Phys., 2013, 214, 159-174.
Ref 11. A. Gandini, Green Chem., 2011, 23, 1061-1083.
Ref 12. J. V. Kurian, J. Polym. Environ., 2005, 13, 159-167.
Ref 13. C. K. Williams and M. A. Hillmyer, Polymer Rev., 2008, 48, 1-10.
Ref 14. K. Yao and C. Tang, Macromolecules, 2013, 46, 1689-1712.
Ref 15. A. L. Holmberg, K. H. Reno, R. P. Wool and T. H., Ill Epps, Soft Matter, 2014, 10, 7405-7424.
Ref 16. M. J. L. Tschan, E. Brule, P. Haquette and C. M. Thomas, Polym. Chem., 2012, 3, 836-851.
Ref 17. S. Paul, Y. Zhu, C. Romain, R. Brooks, P. K. Saini and C. K. Williams, Chem. Commun., 2015, 51, 6459-6479.
Ref 18. R. T. Mathers, J. Polym. Sci., Part A: Polym. Chem., 2012, 50, 1-15.
Ref 19. J. M. Becker, R. J. Pounder and A. P. Dove, Macromol. Rapid Commun., 2010, 31, 1923-1937.
Ref 20. Y. Rudeekit, J. Numnoi, M. Tajan, P. Chaiwutthinan and T. Leejarkpai, J. Met. Mater. Miner., 2008, 18, 83-87.
Ref 21. M. Kunioka, F. Ninomiya and M. Funabashi, Polym. Degrad. Stab., 2006, 91, 1919-1928.
Ref 22. H. T. H. Nguyen, G. N. Short, P. Qi and S. A. Miller, Green Chem., 2017, 19, 1877-1888.
Ref 23. H. T. H. Nguyen, M. H. Reis, P. Qi and S. A. Miller, Green Chem., 2015, 17, 4512-4517.
Ref 24. L. Mialon, A. G. Pemba and S. A. Miller, Green Chem., 2010, 12, 1704-1706.
Ref 25. P. Qi, H.-L. Chen, H. T. H. Nguyen, C.-C. Lin and S. A. Miller, Green Chem., 2016, 18, 4170-4175.
Ref 26. M. Rostagno, S. Shen, I. Ghiviriga, S. A. Miller. Polym. Chem., 2017, 8, 5049-5059.
Ref 27. S. Guo, Z, Geng, W. Zhang, J. Liang, C. Wang, Z. Deng and S. Du, Int. J. Mol. Sci., 2016, 17, 1836.
Ref 28. S. K. Talapatra and B. Talapatra Chemistry of plant natural products, Springer-Verlag berlin Heidelberg, New Delhi, 2015, p. 377.
Ref 29. M. Hofer and J. Müller, Fraunhofer IGB Press Release, Monomers from camphor enable biobased plastics, Aug. 3, 2018. Accessed December 2018. https://www.igb.fraunhofer.de/en/press-media/press-releases/2018/camphor-based-polymers.html; https://www.bioplasticsmagazine.com/en/news/meldungen/20181104-Can-camphor-offer-an-alternative-to-castor-oil-to-produce-bio-PA-.php.
Ref 30. (a) W. Chen, I. Vermaak and A. Viljoen, Molecules 2013, 18, 2013. (b) J. J. Ritter, J. Am. Chem. Soc., 1933, 55, 3322-3326.
Ref 31. W. Liu, Terpenes: The expansion of chiral pool. In Handbook of Chiral Chemicals, 2nd ed.; Ager, D. J., Ed.; CRC Press: Boca Raton, Fla., USA, 2005; p. 65.
Ref 32. D. Ponomarev and H. Mettee, Chem. Educ. J., 2016, 18, 1-4.
Ref 33. I. Gubelmann and H. W. Elley, Ind. Eng. Chem., 1934, 26, 589-594.
Ref 34. M. L. Beri, J. L. Sarin, J. Chem. Technol. Biotechnol., 1936, 55, 605-607.
Ref 35. Zauba.com, Detailed Import Data of camphor. Accessed December 2018. https://www.zauba.com/import-camphor-hs-code.html.

Ref 36. Z. Rafinski and A. Kozakiewcz, J. Org. Chem., 2015, 80, 7468-7476.
Ref 37. E. Rais, U. Floerke and R. Wilhelm, Synthesis, 2017, 49, 2852-2864.
Ref 38. C. Li, K. Jiang, T. Y. Liu, and Y. C. Chen, Adv. Synth. Catal., 2017, 359, 2530-2534.
Ref 39. F. Xu, L. Yan, C. Lei, H. Zhao and G. Li. Tetrahedron: Asymmetry, 2015, 26, 338-343.
Ref 40. H. L. Wu, P. Y. Wu, Y. N. Cheng and B. J. Uang, Tetrahedron, 2016, 72, 2656-2665.
Ref 41. Berthelot was likely the first to make a "combinaison" ("combination") with camphoric acid, combining it with glycerol to make a crosslinked polyester of the alkyd resin type. (a) Berthelot, M. Comptes Rend., 1853, 37, 398. (b) McIntyre, J. E. "The Historical Development of Polyesters" in Modern Polyesters: Chemistry and Technology of Polyesters and Copolyesters, Scheirs, J. and Long, T. E., Eds.; John Wiley & Sons: New York, 2003, p. 3-28.
Ref 42. Polybutylene camphorate (Mn=3,600) has been reported, but there is no mention of its thermal properties. Toy, M. S. J. Polym. Sci. A-1 Polym. Chem. 1967, 5, 2481-2486.
Ref 43. H. S. Zhang, J. Li, Z. L. Tian and F. Liu, J. Appl. Polym. Sci., 2013, 129, 3333-3340.
Ref 44. C. Robert, F. de Montigny and C. M. Thomas, Nat. Commun., 2011, 2, 586.
Ref 45. L. Fournier, C. Robert, S. Pourchet, A. Gonzalez, Williams, J. Prunet and C. M. Thomas, Polym. Chem., 2016, 7, 3700-3704.
Ref 46. G. H. Choi, D. Y. Hwang and D. H. Suh, Macromolecules, 2015, 48, 6839-6845.
Ref 47. J. E. Park, D. Y. Hwang, G.-H Choi, K. H. Choi, and D. H. Suh, Biomacromolecules, 2017, 18, 2633-2639.
Ref 48. Wosnick, J. H.; Farrugia, V. M.; Sacripante, G. G. "Toner compositions and processes," U.S. Pat. No. 8,697, 324 B2, 2014 (Xerox Corporation).
Ref 49. S. Mandal and A. Dey, "PET Chemistry" in Recycling of Polyethylene Terephthalate Bottles, S. Thomas, A. Rane, K. Kanny, A. V. K., and M. G. Thomas, Eds., Elsevier, Oxford, U K, 2019. pp. 1-22.
Ref 50. Garlotta, D., J. Polym. Environ., 2002, 9, 63-84.
Ref 51. A. P. Dove, Chem. Commun., 2008, 6446,-6470.
Ref 52. F. Bukhamseen and L. Novotny, Res. J. Pharm. Biol. Chem. Sci., 2014, 5, 638-649.
Ref 53. K. Regnat, R. L. Mach and A. R. Mach-Aigner, Appl. Microbiol. Biotechnol., 2018, 102, 587-595.
Ref 54. J. Hong, D. Radojcic, M. lonescu, Z. S. Petrovic and E. Eastwood, Polym. Chem., 2014, 5, 5360-5368.
Ref 55. F. Fenouillot, A. Rousseau, G. Colomines, R. Saint-Loup and J. P. Pascault, Prog. Polym. Sci., 2010, 35, 578-622.
Ref 56. L. Gustini, C. Lavilla, A. M. de llarduya, S. Munoz-Guerra and C. E. Koning, Biomacromolecules, 2016, 17, 3404-3416.
Ref 57. S. Hansen and K. B. Atwood, "Polyester Fibers" in Kirk-Othmer Encyclopedia of Chemical Technology, John Wiley & Sons, 2005. DOI: 10.1002/0471238961.1615122508011419.a01.pub2.
Ref 58. H. Ren, F. Qiao, Y. Shi, M. W. Knutzen, Z. Want, H. Du and H. Zhang, J. Renew. Sustain. Energy, 2015, 7, 041510.
Ref 59. D. I. Collias, A. M. Harris, V. Nagpal, I. W. Cottrell and M. W. Schultheis, Ind. Biotechnol., 2014, 10. DOI: 10.1089/ind.2014.0002
Ref 60. M. Charton, J. Am. Chem. Soc., 1975, 97, 1552-1556.
Ref 61. R. T. Martin, L. P. Camargo and S. A. Miller, Green Chem., 2014, 16, 1768-1773.
Ref 62. C. C. Chu, J. Appl. Polym. Sci., 1981, 26, 1727-1734.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials and Characterization (+)-Camphoric acid (99%) and ethylene glycol were purchased from Fisher Scientific and used without further purification. 1,3-propanediol (99.6+%), 1,4-butanediol (99%), 1,5-pentanediol (99%), 1,6-hexanediol (99%), bis(2-hydroxyethyl) terephthalate, and para-toluenesulfonic acid (p-TSA) monohydrate were purchased from Sigma-Aldrich and used as received. "Healthy Foods" erythritol (100% pure) was purchased from Amazon and isosorbide (98%) was purchased from Fisher and recrystallized from ethyl acetate. Antimony oxide ($Sb_2O_3$, 99.5%), a catalyst for polymerization, was purchased from Acros and used as received. Deionized water and saturated aqueous HCl solution were purchased from Fisher Scientific. NMR solvents, including deuterated chloroform ($CDCl_3$) and deuterated trifluoroacetic acid (TFA-d), which do not contain tetramethylsilane (TMS), were purchased from Cambridge Isotope Laboratories. All other chemicals, unless expressly mentioned, were used as received.

Proton and carbon nuclear magnetic resonance ($^1$H and $^{13}$C NMR) spectra were recorded using a Varian Inova 500 MHz spectrometer. Chemical shifts are reported in parts per million (ppm) downfield relative to tetramethylsilane (TMS, 0.0 ppm) or residual proton and carbon in the specified solvent. Coupling constants (J) are reported in Hertz (Hz). Multiplicities are reported using the following abbreviations: s, singlet; d, doublet; t, triplet; q, quartet; quin, quintet; m, multiplet; br, broad.

Differential scanning calorimetry (DSC) thermograms were obtained with a DSC Q1000 from TA instruments. About 3-5 mg of each sample were massed and added to a sealed pan that passed through a heat/cool/heat cycle at 10° C./min. Reported data are from the second full cycle. The temperature ranged from −50 to 200° C., depending on the sample.

Thermogravimetric analyses (TGA) were measured under nitrogen with a TGA Q5000 from TA Instruments. About 5-10 mg of each sample was heated at 20° C./min from 25 to 600° C.

Gel permeation chromatography (GPC) was performed at 40° C. using an Agilent Technologies 1260 Infinity Series liquid chromatography system with an internal differential refractive index detector, and a PL HFIP gel column (7.5 mm i.d., 300 mm length) using a solution of 0.1% potassium triflate (K(OTf)) in HPLC grade hexafluoroisopropanol (HFIP) as the mobile phase at a flow rate of 0.3 mL/min. Calibration was performed with narrow dispersity polymethylmethacrylate (PMMA) standards.

Monomer Preparation

Synthesis of cis-1,4-anhydroerythritol (Erythritan)

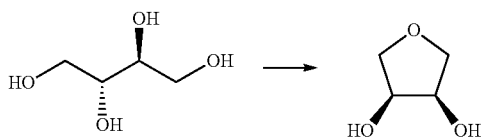 [SMILES: OC[C@@H](O)[C@@H](O)CO ; O[C@@H]1COC[C@@H]1O]

Figure 27A:
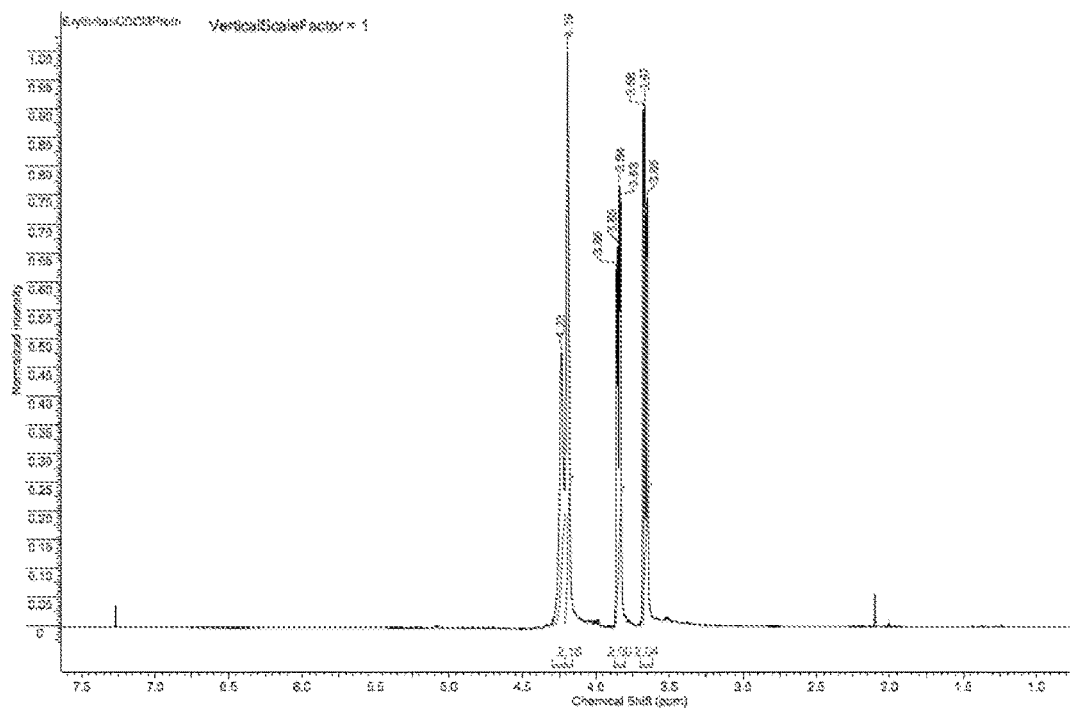
FIGS. 27A-B show nuclear magnetic resonance spectra of the erythritan monomer.
Figure 27B:
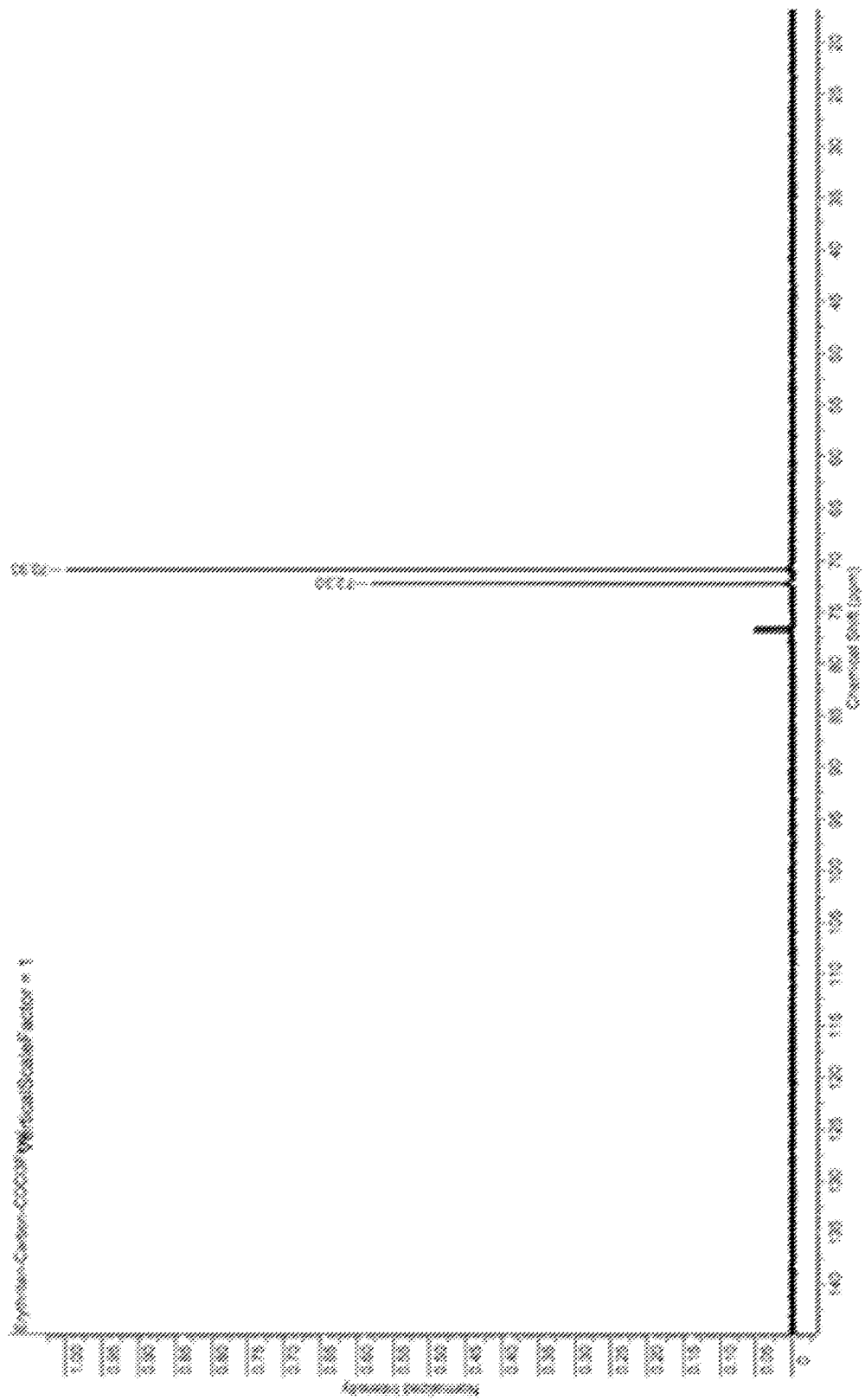

24.4 g (200 mmol) of erythritol were added to a 250 mL round bottom flask equipped with a magnetic stir bar. The temperature was set to 135° C. until erythritol melted. Then 1.90 g (5 mol %) of p-toluene sulfonic acid were added and the mixture was stirred for 2.5 hours. After that time elapsed, the mixture was cooled to 90° C. and then stirred for 1 hour. After that it was cooled to room temperature and 3.36 g (2 mol %) of sodium bicarbonate were added along with 30 g of silica gel. 150 mL of ethyl acetate were added to the mixture and it was stirred for 1 hour. The solids were removed by filtration and washed with an additional 100 mL of ethyl acetate. The solution was then concentrated and a light yellow oil remained. The product was then purified by distillation a follows: a round bottom flask was fitted to a distillation apparatus containing a fractionating column, a reflux condenser, and a collecting flask. The system was heated to 175° C. under reduced pressure (0.5 torr) for 6 hours. After that time had elapsed, 20.0 g of cis-1,4-anhydroerythritol was collected (65% yield). $^1$H NMR (CDCl$_3$): δ ppm 3.66 (dd, J=9.6, 5.0 Hz, 2H), 3.85 (dd, J=9.5, 4.9 Hz, 2H), 4.19 (br. s., 2H), 4.23 (br. s., 2H). $^{13}$C NMR (CDCl$_3$): δ ppm 70.9, 72.3. Further characterization is provided in FIGS. 27A-B.

Synthesis of bis(2-hydroxyethyl) Camphorate (BHEC)

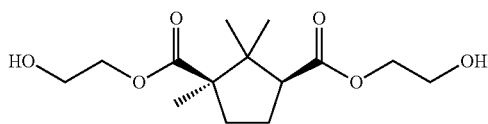 [SMILES: CC1(C)[C@@H](C(=O)OCCO)CC[C@@]1(C)C(=O)OCCO]

Figure 28A:
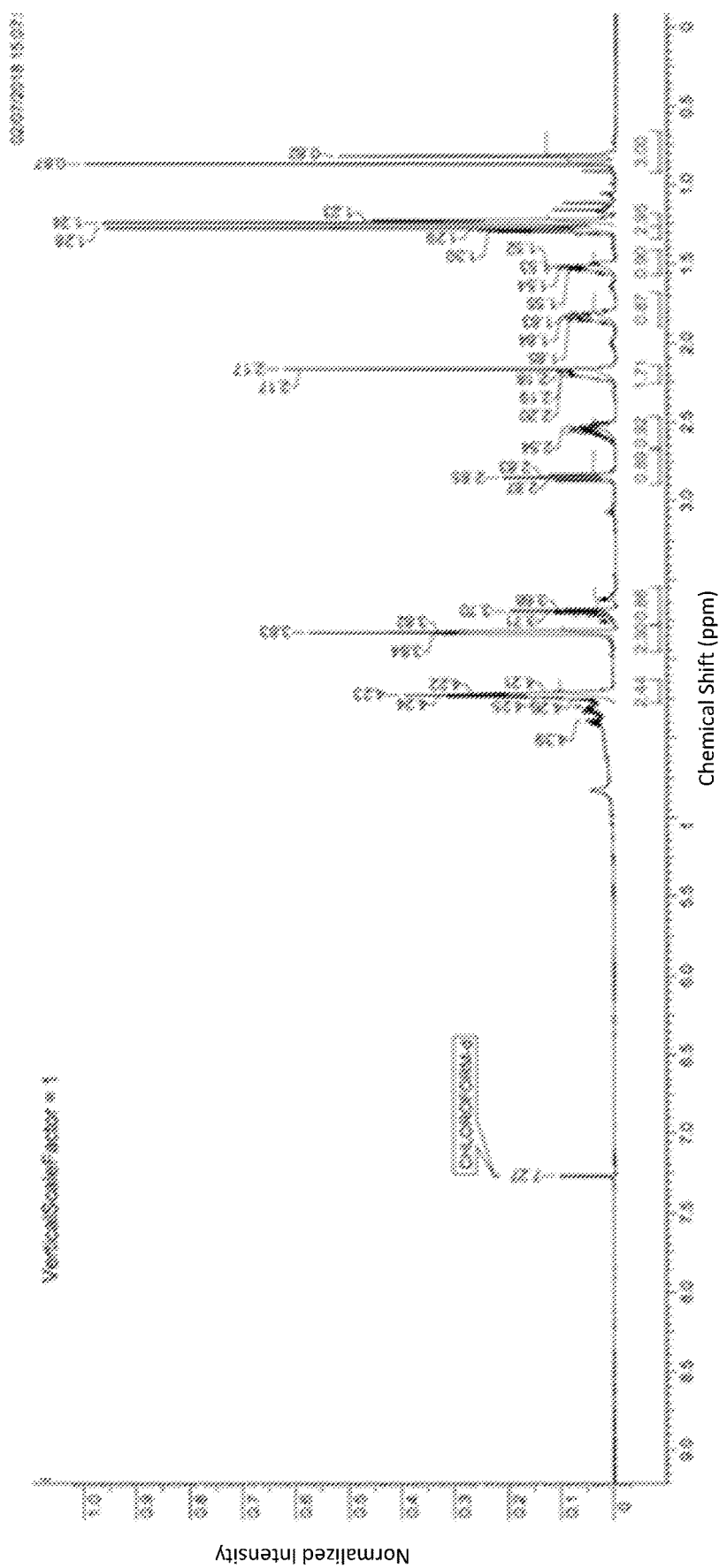
FIGS. 28A-B show nuclear magnetic resonance spectra of the BHEC monomer.
Figure 28B:
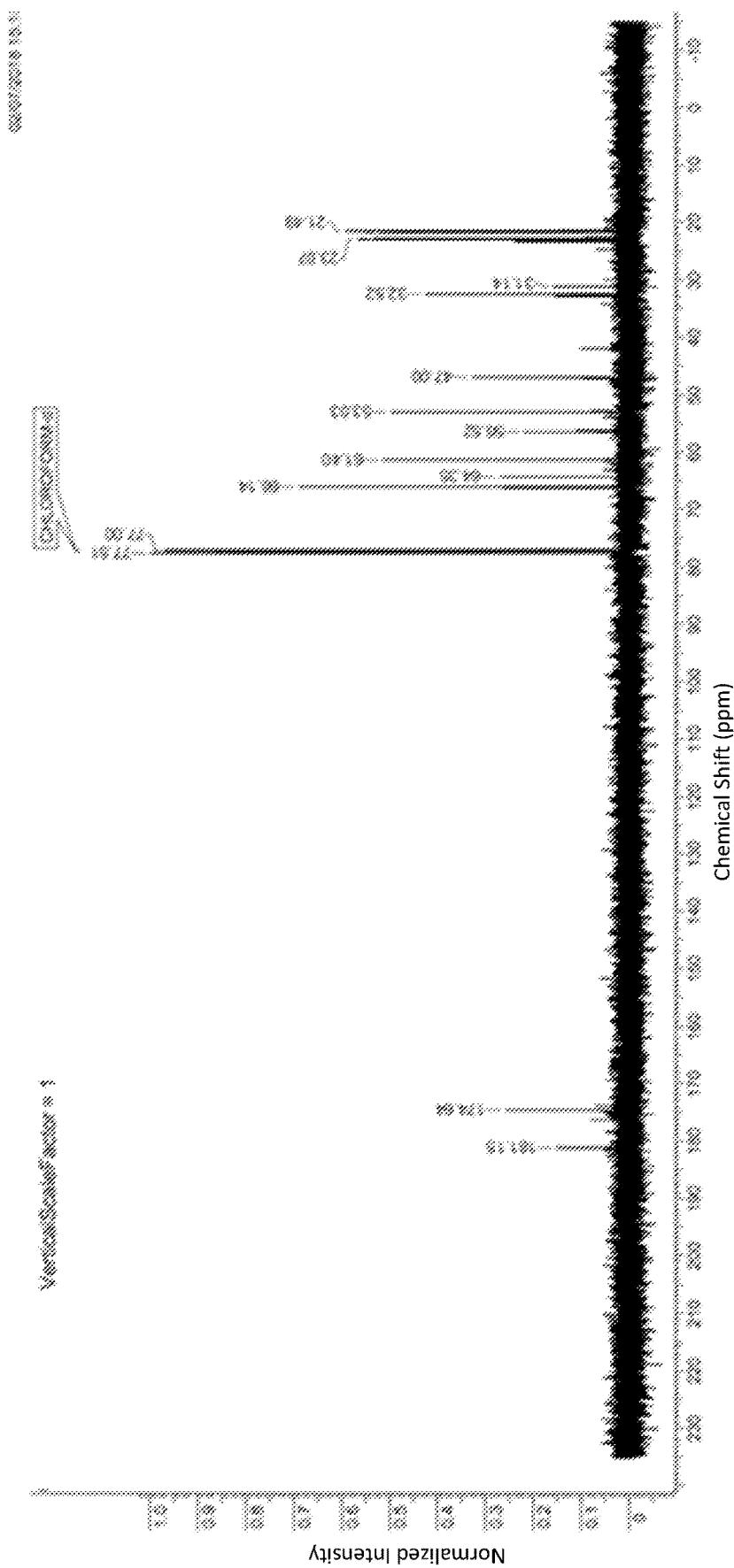

In a 200 mL round bottom flask, 8.00 g (40 mmol) of camphoric and 50 mL of ethylene glycol (excess) were added. 12 mL of concentrated HCl were added and some solid particles formed. More ethylene glycol was added until the mixture became homogeneous. The reaction was heated at 90° C. overnight before neutralization by adding a saturated solution of NaOH in ethylene glycol until the pH of the solution was neutral. Then ethylene glycol was evaporated on a Schlenk line under reduced pressure at 120° C. Acetone was added to the flask and the formed solids were removed by filtration. Acetone was evaporated and a light yellow liquid was obtained as the product (7.00 g, 61% yield). $^1$H NMR (CDCl$_3$): δ 0.87 (s, 3H), 1.24 (s, 3H), 1.26 (s, 3H), 1.53 (m, 1H), 1.84 (m, 1H), 2.17 (m, 1H), 2.54 (m, 1H), 2.85 (t, J=9.4 Hz, 1H), 3.83 (m, 2H), 4.23 (m, 2H), 4.32 (m, 2H), 4.39 (m, 2H), 4.82, (br s., 2H). $^{13}$C NMR (CDCl$_3$): δ 21.5, 21.8, 22.8, 23.1, 31.1, 32.5, 47.0, 53.0, 56.5, 61.4, 64.4, 66.1, 174.6, 181.2. Further characterization is provided in FIGS. 28A-B.

Polymerization

Polymerization Apparatus

The polymerizations were conducted in a round bottom flask that was connected to a rotary evaporation bump trap affixed to a Schlenk line. With this apparatus, the by-product of condensation and volatiles (water primarily) were removed without changing the initial glassware configuration.

General Work-Up Procedure for Polymerizations

All polymers were melted to remove them from the flask and were characterized without further purification. Note: Regioirregularity is introduced because of the unsymmetrical nature of camphoric acid. This can result in additional $^1$H and $^{13}$C NMR peaks not prescribed by a regioregular structure.

Polyethylene Camphorate (PEC), Dual Catalyst Process

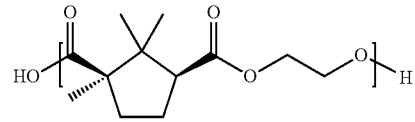

Table 1, Entry 1. 2.00 g (10 mmol) of (+)-camphoric acid was added to a 50 mL round bottom flask with a magnetic stir bar. 0.744 g (12.0 mmol) of ethylene glycol and 37 mg of zinc acetate (Zn(OAc)$_2$, 2 mol %) were added to the flask. The polymerization was conducted under melt conditions (no solvent) starting at 180° C. under nitrogen for 10 hours and then 29 mg of antimony oxide (Sb$_2$O$_3$, 1 mol %) was added. The mixture was stirred again under nitrogen for 11 hours. After that time had elapsed, the mixture was subjected to dynamic vacuum for 12 hours with a temperature gradient of 180-240° C. A brown polymer was obtained and removed without further purification (1.70 g, 75% yield). $^1$H NMR (CDCl$_3$): δ ppm 0.79 (s, 3H), 1.21 (s, 3H), 1.24 (br. s., 3H), 1.52 (m, 1H), 1.83 (m, 1H), 2.17 (m, 1H), 2.55 (m, 1H), 2.80 (m, 1H), 4.30 (m, 4H). $^{13}$C NMR (CDCl$_3$): δ 21.3, 21.7, 22.6, 24.5, 32.5, 52.7, 53.9, 56.2, 61.3, 62.2, 173.6, 175.3. See also FIGS. 5A-E.

Polyethylene Camphorate (PEC)

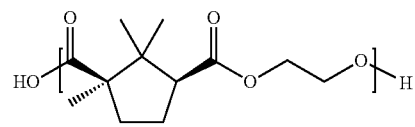

Table 1, Entry 2. 2.00 g (10 mmol) of (+)-camphoric acid were added to a 50 mL round bottom flask with a magnetic stir bar. 0.744 g (12.0 mmol) of ethylene glycol and 76 mg (4 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-230° C. A light brown polymer was obtained and removed without further purification (1.90 g, 84% yield). $^1$H NMR (CDCl$_3$): δ ppm 0.79 (s, 3H), 1.20 (s, 3H), 1.24 (s, 3H), 1.51 (m, 1H), 1.83 (m, 1H), 2.17 (m, 1H), 2.55 (m, 1H), 2.80 (t, J=9.5, 1H), 4.30 (m, 4H). $^{13}$C NMR (CDCl$_3$): δ ppm 21.0, 21.3, 22.2, 22.7, 32.2, 46.5, 54.2, 53.1, 61.5, 62.0, 173.3, 175.0. See also FIGS. 6A-E.

Polypropylene Camphorate

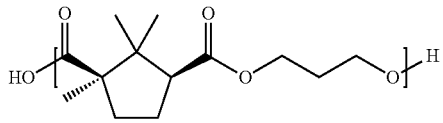

Figure 24:
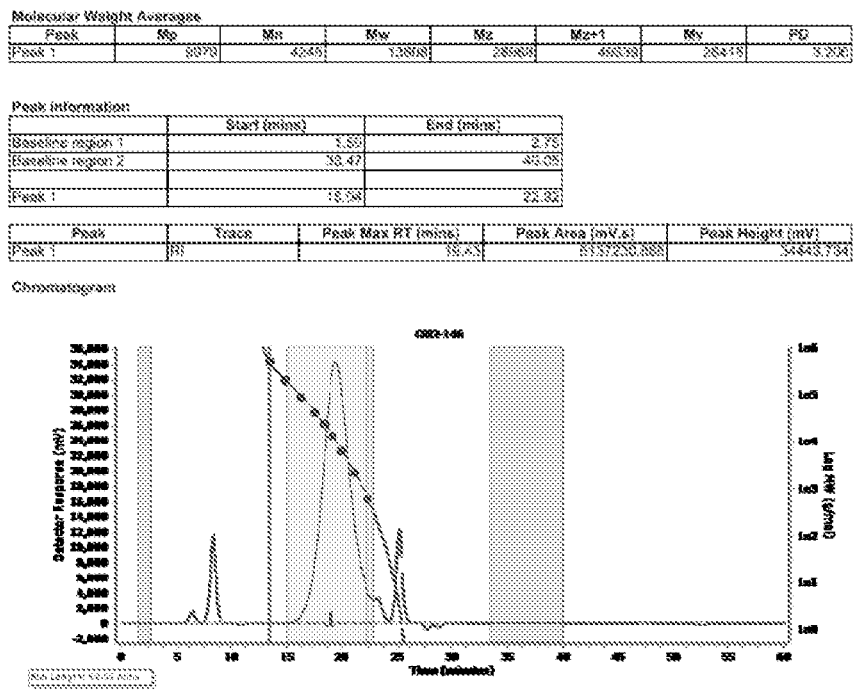
FIG. 24 shows a gel permeation chromatogram (GPC) of polypropylene camphorate (dual catalyst).

Table 1, Entry 3. 2.00 g (10 mmol) of (+)-camphoric acid were added to a 50 mL round bottom flask with a magnetic stir bar. 0.912 g (12.0 mmol) of 1,3-propanediol and 85 mg (5 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-230° C. A light brown polymer was obtained and removed without further purification (1.80 g, 75% yield). $^1$H NMR (CDCl$_3$): δ 0.76 (s, 3H), 1.19 (s, 3H), 1.23 (m, 3H), 1.50 (m, 1H), 1.83 (m, 1H), 1.99 (m, 2H), 2.16 (m, 1H), 2.55 (m, 1H), 2.78 (t, J=9.5 Hz, 1H), 4.16 (m, 4H). $^{13}$C NMR (CDCl$_3$): δ 21.3, 21.6, 22.5, 23.0, 28.0, 32.4, 46.7, 52.8, 56.2, 60.8, 60.9, 173.8, 175.4. See also FIGS. 7A-E. GPC of polypropylene camphorate prepared using the dual catalyst method can be seen in FIG. 24.

Polybutylene Camphorate

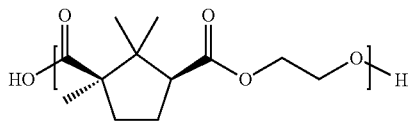

Figure 25:
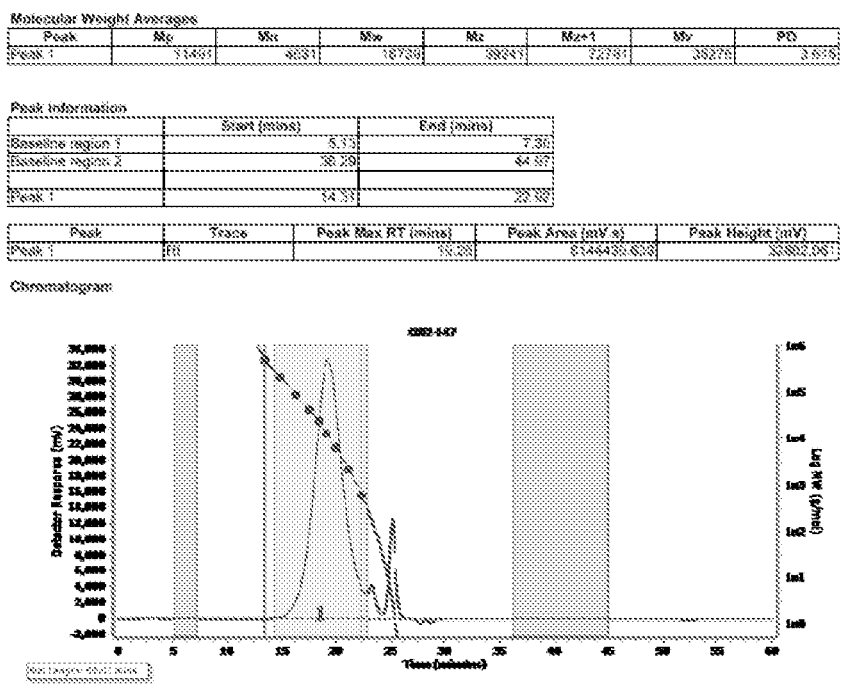
FIG. 25 shows a gel permeation chromatogram (GPC) of polybutylene camphorate (dual catalyst).

Table 1, Entry 4. 2.00 g (10 mmol) of (+)-camphoric acid were added to a 50 mL round bottom flask with a magnetic stir bar. 1.08 g (12.0 mmol) of 1,4-butanediol and 76 mg (4 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-230° C. A light brown polymer was obtained and removed without further purification (1.80 g, 71% yield). $^1$H NMR (CDCl$_3$): δ 0.77 (s, 3H), 1.20 (s, 3H), 1.24 (s, 3H), 1.50 (m, 1H), 1.72 (br. s., 4H), 1.83 (m, 1H), 2.17 (m, 1H), 2.56 (m, 1H), 2.78 (t, J=9.4 Hz, 1H), 4.11 (m, 4H). $^{13}$C NMR (CDCl$_3$): δ 21.1, 21.4, 22.3, 22.7, 25.20, 25.22, 32.2, 46.5, 52.5, 55.9, 63.5, 173.6, 175.3. See also FIGS. 8A-E. GPC of polybutylene camphorate prepared using the dual catalyst method can be seen in FIG. 25.

Polypentylene Camphorate

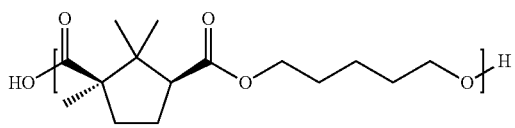

Figure 26:
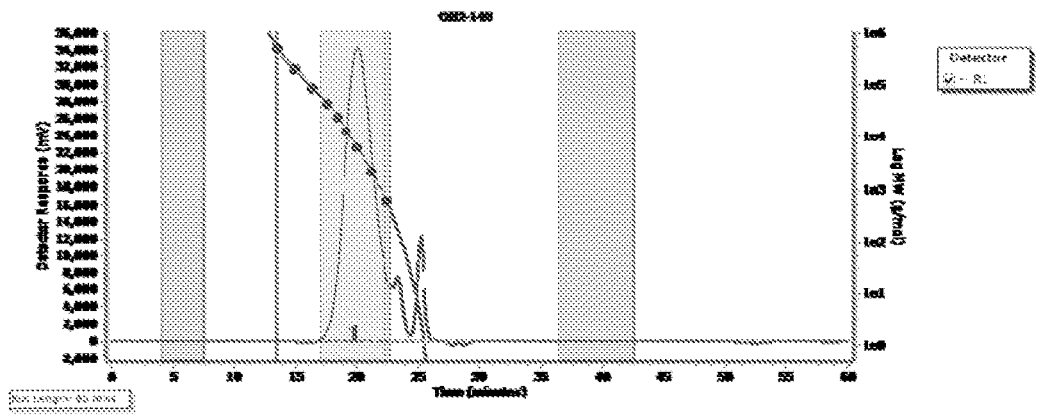
FIG. 26 shows a gel permeation chromatogram (GPC) of polypentylene camphorate (dual catalyst).

Table 1, Entry 5. 2.00 g (10 mmol) of (+)-camphoric acid were added to a 50 mL round bottom flask with a magnetic stir bar. 1.25 g (12.0 mmol) of 1,5-pentanediol and 76 mg (4 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-230° C. A light brown polymer was obtained and removed without further purification (1.96 g, 73% yield). $^1$H NMR (CDCl$_3$): δ 0.74 (s, 3H), 1.17 (br. s., 3H), 1.21 (br. s., 3H), 1.43 (m, 2H), 1.46 (m, 1H), 1.65 (br. s., 4H), 1.79 (m, 1H), 2.15 (m, 1H), 2.54 (m, 1H), 2.75 (t, J=9.5 Hz, 1H), 4.05 (m, 4H). $^{13}$C NMR (CDCl$_3$): δ 21.2, 21.6, 22.4, 22.6, 22.9, 28.1, 28.2, 32.4, 46.6, 52.8, 56.1, 64.1, 173.9, 175.6. See also FIGS. 9A-E. GPC of pentylene camphorate prepared using the dual catalyst method can be seen in FIG. 26.

Polyhexylene Camphorate

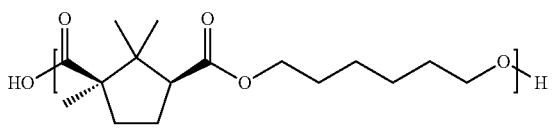

Table 1, Entry 6. 2.00 g (10 mmol) of (+)-camphoric acid were added to a 50 mL round bottom flask with a magnetic stir bar. 1.42 g (12.0 mmol) of 1,6-hexanediol and 76 mg (4 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-230° C. A light brown polymer was obtained and removed without further purification (2.70 g, 96% yield). $^1$H NMR (CDCl$_3$): δ 0.78 (s, 3H), 1.20 (s, 3H), 1.25 (s, 3H), 1.40 (m, 4H), 1.50 (m, 1H), 1.65 (m, 4H), 1.83 (m, 1H), 2.18 (m, 1H), 2.56 (m, 1H), 2.78 (t, J=9.40 Hz, 1H), 4.07 (m, 4H). $^{13}$C (CDCl$_3$): δ 21.3, 21.7, 22.6, 23.0, 25.7, 28.5, 32.5, 46.7, 52.9, 56.2, 64.3, 173.9, 175.7. See also FIGS. 10A-E.

Polyerythritan Camphorate

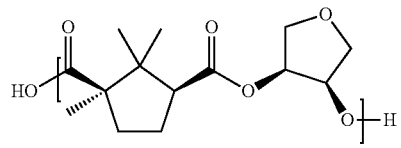

Table 1, Entry 7. 2.00 g (10 mmol) of (+)-camphoric acid were added to a 50 mL round bottom flask with a magnetic stir bar. 1.25 g (12.0 mmol) of cis-1,4-anhydroerythritol (Erythritan) and 37 mg of zinc acetate (Zn(OAc)$_2$, 2 mol %) were added to the flask. The polymerization was conducted under melt conditions (no solvent) starting at 180° C. under nitrogen for 10 hours and then 29 mg of antimony oxide (Sb$_2$O$_3$, 1 mol %) was added. The mixture was stirred again under nitrogen for 11 hours. After that time had elapsed, the mixture was subjected to dynamic vacuum for 12 hours with a temperature gradient of 180-240° C. A brown polymer was obtained and removed without further purification (1.95 g, 73% yield). $^1$H NMR (CDCl$_3$): δ 0.82 (m, 3H), 1.06 (m, 3H), 1.21 (m, 3H), 1.53 (m, 1H), 1.65 (m, 1H), 1.85 (m, 1H), 2.17 (m, 1H), 2.54 (m, 1H), 2.82 (t, J=9.3 Hz, 1H), 3.82 (m, 2H), 4.10 (m, 2H), 5.17 (br. s., 2H). $^{13}$C NMR (CDCl$_3$): δ 18.7, 21.3, 22.8, 24.2, 24.6, 32.1, 33.9, 46.7, 47.2, 52.2, 53.5, 56.2, 71.6, 172.5, 174.2. See also FIGS. 11A-E.

Polyisosorbide Camphorate

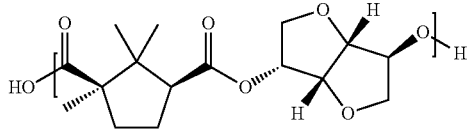

Table 1, Entry 8. 1.50 g (7.5 mmol) of (+)-camphoric acid were added to a 50 mL round bottom flask with a magnetic stir bar. 1.31 g (9.0 mmol) of isosorbide and 57 mg (4 mol %) of p-toluene sulfonic acid (p-TSA) were added to the flask. The polymerization was conducted under melt conditions (no solvent) starting at 180° C. under nitrogen for 17 hours and then subjected to dynamic vacuum for 14 hours with a temperature gradient of 180-240° C. A light brown polymer was obtained and removed without further purification (2.29 g, 98% yield). $^1$H NMR (CDCl$_3$): δ 0.86 (m, 3H), 1.18 (m, 3H), 1.23 (m, 3H), 1.55 (m, 1H), 1.84 (m, 1H), 2.17 (m, 1H), 2.56 (m, 1H), 2.80 (m, 1H), 3.78 (m, 1H), 3.96 (m, 4H), 4.49 (m, 1H), 4.83 (m, 1H), 5.15 (m, 1H). $^{13}$C NMR (CDCl$_3$): δ 19.3, 22.6, 25.0, 32.5, 34.4, 47.0, 47.7, 52.8, 56.5, 70.6, 73.4, 74.1, 78.2, 81.0, 86.2, 173.6, 175.1. See also FIGS. 12A-E.

Copolymerization of bis(2-hydroxyethyl) camphorate (BHEC) and bis(2-hydroxyethyl) terephthalate (BHET) Synthesis of Polyethylene Camphorate (PEC) (Table 3, Entry 1)

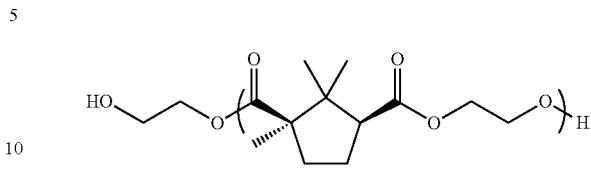

In a 50 mL round bottom flask, 1.00 g (3.47 mmol) of bis(2-hydroxyethyl) camphorate was added to 10 mg (1 mol %) of antimony oxide and a magnetic stir bar. The mixture was stirred from 175 to 240° C. under vacuum on a Schlenk line for 7 hours. After that time had elapsed, a viscous light brown polymer was obtained and removed without further purification (0.66 g, 84% yield). $^1$H NMR (CDCl$_3$): δ 0.80 (s, 3H), 1.22 (s, 3H), 1.26 (s, 3H), 1.55 (m, 1H), 1.85 (m, 1H), 2.18 (m, 1H), 2.57 (m, 1H), 2.81 (t, J=9.5 Hz, 1H), 4.31 (m, 4H). $^{13}$C NMR (CDCl$_3$): δ 21.0, 21.4, 22.3, 22.7, 24.3, 32.2, 46.5, 52.4, 55.9, 61.9, 173.3, 175.0. See also FIGS. 13A-E.

Synthesis of poly[bis(2-hydroxyethyl) camphorate-co-bis(2-hydroxyethyl) terephthalate] 90% BHEC/ 10% BHET (Table 3, Entry 2)

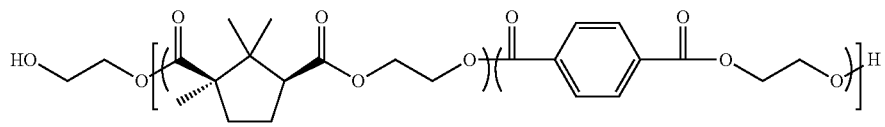

In a 50 mL round bottom flask, 765 mg (2.64 mmol) of bis(2-hydroxyethyl) camphorate were added to 75 mg (0.30 mmol) of bis(2-hydroxyethyl) terephthalate and 17 mg (2 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (0.42 g, 64% yield). $^1$H NMR (CDCl$_3$): δ 0.79 (s, 3H), 1.21 (s, 3H), 1.25 (s, 3H), 1.52 (m, 1H), 1.82 (m, 1 H), 2.17 (m, 1H), 2.56 (m, 1H), 2.80 (t, J=9.3 Hz, 1H), 4.30 (br. s., 4H), 4.45 (br. s.), 4.57 (br. s.), 4.70 (br. s.), 8.10 (s). $^{13}$C NMR (CDCl$_3$): δ 20.2, 21.3, 21.6, 22.5, 22.9, 24.5, 32.4, 34.2, 46.8, 47.2, 52.7, 53.8, 56.2, 56.5, 62.2, 129.6, 161.8, 163.2, 173.5, 175.2. See also FIGS. 14A-E.

Synthesis of poly[bis(2-hydroxyethyl) camphorate-co-bis(2-hydroxyethyl) terephthalate] 80% BHEC/ 20% BHET (Table 3, Entry 3)

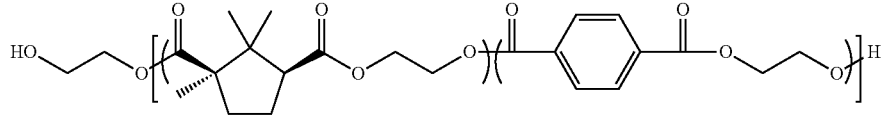

In a 50 mL round bottom flask, 1.13 g (3.93 mmol) of bis(2-hydroxyethyl) camphorate were added to 250 mg (0.983 mmol) of bis(2-hydroxyethyl) terephthalate and 28 mg (2 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (0.80 g, 74% yield). $^1$H NMR (CDCl$_3$): δ 0.88 (m, 3H), 1.20 (m, 3H), 1.24 (s, 3H), 1.51 (m, 1H), 1.82 (m, 1H), 2.17 (m, 1H), 2.56 (m, 1H), 2.80 (m, 1H), 4.30 (br. s., 4H), 4.44 (br. s.), 4.56 (br. s.), 4.70 (br. s.), 8.09 (m). $^{13}$C NMR (CDCl$_3$): δ 19.1, 20.2, 21.3, 21.6, 22.5, 22.9, 24.5, 32.4, 34.1, 46.8, 52.7, 53.8, 56.2, 61.9, 62.2, 63.0, 76.7, 77.3, 129.6, 133.7, 161.8, 162.5, 173.5, 175.2. See also FIGS. 15A-E.

Synthesis of poly[bis(2-hydroxyethyl) camphorate-co-bis(2-hydroxyethyl) terephthalate] 70% BHEC/30% BHET (Table 3, Entry 4)

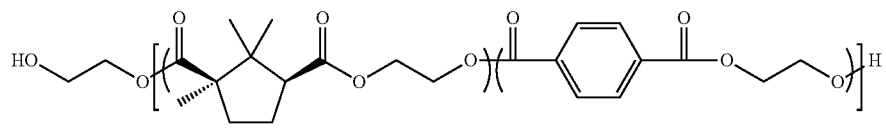

In a 50 mL round bottom flask, 1.06 g (3.67 mmol) of bis(2-hydroxyethyl) camphorate were added to 400 mg (1.57 mmol) of bis(2-hydroxyethyl) terephthalate and 15 mg (1 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (0.97 g, 86% yield). $^1$H NMR (CDCl$_3$): δ 0.78 (s, 3H), 1.20 (s, 3H), 1.24 (s, 3H), 1.51 (m, 1H), 1.82 (m, 1H), 2.17 (m, 2H), 2.56 (m, 1H), 2.80 (m, 1H), 4.30 (m, 4H), 4.44 (br. s.), 4.56 (br. s.), 4.70 (br. s.), 8.09 (m). $^{13}$C (CDCl$_3$): δ 20.2, 21.3, 21.6, 22.5, 22.9, 24.5, 32.4, 34.1, 46.8, 52.7, 53.8, 56.2, 61.9, 62.1, 63.0, 63.2, 129.6, 133.7, 142.1, 162.5, 165.4, 175.2, 176.7. See also FIGS. 16A-E.

Synthesis of poly[bis(2-hydroxyethyl) camphorate-co-bis(2-hydroxyethyl) terephthalate] 60% BHEC/40% BHET (Table 3, Entry 5)

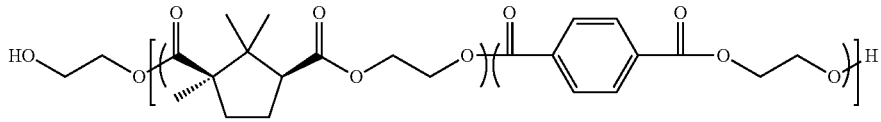

In a 50 mL round bottom flask, 700 mg (2.42 mmol) of bis(2-hydroxyethyl) camphorate were added to 412 mg (1.62 mmol) of bis(2-hydroxyethyl) terephthalate and 12 mg (1 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (0.71 g, 83% yield). $^1$H NMR (CDCl$_3$): δ 0.78 (s, 3H), 1.20 (s, 3H), 1.23 (s, 3H), 1.51 (m, 1H), 1.82 (m, 1H), 2.17 (m, 1H), 2.56 (m, 1H), 2.83 (m, 1H), 4.29 (br. s., 4H), 4.44 (br. s.), 4.56 (br. s.), 4.70 (br. s.), 8.11 (s). $^{13}$C NMR (CDCl$_3$): δ 19.2, 20.2, 21.3, 21.6, 22.8, 22.9, 24.5, 32.4, 34.2, 46.8, 52.7, 56.2, 61.9, 63.0, 129.7, 133.7, 142.8, 143.5, 162.5, 165.4. See also FIGS. 17A-E.

Synthesis of poly[bis(2-hydroxyethyl) camphorate-co-bis(2-hydroxyethyl) terephthalate] 50% BHEC/50% BHET (Table 3, Entry 6)

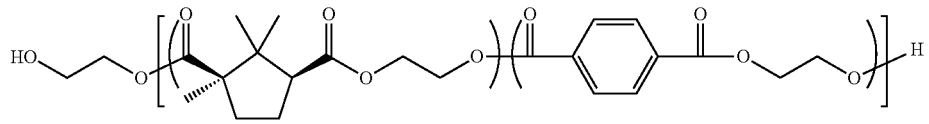

In a 50 mL round bottom flask, 1.50 g (5.2 mmol) of bis(2-hydroxyethyl) camphorate were added to 1.32 g (5.2 mmol) of bis(2-hydroxyethyl) terephthalate and 30 mg (2 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (2.07 g, 95% yield). $^1$H NMR (CDCl$_3$): δ 0.78 (br. s., 3H), 1.20 (br. s., 3H), 1.23 (br. s., 3H), 1.51 (m, 1H), 1.82 (m, 1H), 2.17 (m, 1H), 2.56 (m, 1H), 2.82 (m, 1H), 4.29 (br. s., 4H), 4.43 (br. s.), 4.56 (m), 4.70 (br. s.), 8.11 (br. s.). $^{13}$C NMR (CDCl$_3$): δ 18.8, 19.8, 21.0, 21.4, 22.2, 22.6, 24.3, 32.2, 33.9, 46.6, 52.4, 53.6, 56.0, 61.7, 62.8, 129.5, 133.4, 161.6, 162.3, 165.2, 175.0. See also FIGS. 18A-E.

Synthesis of poly[bis(2-hydroxyethyl) camphorate-co-bis(2-hydroxyethyl) terephthalate] 40% BHEC/60% BHET (Table 3, Entry 7)

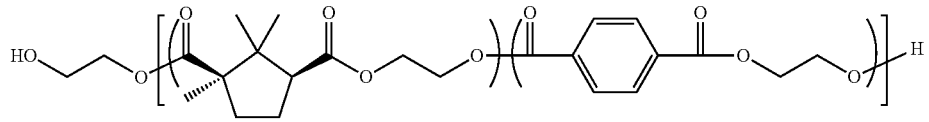

In a 50 mL round bottom flask, 1.00 g (3.47 mmol) of bis(2-hydroxyethyl) camphorate was added to 1.32 g (5.2 mmol) of bis(2-hydroxyethyl) terephthalate and 25 mg (2 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (1.60 g, 90% isolated yield). $^1$H NMR (CDCl$_3$): δ 0.77 (br. s., 3H), 1.19 (br. s., 3H), 1.23 (br. s., 3H), 1.49 (m, 1H), 1.80 (m, 1H), 2.17 (m, 1H), 2.57 (m, 1H), 2.82 (m, 1H), 4.28 (br. s., 4H), 4.43 (m), 4.55 (br. s.), 4.69 (s), 8.10 (m). $^{13}$C NMR (CDCl$_3$): δ 18.6, 19.9, 21.0, 21.3, 22.3, 22.6, 24.2, 32.2, 33.9, 46.6, 52.4, 53.6, 56.0, 61.7, 62.7, 129.5, 133.4, 162.4, 165.2. See also FIGS. 19A-E.

Synthesis of poly[bis(2-hydroxyethyl) camphorate-co-bis(2-hydroxyethyl) terephthalate] 30% BHEC/70% BHET (Table 3, Entry 8)

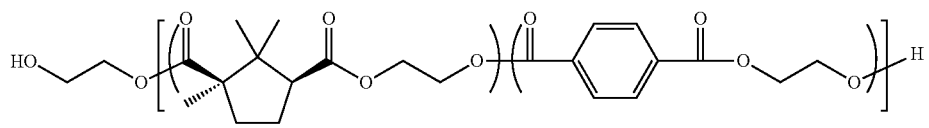

In a 50 mL round bottom flask, 750 mg (2.60 mmol) of bis(2-hydroxyethyl) camphorate were added to 1.54 g (6.06 mmol) of bis(2-hydroxyethyl) terephthalate and 25 mg (2 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (1.70 g, 97% isolated yield). $^1$H NMR (CDCl$_3$): δ 0.77 (br. s., 3H), 1.19 (br. s., 3H), 1.22 (br. s., 3H), 1.50 (m, 1H), 1.82 (m, 1H), 2.17 (m, 1H), 2.53 (m, 1H), 2.80 (m, 1H), 4.28 (m, 4H), 4.42 (m), 4.55 (m), 4.69 (br. s.), 8.10 (m). $^{13}$C NMR (CDCl$_3$ and TFA-d): δ 22.3, 23.6, 25.4, 33.4, 48.7, 49.2, 54.2, 57.8, 64.2, 65.0, 70.3, 131.2, 134.6, 168.7. See also FIGS. 20A-E.

Synthesis of poly[bis(2-hydroxyethyl) camphorate-co-bis(2-hydroxyethyl) terephthalate] 20% BHEC/80% BHET (Table 3, Entry 9)

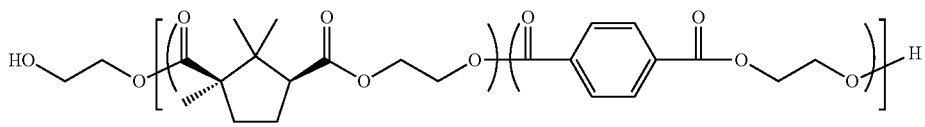

In a 50 mL round bottom flask, 750 mg (2.60 mmol) of bis(2-hydroxyethyl) camphorate were added to 2.65 g (10.43 mmol) of bis(2-hydroxyethyl) terephthalate and 38 mg (1 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (2.59 g, 99% isolated yield). $^1$H NMR (CDCl$_3$ and TFA-d): δ 0.77 (br. s., 3H), 1.19 (s, 3H), 1.22 (s, 3H), 1.51 (m, 1H), 1.81 (m, 1H), 2.17 (m, 1H), 2.55 (m, 1H), 2.82 (m, 1H), 4.28 (m, 4H), 4.51 (m), 4.55 (m), 4.69 (br. s.), 8.10 (m). $^{13}$C (CDCl$_3$ and TFA-d): δ 22.5, 23.7, 26.8, 31.2, 34.8, 66.5, 67.2, 71.7, 132.6, 132.7, 136.0, 170.2. See also FIGS. 21A-E.

Synthesis of poly[bis(2-hydroxyethyl) camphorate-co-bis(2-hydroxyethyl) terephthalate] 10% BHEC/90% BHET (Table 3, Entry 10)

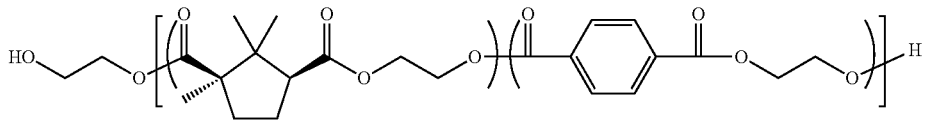

In a 50 mL round bottom flask, 400 mg (1.39 mmol) of bis(2-hydroxyethyl) camphorate were added to 3.17 g (12.48 mmol) of bis(2-hydroxyethyl) terephthalate and 40 mg (1 mol %) of antimony oxide with a magnetic stir bar. The mixture was stirred from 200 to 240° C. under vacuum on a Schlenk line for 7 hours. After that time had elapsed, a viscous light brown polymer was obtained and removed without further purification (2.83 g, 99% yield). $^1$H NMR (CDCl$_3$ and TFA-d): δ 0.81 (s), 1.19 (s), 1.23 (s), 1.58 (m), 1.89 (m), 2.17 (m), 2.54 (m), 2.94 (m), 4.12 (s), 4.54-4.80 (m, 4H), 8.13 (m, 4H). $^{13}$C NMR (CDCl$_3$ and TFA-d): δ 13.4, 43.9, 46.8, 51.9, 66.5, 67.2, 71.7, 132.6, 132.7, 136.0, 170.2. See also FIGS. 22A-E.

Synthesis of poly[bis(2-hydroxyethyl) terephthalate] (PET) (Table 3, Entry 11)

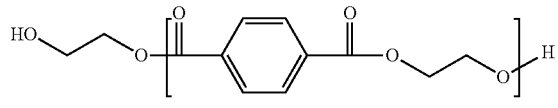

In a 50 mL round bottom flask, 2.00 g (7.87 mmol) of bis(2-hydroxyethyl) terephthalate, 23 mg (1 mol %) of antimony oxide, and a magnetic stir bar were combined. The mixture was stirred from 200 to 240° C. under vacuum on a Schlenk line for 7 hours. After that time had elapsed, a viscous light brown polymer was obtained and removed without further purification (1.73 g, 99% yield). $^1$H NMR (CDCl$_3$ and TFA-d): δ 4.83 (s, 4H), 8.17 (m, 4H). $^{13}$C NMR (CDCl$_3$ and TFA-d): δ 65.2, 131.3, 134.6, 169.3. See also FIGS. 23A-E.

Comparison of Polymers

Figure 4A:
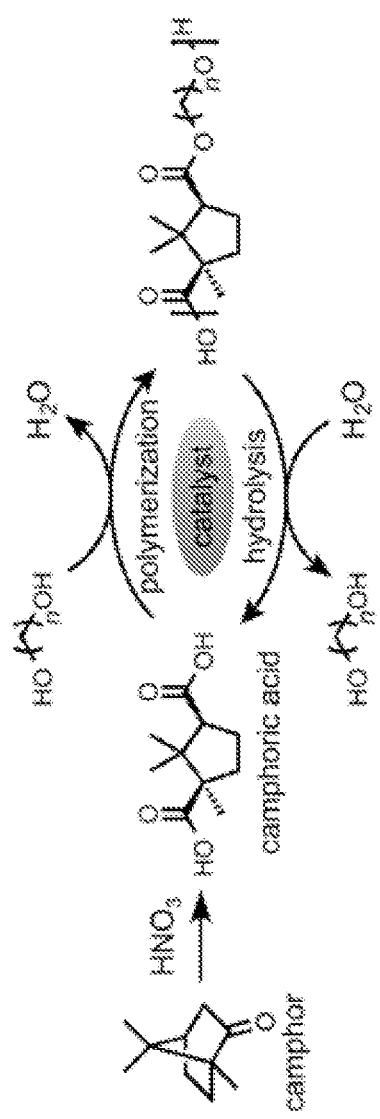
FIGS. 4A-4B show representative synthetic schemes.

Disclosed herein are exemplary polyesters made from a renewable diacids, camphoric acid, and α,ω-alkanediols or other renewable diols prepared using conditions described herein and shown in Scheme 1 (FIG. 4A). In the following examples, camphoric acid was copolymerized with various diols, including the homologous linear alkanediols HO(CH$_2$)$_n$OH, with n=2, 3, 4, 5, and 6 to afford polyalkylene camphorate polyesters. Table 1 displays a summary of the polymerization results, including biobased content (%), molecular weight data, and thermal properties of the obtained polymers. In particular, Table 1 shows polymerization and characterization of polyalkylene camphorates from linear diols (Entries 1-6) and camphorate polyesters derived from erythritan (Entry 7) and isosorbide (Entry 8).

TABLE 1

| Entry | Polymer from camphoric acid + diol | Catalyst | Yield (%) | Biobased Content (%)[b] |
|---|---|---|---|---|
| 1 | polyethylene camphorate | Zn(OAc)$_2$ + Sb$_2$O$_3$ | 75 | 73.5 |
| 2 | polyethylene camphorate | p-TSA | 84 | 73.5 |
| 3 | polypropylene camphorate | p-TSA | 75 | 69.2 |
| 4 | polybutylene camphorate | p-TSA | 71 | 65.4 |
| 5 | polypentylene camphorate | p-TSA | 73 | 61.9 |
| 6 | polyhexylene camphorate | p-TSA | 96 | 58.9 |
| 7 | erythritan camphorate polyester | Zn(OAc)$_2$ + Sb$_2$O$_3$ | 73 | 100 |
| 8 | isosorbide camphorate polyester | p-TSA | 98 | 100 |

TABLE 1-continued

| Entry | Polymer from camphoric acid + diol | $M_n$ (Da)[c] | $M_w$ (Da)[c] | Đ [c] | Tg (° C.)[d] | $T_5$ (° C.)[e] |
|---|---|---|---|---|---|---|
| 1 | [structure: camphoryl diester with ethylene glycol linker] | 18,700 | 75,700 | 4.0 | 51 | 331 |
| 2 | [structure: camphoryl diester with ethylene glycol linker] | 20,200 | 60,800 | 3.0 | 44 | 368 |
| 3 | [structure: camphoryl diester with propylene glycol linker] | 7,700 | 22,800 | 3.0 | 38 | 326 |
| 4 | [structure: camphoryl diester with butylene glycol linker] | 7,300 | 19,600 | 2.7 | 25 | 322 |
| 5 | [structure: camphoryl diester with pentylene glycol linker] | 8,300 | 24,500 | 2.9 | −1 | 352 |
| 6 | [structure: camphoryl diester with hexylene glycol linker] | 8,000 | 35,800 | 4.4 | −16 | 353 |
| 7 | [structure: camphoryl diester with tetrahydrofuran diol linker] | 9,000 | 25,000 | 2.8 | 100 | 304 |
| 8 | [structure: camphoryl diester with isosorbide linker] | 6,900 | 42,000 | 6.1 | 125 | 355 |

[a] Polymerization conducted at 180° C. under nitrogen for 16 hours, followed by a temperature ramp over 12 hours to 230° C. under dynamic vacuum.
[b] Calculated according to (166.22)/(166.22 + (diol$_{FW}$-2)), where 166.22 represents the atoms contributed by camphoryl and (diol$_{FW}$-2) represents the formula weight of the α,ω-diol minus the removed hydrogen atoms.
[c] Gel permeation chromatography (GPC) in hexafluoroisopropanol (HFIP) at 40° C. vs polymethylmethacrylate standards.
[d] Determined by DSC.
[e] Temperature at which 5% mass loss was observed, determined by thermogravimetric analysis (TGA).

During polymerization, a slight excess (1.2 equivalents) of diol was added to ensure its full incorporation into the initially formed oligomers. After 16 hours at 180° C. under 1 atm of nitrogen, vacuum was applied for 12 hours during a temperature ramp to 230° C.; this protocol was designed to remove water and any excess diol, thus increasing the molecular weight. The Brønsted acid catalyst p-toluene sulfonic acid (p-TSA, 4 mol %) proved effective for most diols, showing efficacy for both initial esterification and subsequent transesterification. Additionally, a sequential catalyst combination of zinc acetate (2 mol %) and antimony oxide (1 mol %) was investigated (Table 1, Entries 1 and 7). Zinc acetate was first added for the esterification stage at 180° C. under nitrogen, leading to the formation of oligomers. Prior to the temperature ramp and vacuum, antimony oxide was added because it is a known high-temperature (>200° C.) transesterification catalyst. This dual catalyst technique proved effective for camphoric acid/ethylene glycol (Table 1, Entry 1), but p-TSA afforded a marginally greater yield and number-average molecular weight (Mn) (Table 1, Entry 2).

Figure 2:
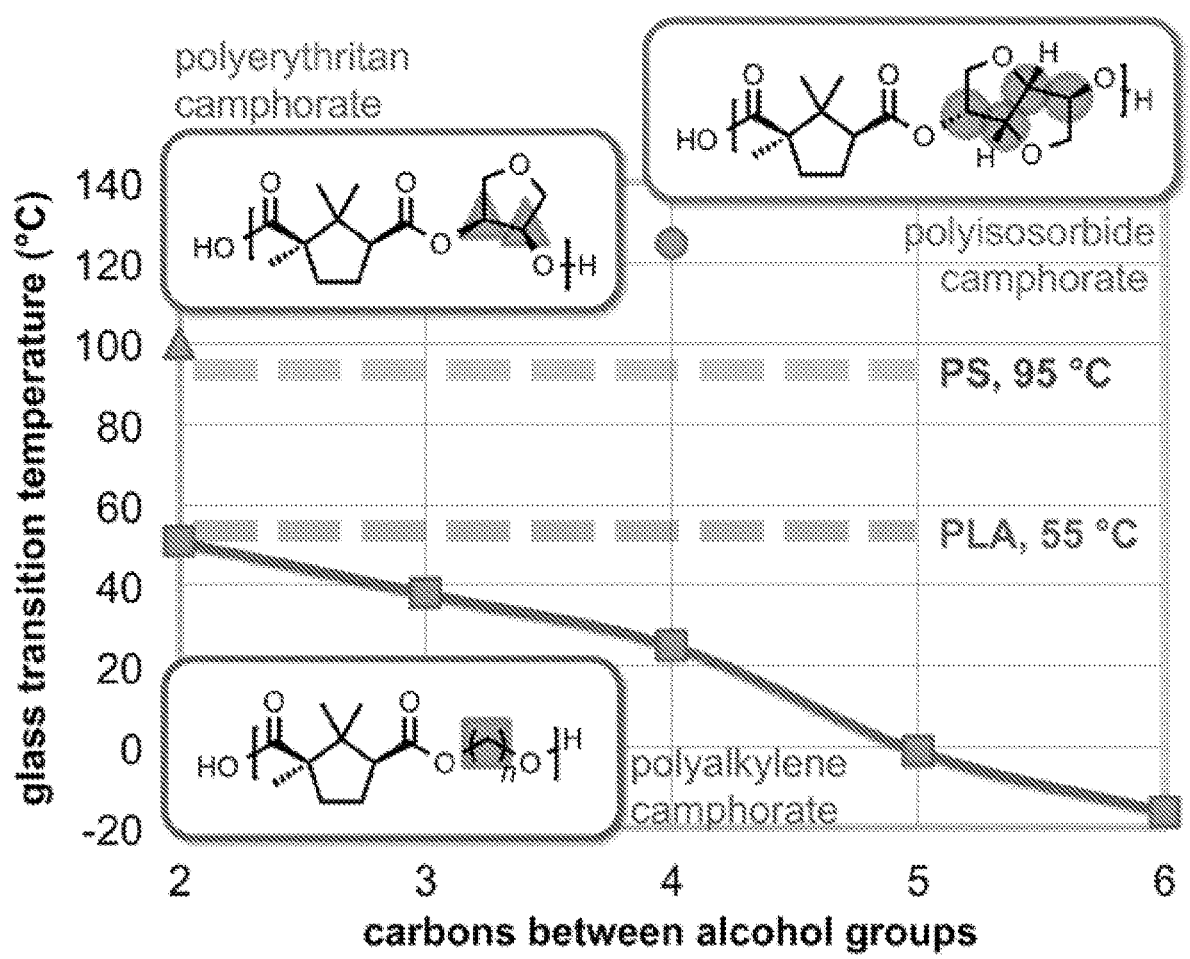
FIG. 2 shows representative glass transition temperature data obtained for a representative disclosed polyester versus the number of carbons between the alcohol groups of the constituent diol.

For the linear diols of Table 1 (Entries 1-6), moderate to good molecular weights are obtained, with Mn values ranging from 7,300 to 20,200 Da and Mw values (weight-average molecular weight) ranging from 19,600 to 75,700 Da. Thus, dispersity (Đ) values were somewhat high and ranged from 2.7 to 4.4. Polyethylene camphorate (PEC) exhibits the highest molecular weight (Table 1, Entries 1 and 2) probably because ethylene glycol has the lowest boiling point among the linear diols; thus, excess ethylene glycol is most easily removed and the ideal 1:1 diacid:diol stoichiometry is most readily achieved. Longer diols afforded polymers with lower molecular weights (Mn=7,300-8,300 Da), even with the aforementioned dual catalyst technique (Mn=2,800-4,600 Da, see the ESI). A summary of GPC results for the dual catalyst method with longer diols can be found in Table 2.

erythritan (Table 1, Entry 7) boosts the $T_g$ of polyerythritan camphorate (FIG. 2) to 100° C.-well above that provided by the comparably sized, 1,2-diol of ethylene glycol ($T_g=51°$ C.). Isosorbide is another renewable cyclic diol monomer derived from glucose that has already gained considerable attention from polymer chemists, particularly as a potential replacement for bisphenol A in epoxy resins and polycarbonates (Refs. 54-56). The rigid bicyclic isosorbide (Table 1, Entry 8) confers an even higher $T_g$ value of 125° C. to polyisosorbide camphorate (FIG. 2), the highest of Table 1. These glass transition temperatures compare favorably with those of polystyrene (PS, $T_g=95°$ C.) and atactic polymethylmethacrylate (PMMA, $T_g=105°$ C.). Although erythritan

TABLE 2

| Entry | Polymers | Catalysts | $M_n^b$ (Da) | $M_w^b$ (Da) | Đ $^b$ |
|---|---|---|---|---|---|
| 1 | [structure] | Zn(OAC)$_2$ Sb$_2$O$_3$ | 4,200 | 13,600 | 3.2 |
| 2 | [structure] | Zn(OAC)$_2$ Sb$_2$O$_3$ | 4,600 | 16,700 | 3.6 |
| 3 | [structure] | Zn(OAC)$_2$ Sb$_2$O$_3$ | 2,800 | 7,200 | 2.6 |

$^a$ Polymerizations conducted at 180° C. under nitrogen for 16 hours, followed by a temperature ramp over 12 hours to 230° C. under dynamic vacuum. Catalysts: Zn(OAC)$_2$ (2 mol %) and Sb$_2$O$_3$ (1 mol %, added after first stage) for each entry.
$^b$ Gel Permeation Chromatography (GPC) in hexafluoroisopropanol (HFIP) at 40° C. vs polymethylmethacrylate standards.

Table 1 provides a summary of the thermal properties for these camphoric acid/linear diol polyesters (Entries 1-6) as measured by differential scanning calorimetry (DSC) and thermogravimetric analysis ($T_gA$). The highest glass transition temperature ($T_g$) obtained in this series belongs to PEC (from ethylene glycol, Entry 1, 51° C.). This $T_g$ is comparable to that of polylactic acid ($T_g$ of 55° C.), and thus, PEC has the potential to mimic PLA. Noticeably, $T_g$ decreases as the alkylene connector length (n) increases (see FIG. 2). The observed range was 51° C. (n=2) to −16° C. (n=6). These polymers are apparently not crystalline, since no melting temperatures were detected by DSC. Note that camphoric acid is unsymmetrical and thus, should be incorporated with random regiochemistry into the main-chain. NMR analysis is consistent with a regioirregular structure. Hence, the polymers lack long-range stereochemical or conformational order typically necessary for crystallinity. Finally, Table 1 summarizes the T5 values for these polyesters, which is the temperature at which 5% mass loss occurs according to $T_gA$ under nitrogen. The T5 decomposition temperatures range from 322° C. to 368° C.

In order to increase the glass transition temperature of camphoric acid-based polyesters, other biobased, non-linear diols were investigated: erythritan and isosorbide. Erythritan is derived from erythritol by dehydration and thus, is also named cis-1,4-anhydroerythritol. Erythritol, in turn, is an inexpensive, naturally-occurring tetraol derived in large scale from glucose, employed mainly as a low calorie sweetener (Refs. 52, 53). The rigid five membered ring of and isosorbide possess more sterically encumbered secondary alcohols, the obtained yields and molecular weights were similar to those of the long linear diols of Table 1.

Molecular weight and dispersity parameters of diacid/diol copolymerizations are sensitive to slight deviations of the ideal 1:1 stoichiometry. This prompted us to pursue a corrective strategy applied to PET production, wherein terephthalic acid is first converted to bis(hydroxyethyl) terephthalate (BHET). Accordingly, bis(hydroxyethyl) camphorate (BHEC) was synthesized through Fischer esterification of camphoric acid with an excess of ethylene glycol under acidic conditions. Subsequent to isolation, this monomer was polymerized using catalytic antimony oxide (Sb$_2$O$_3$, 1 mol %) under high vacuum, thereby removing ethylene glycol as the small molecule by-product of transesterification. The procedure afforded relatively high molecular weight polyethylene camphorate (PEC) with Mn=23,800, an almost ideal dispersity of 2.3, and a $T_g$ value of 41° C. (Table 3, Entry 1).

The present examples have targeted camphoric acid, a fully biobased diacid, as a potential mimic of fossil fuel-based terephthalic acid for incorporation into the PET structure to augment its biobased content. In some examples, there has been the incremental replacement of the terephthalic acid of PET with camphoric acid via the copolymerization strategy described in Table 3.

Bis(hydroxyethyl) camphorate (BHEC) and bis(hydroxyethyl) terephthalate (BHET) were copolymerized with varying feed fractions via transesterification with antimony oxide (1 mol %). The BHEC incorporation fraction is consistently lower than its feed fraction, validating the conclusion that BHEC is harder to polymerize than BHET. A reactivity ratio analysis (FIG. 3; see also the ESI) revealed that $r_{BHEC}$=0.47 and $r_{BHET}$=2.26 (RMS error=2.67). Without wishing to be bound by a particular theory, it is possible that steric encumbrance can hinder the reactivity of BHEC, compared to BHET. This comports with reported small molecule esterification rates, which decrease with increasing steric encumbrance (quantified by a van der Waals radii parameter, v) from benzoic acid (aryl; v=0.57) to isobutyric acid (2°; v=0.76) to pivalic acid (3°; v=1.24).

Figure 4B:
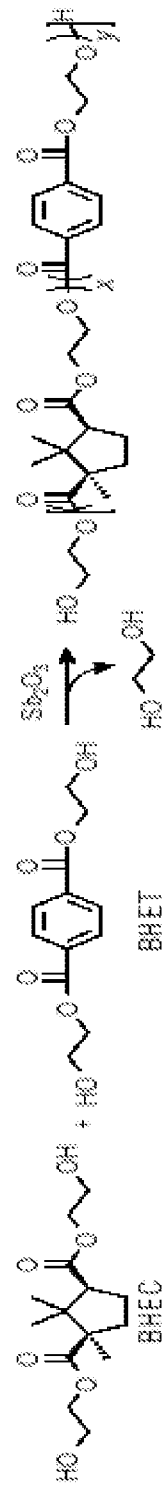
Figure 5A:
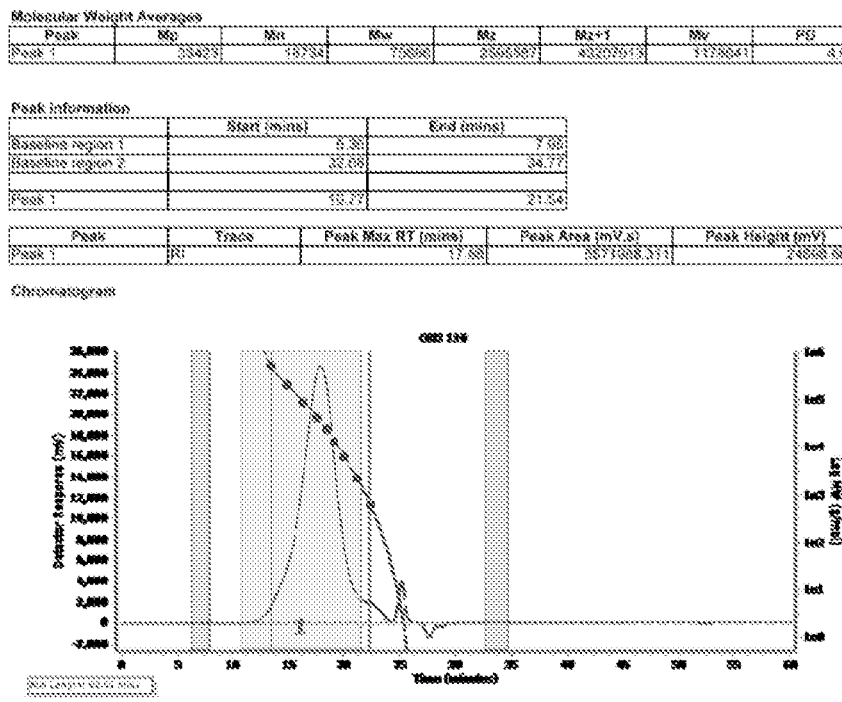
FIGS. 5A-E show characterization of polyethylene camphorate.
Figure 5B:
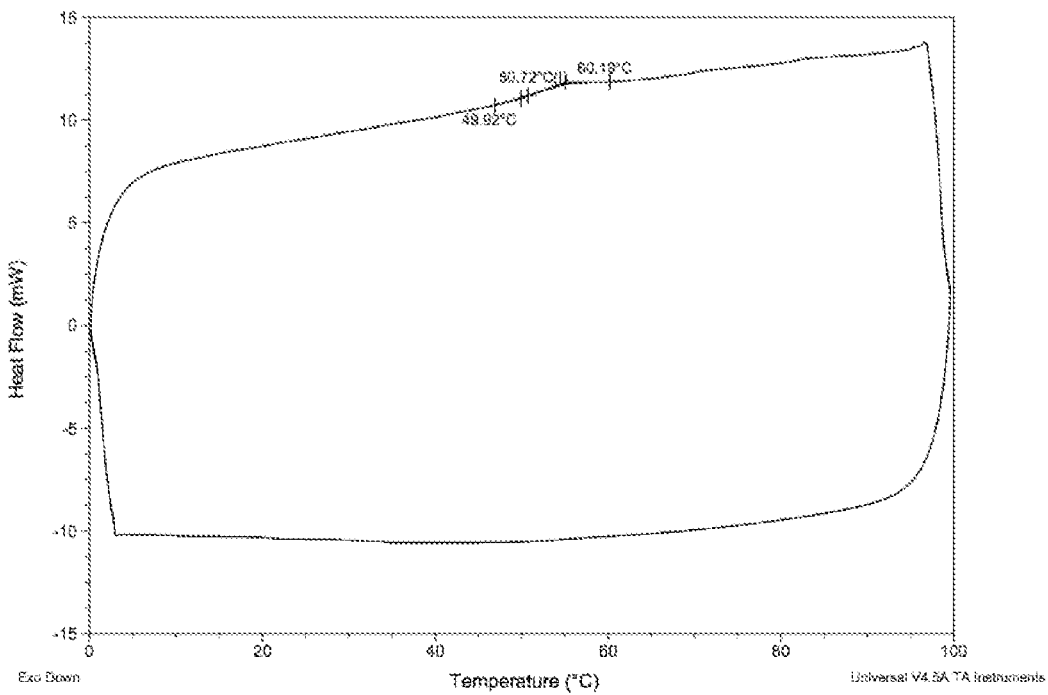
Figure 5C:
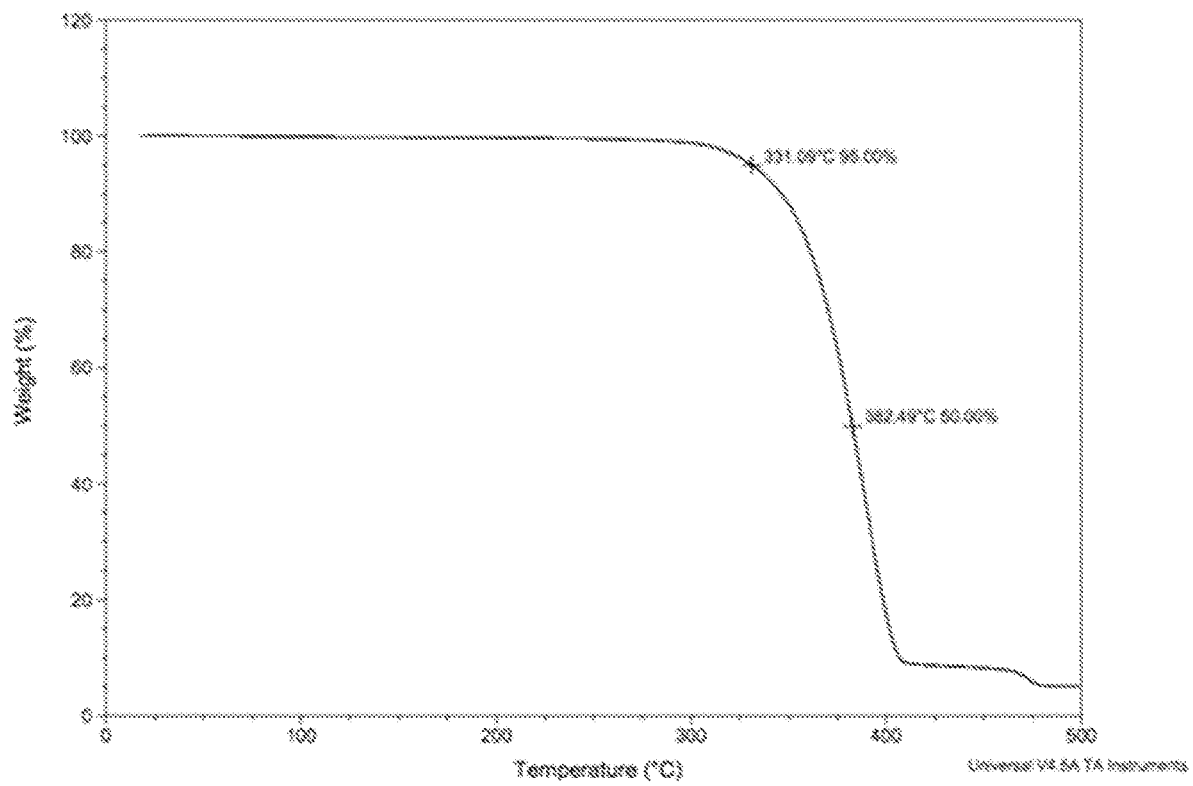
Figure 5D:
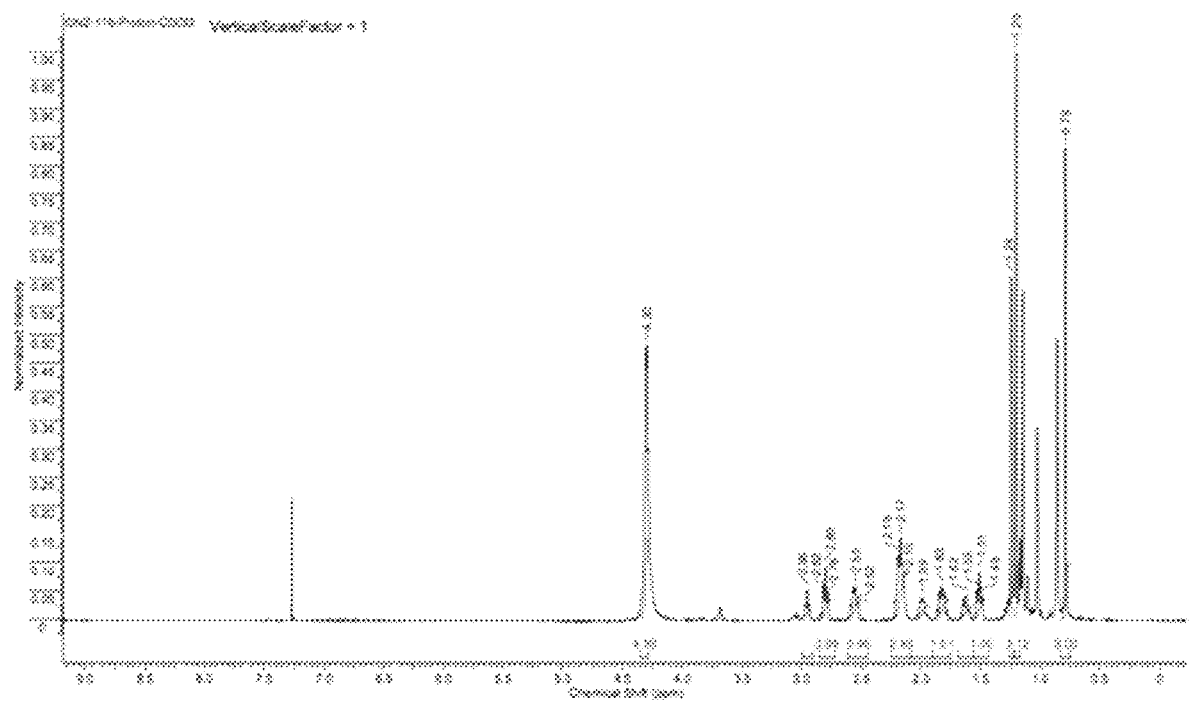
Figure 5E:
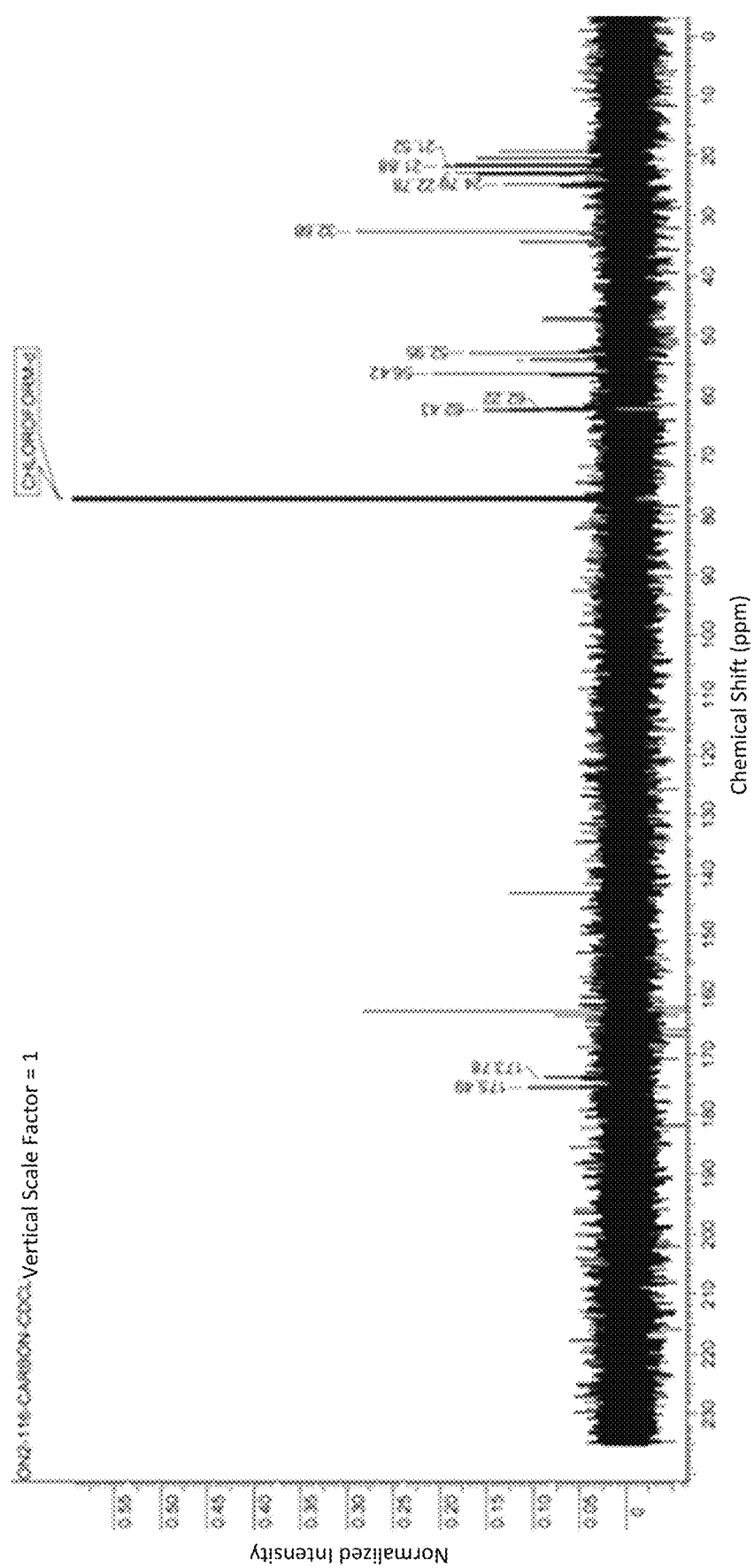
Figure 6A:
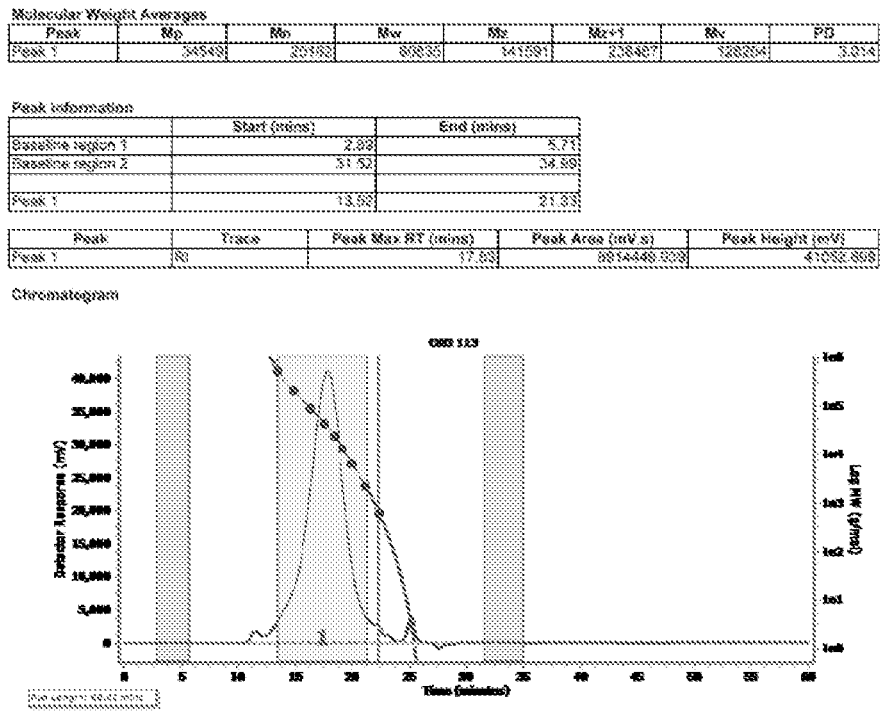
FIGS. 6A-E show characterization of polyethylene camphorate (dual catalyst).
Figure 6B:
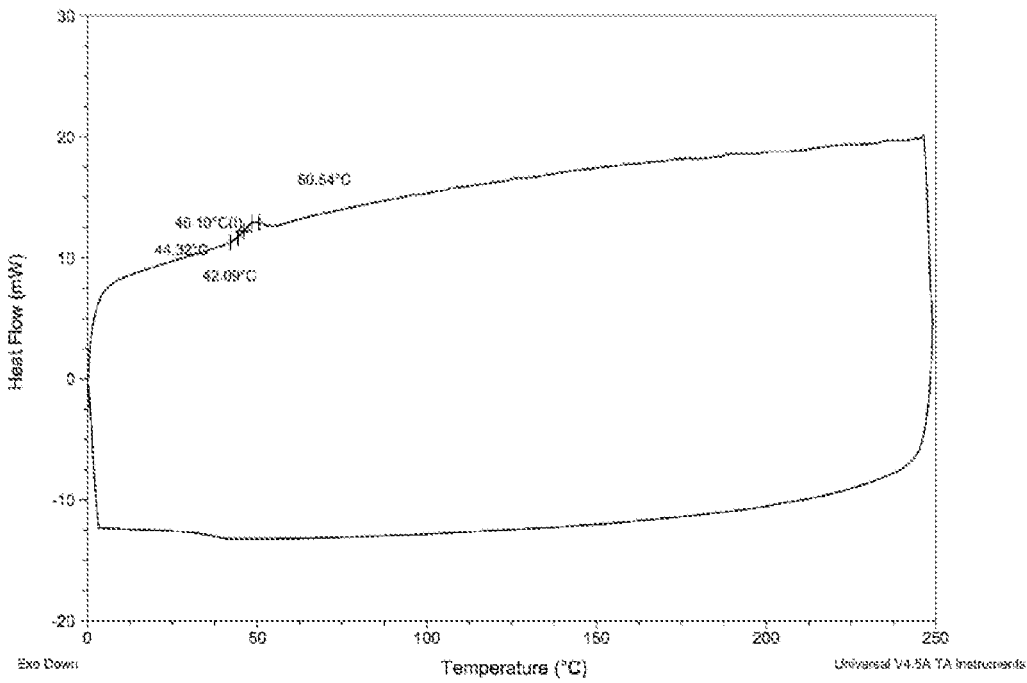
Figure 6C:
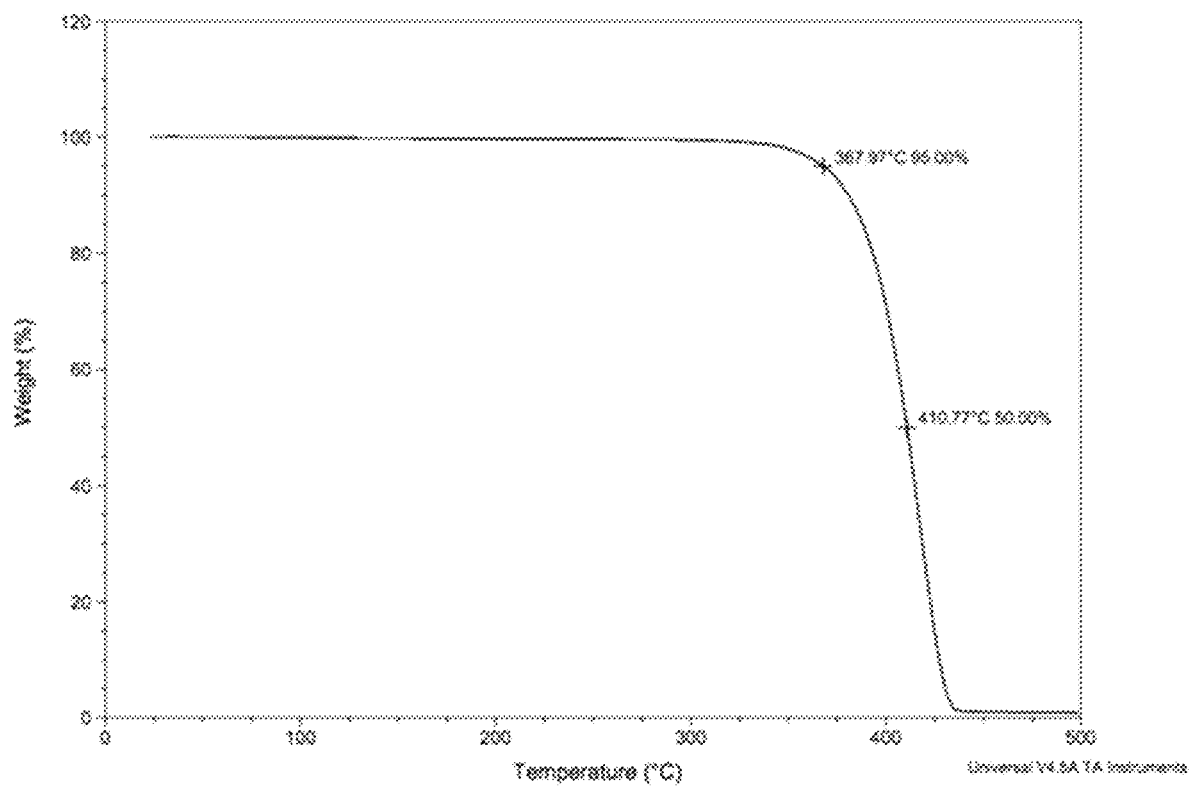
Figure 6D:
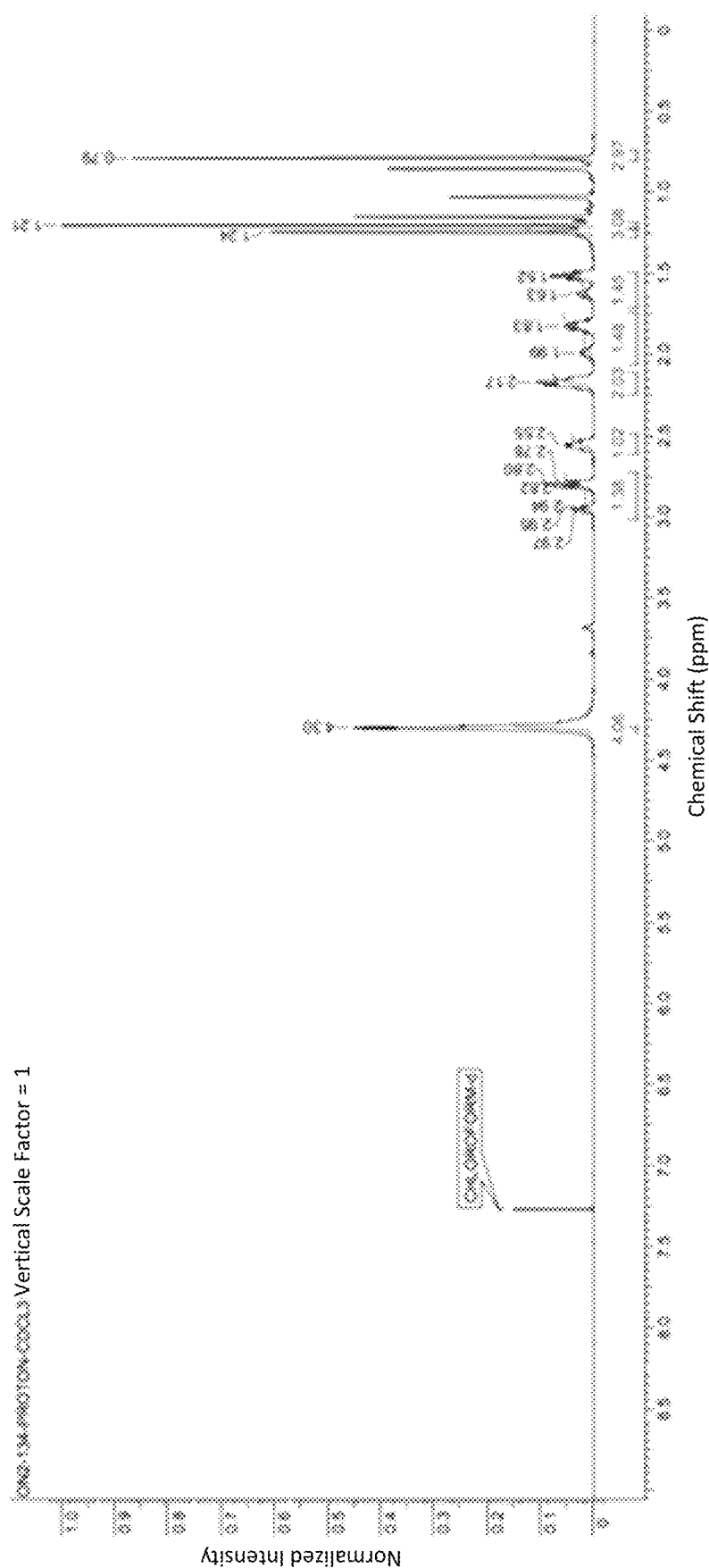
Figure 6E:
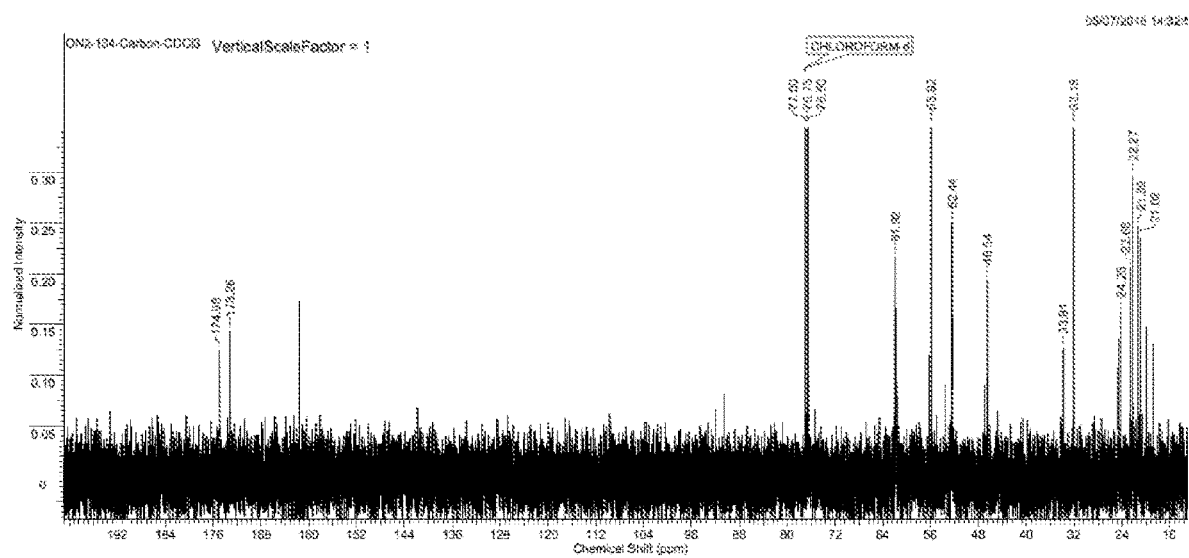
Figure 7A:
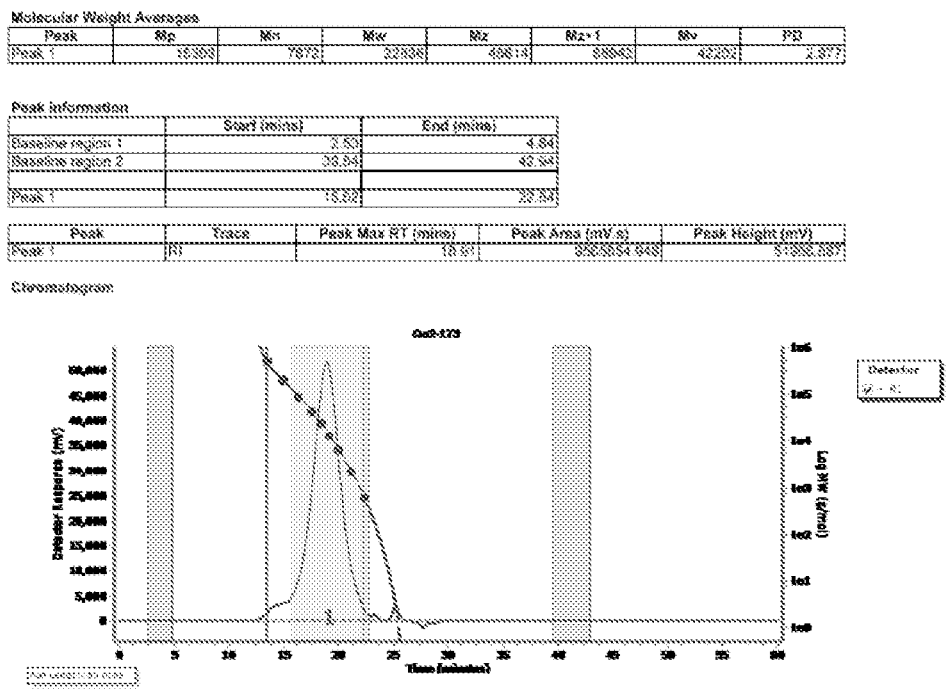
FIGS. 7A-E show characterization of polypropylene camphorate.
Figure 7B:
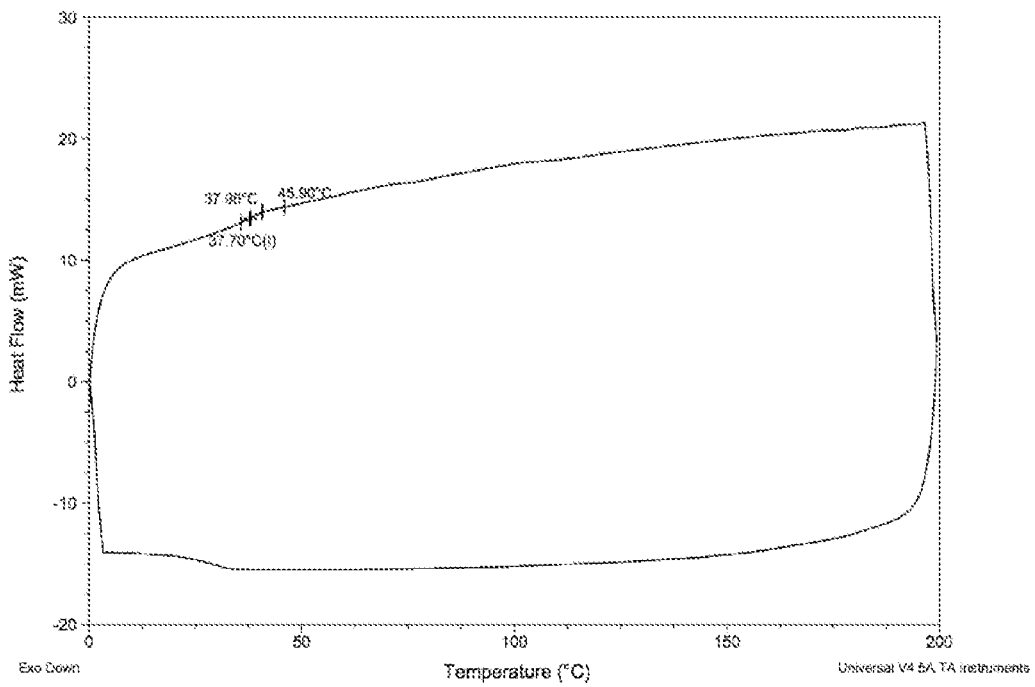
Figure 7C:
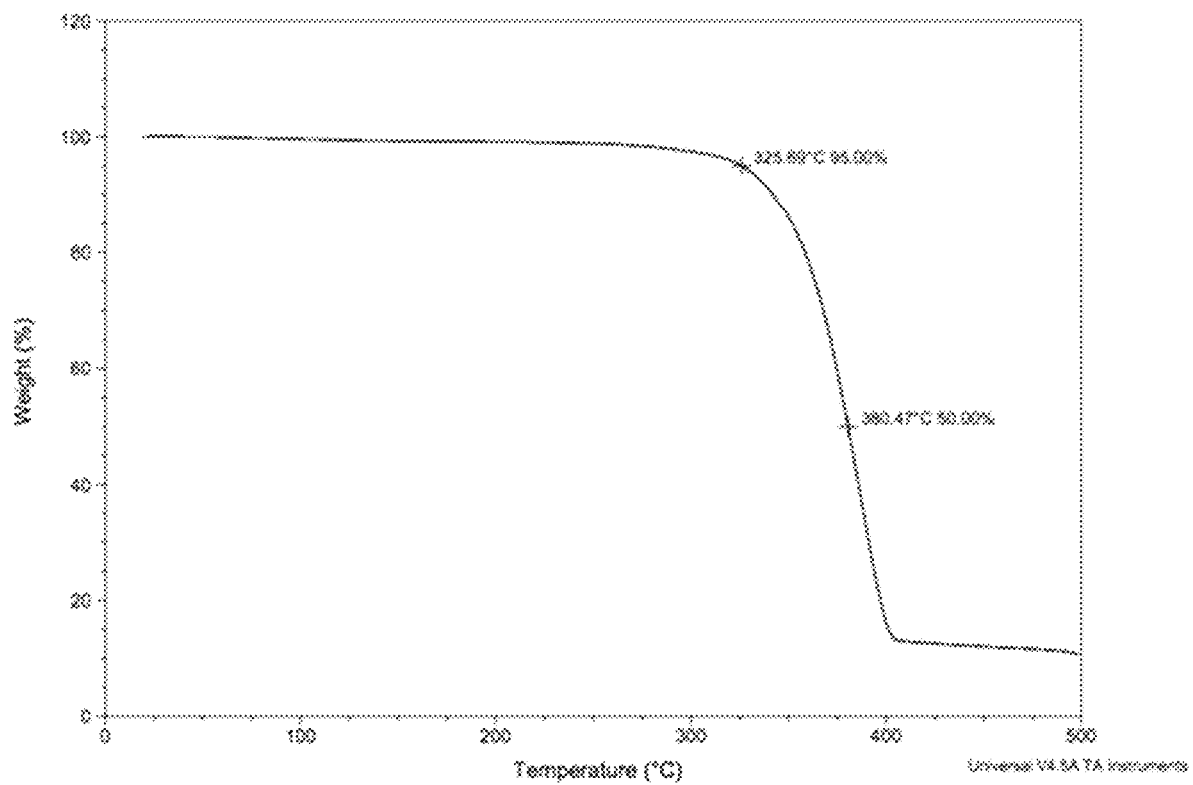
Figure 7D:
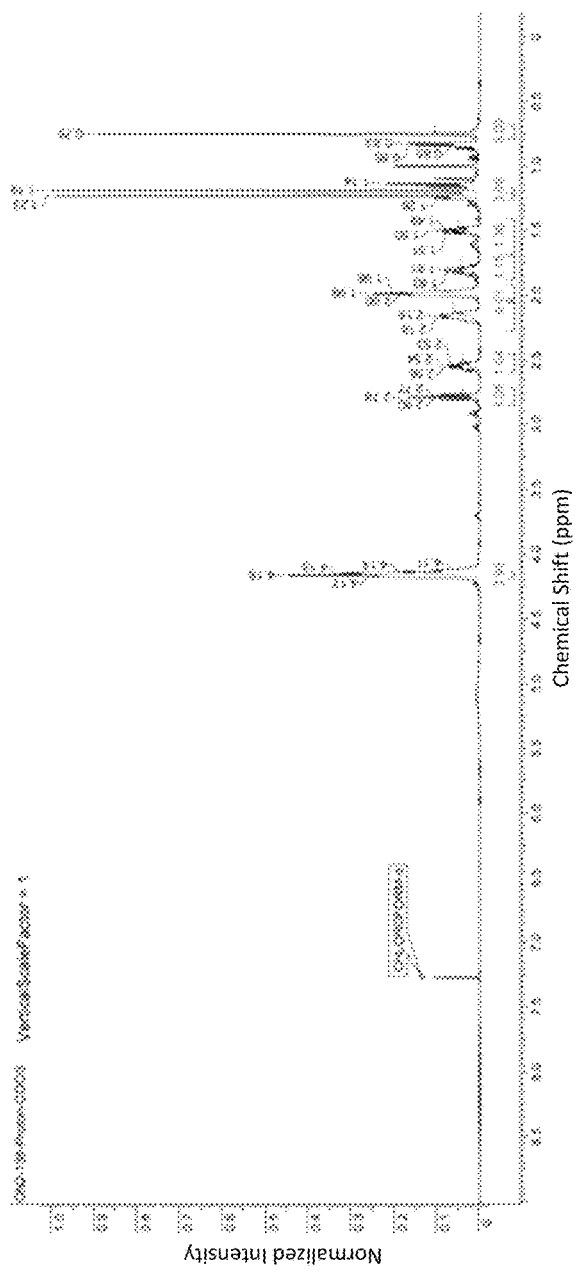
Figure 7E:
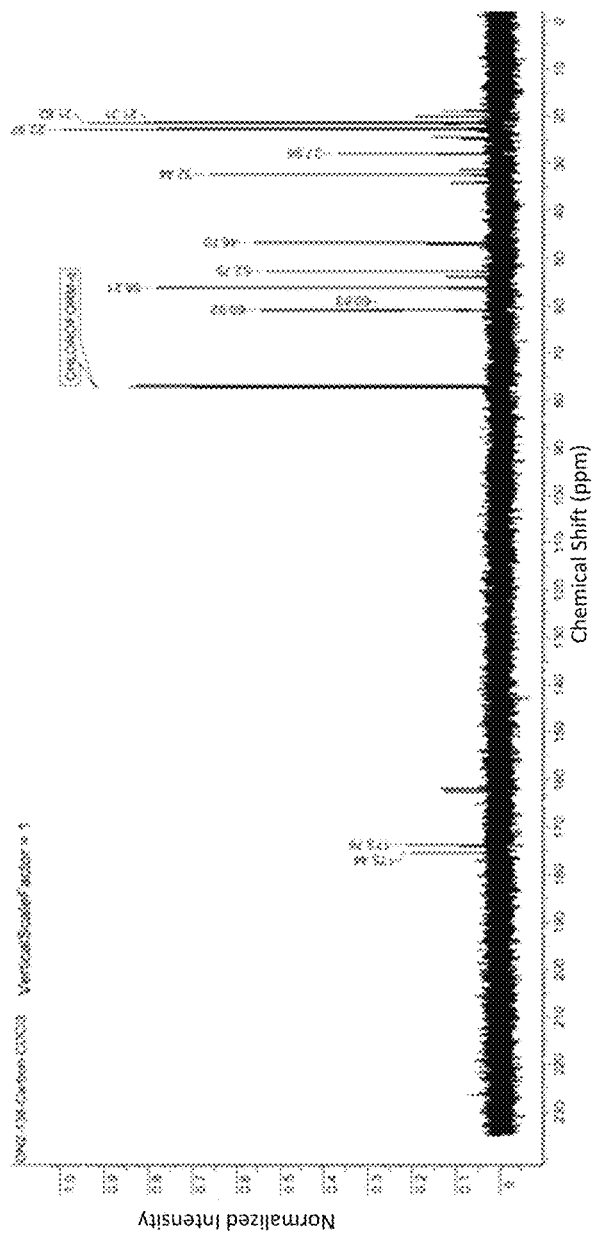
Figure 8A:
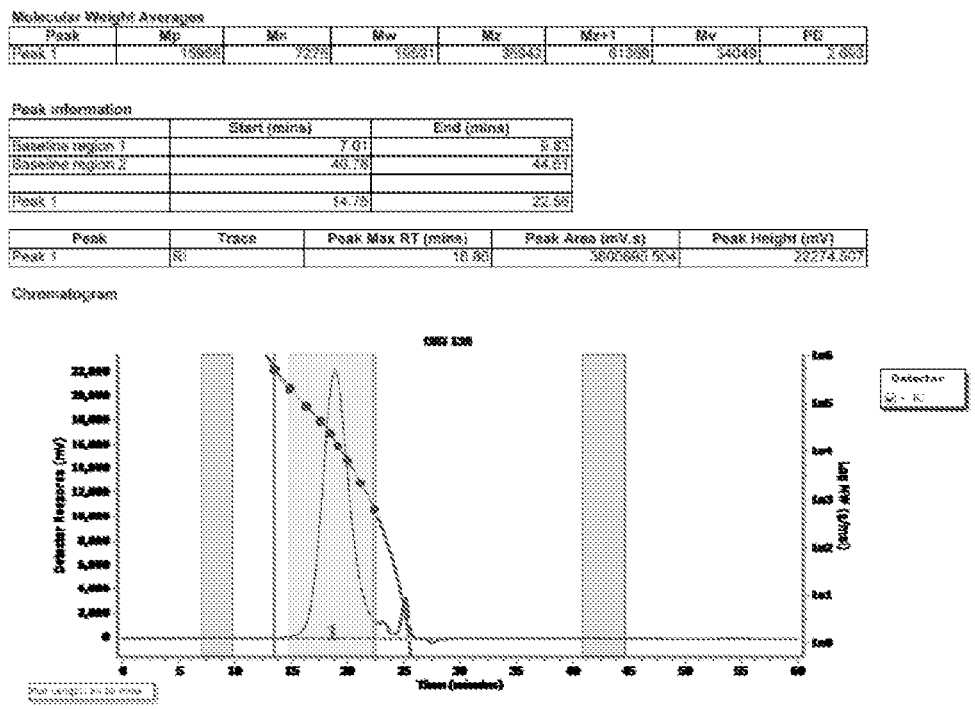
FIGS. 8A-E show characterization of polybutylene camphorate.
Figure 8B:
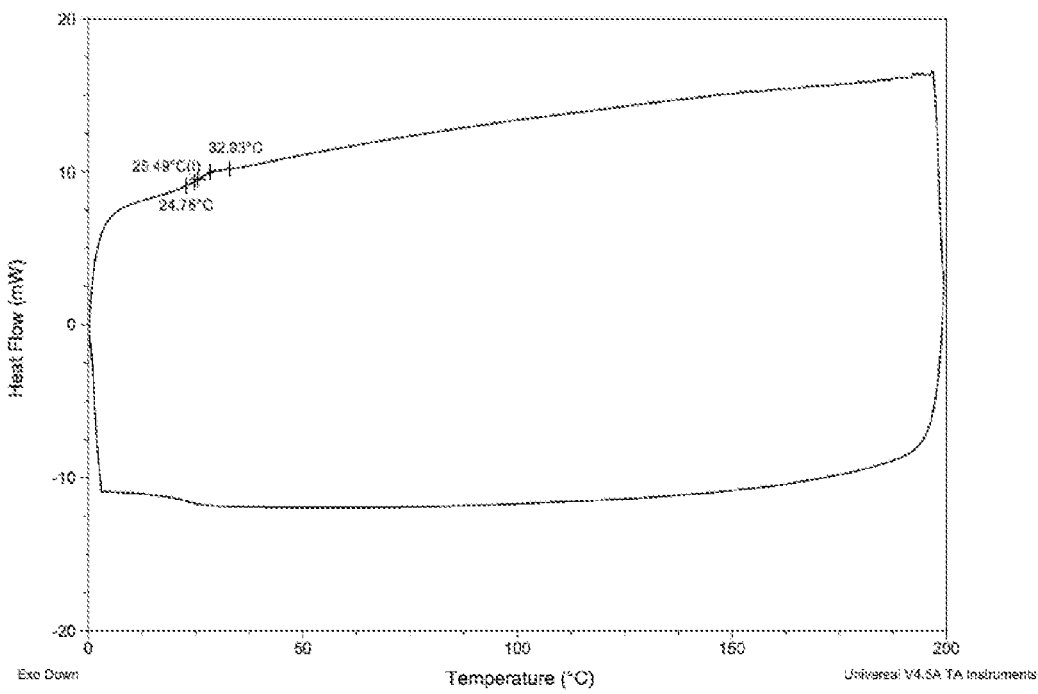
Figure 8C:
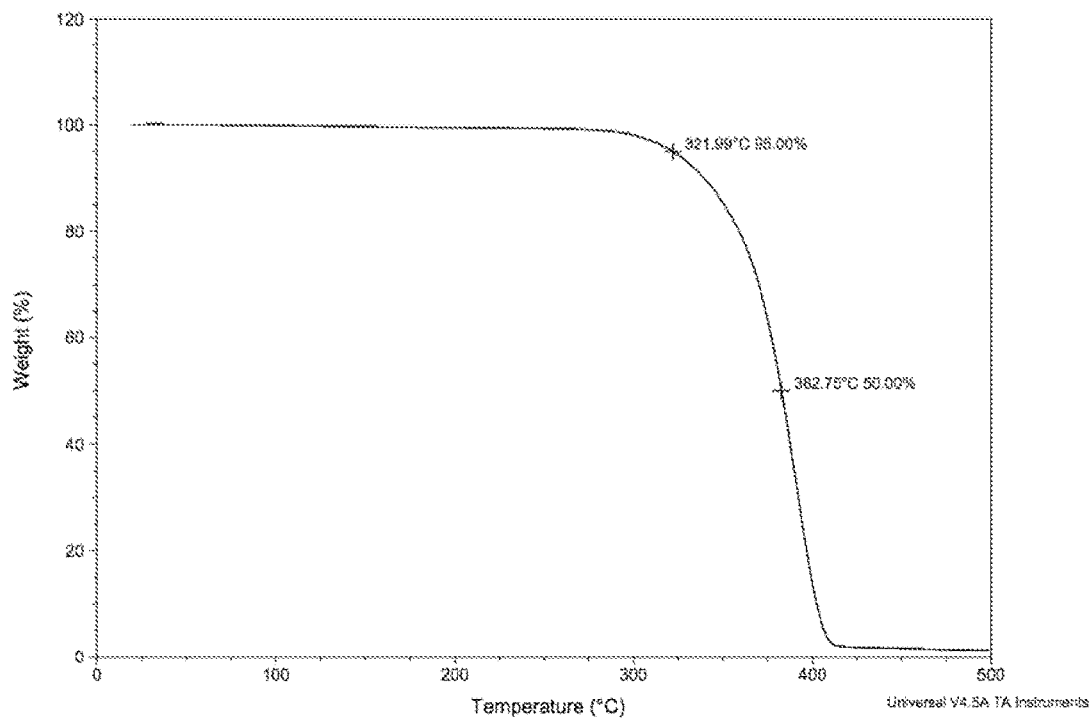
Figure 8D:
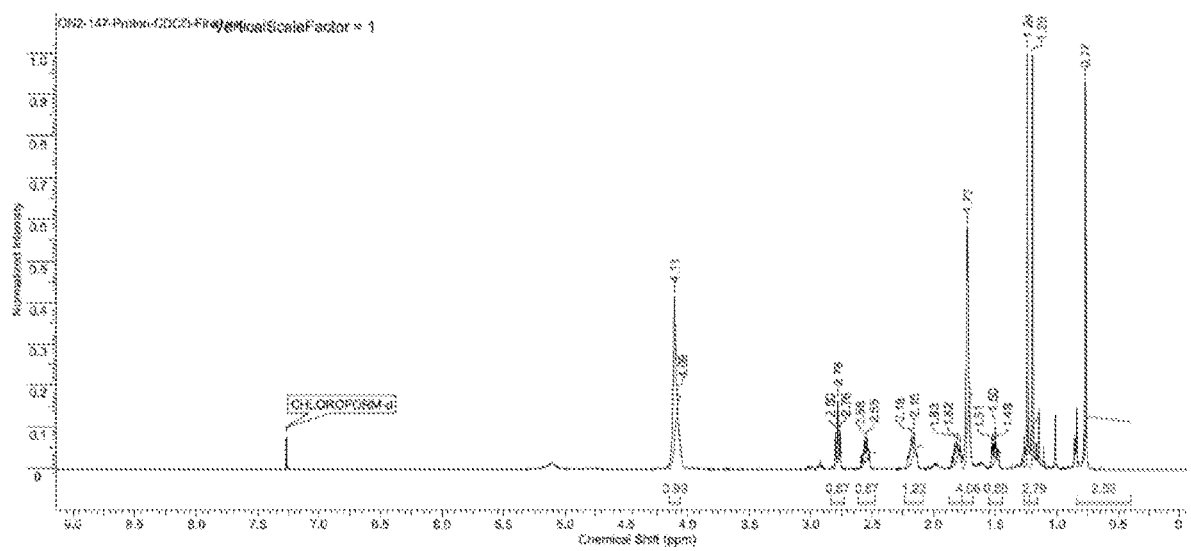
Figure 8E:
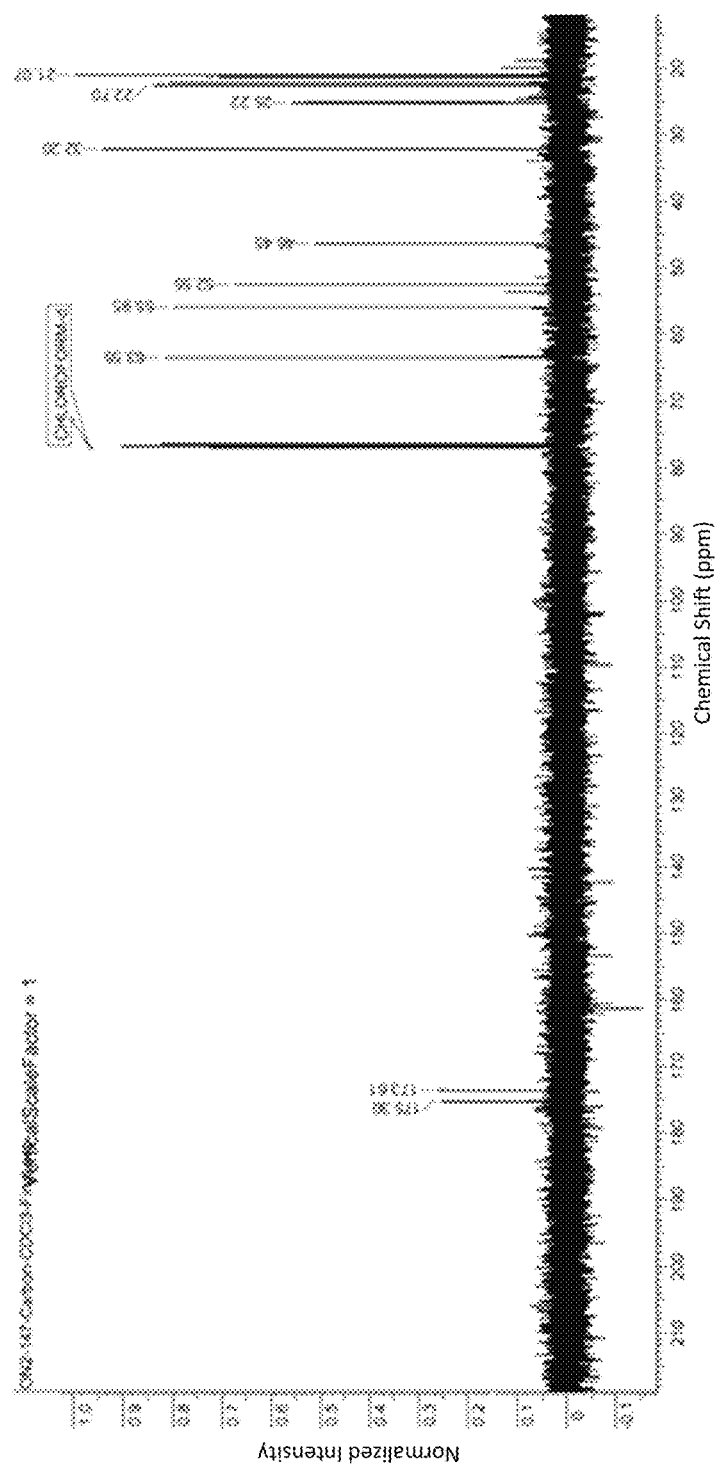
Figure 9A:
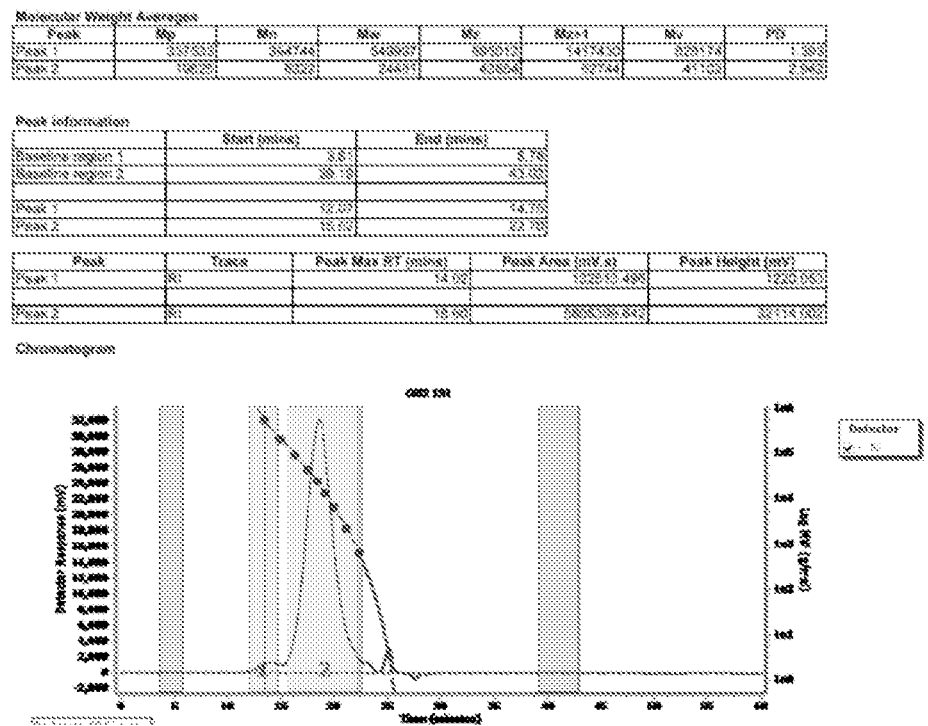
FIGS. 9A-E show characterization of polypentylene camphorate.
Figure 9B:
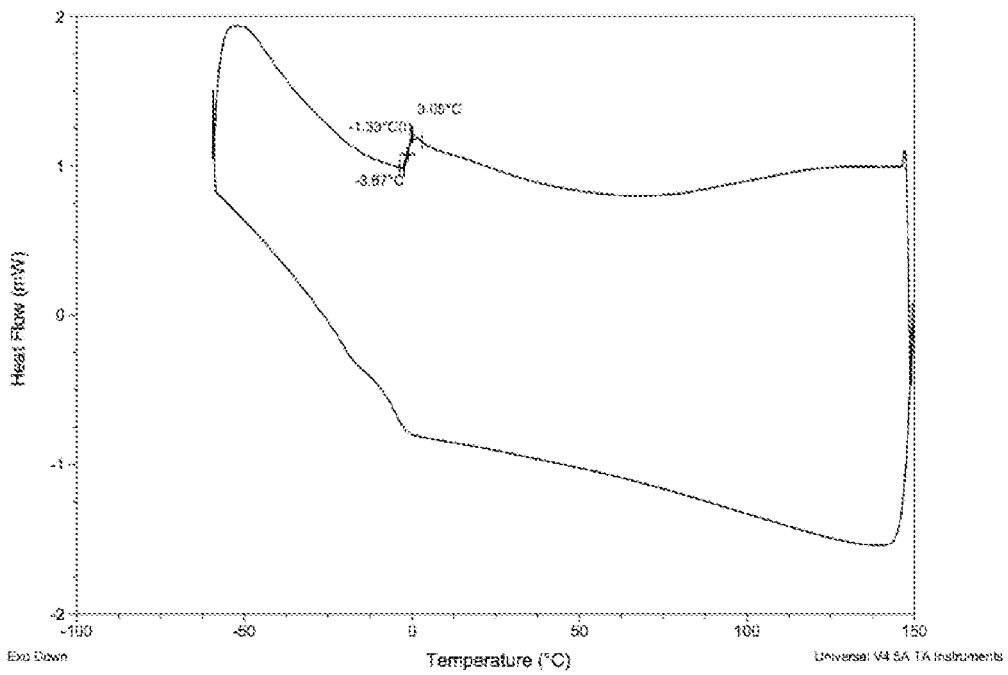
Figure 9C:
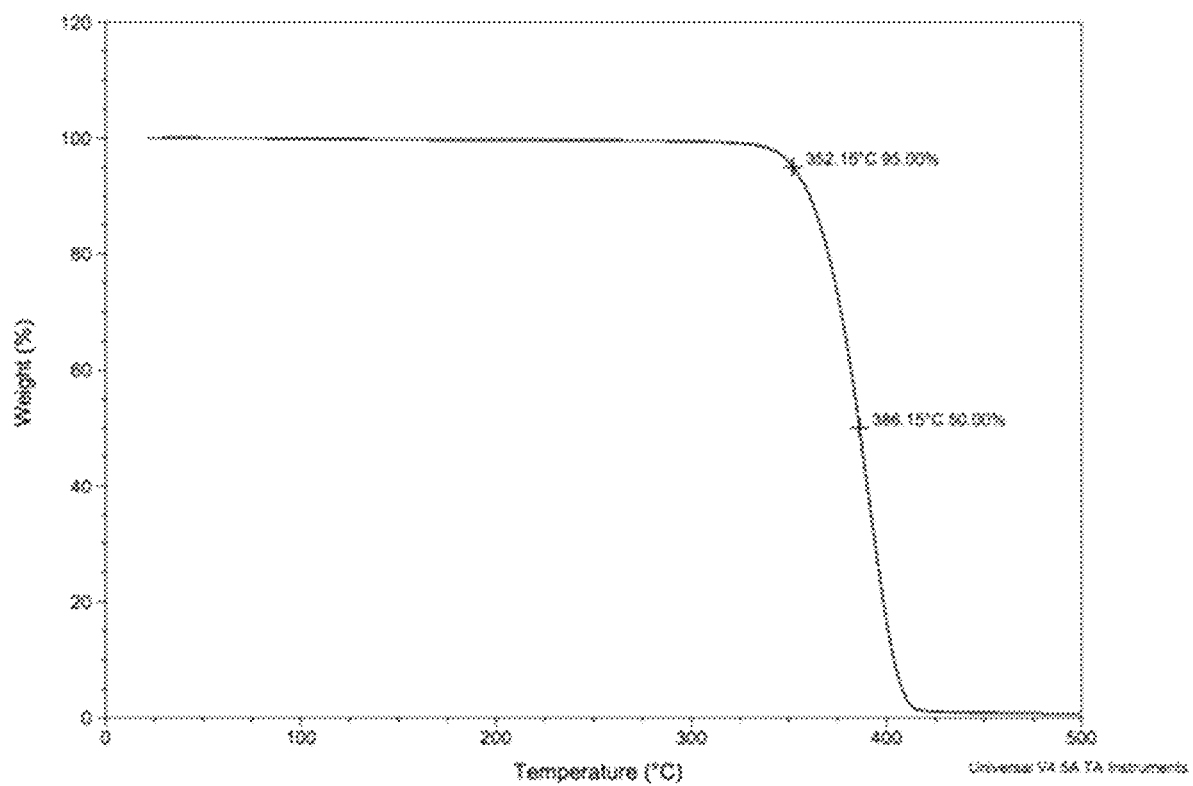
Figure 9D:
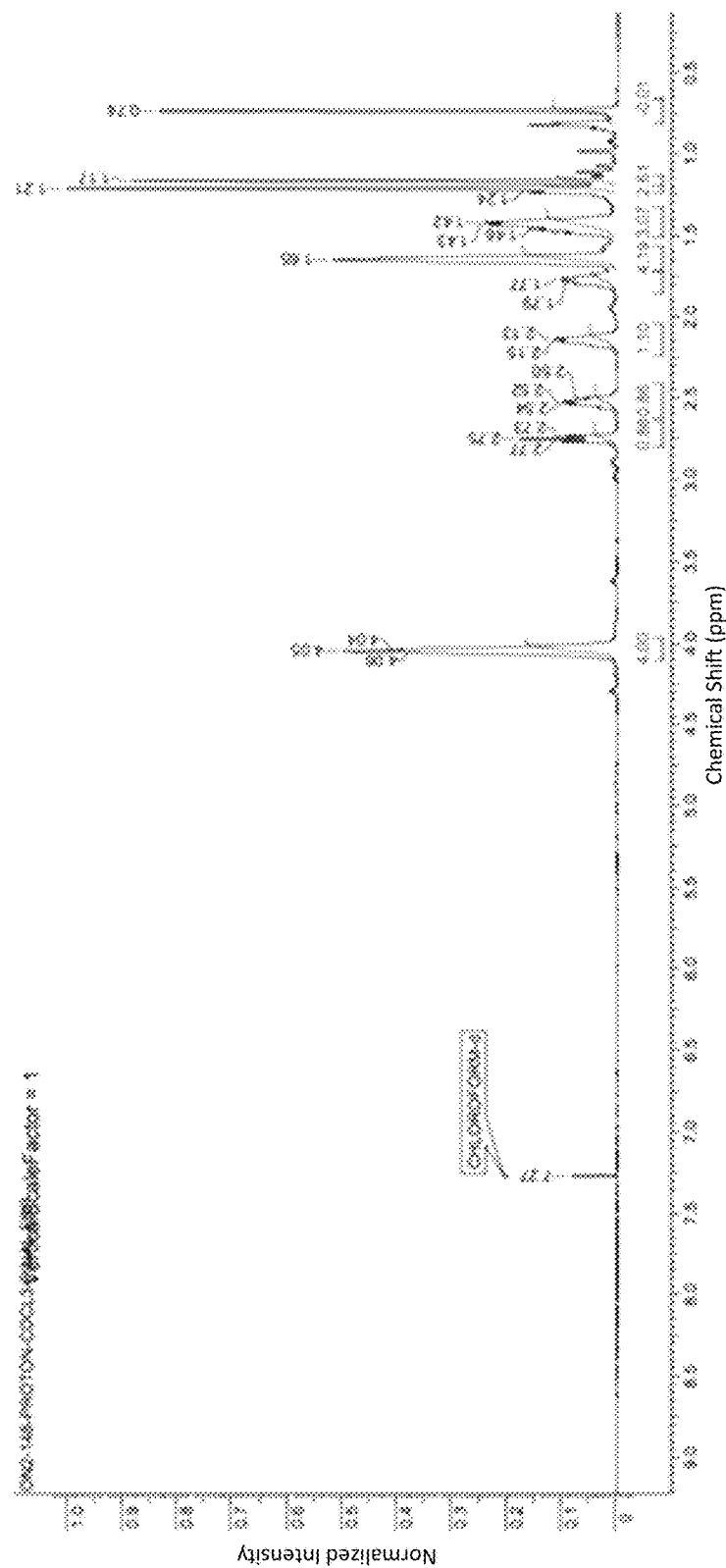
Figure 9E:
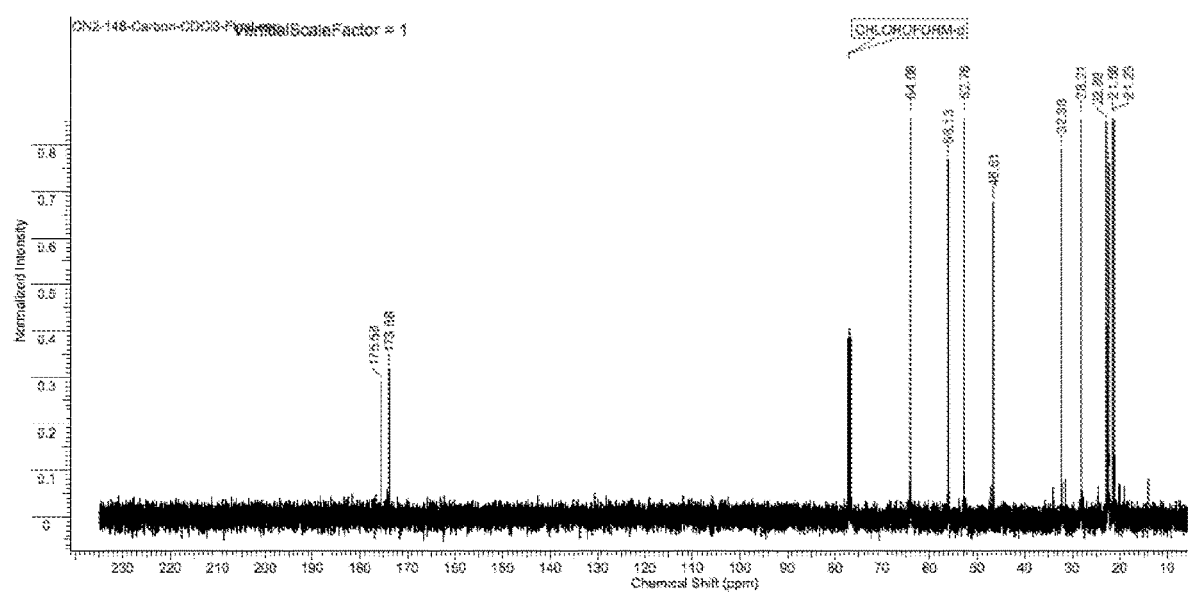
Figure 10A:
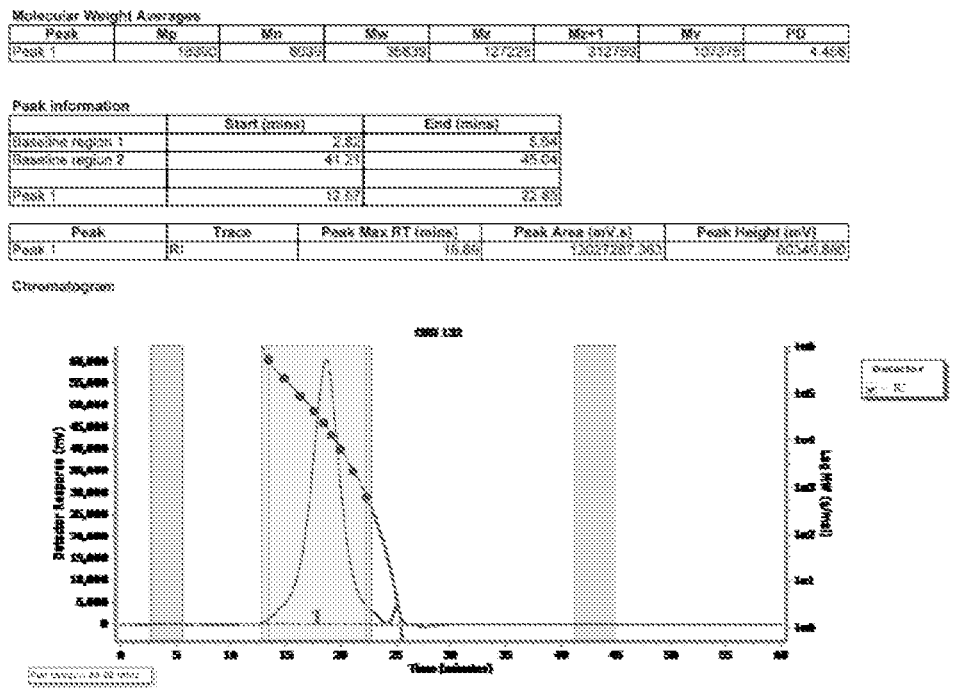
FIGS. 10A-E show characterization of polyhexylene camphorate.
Figure 10B:
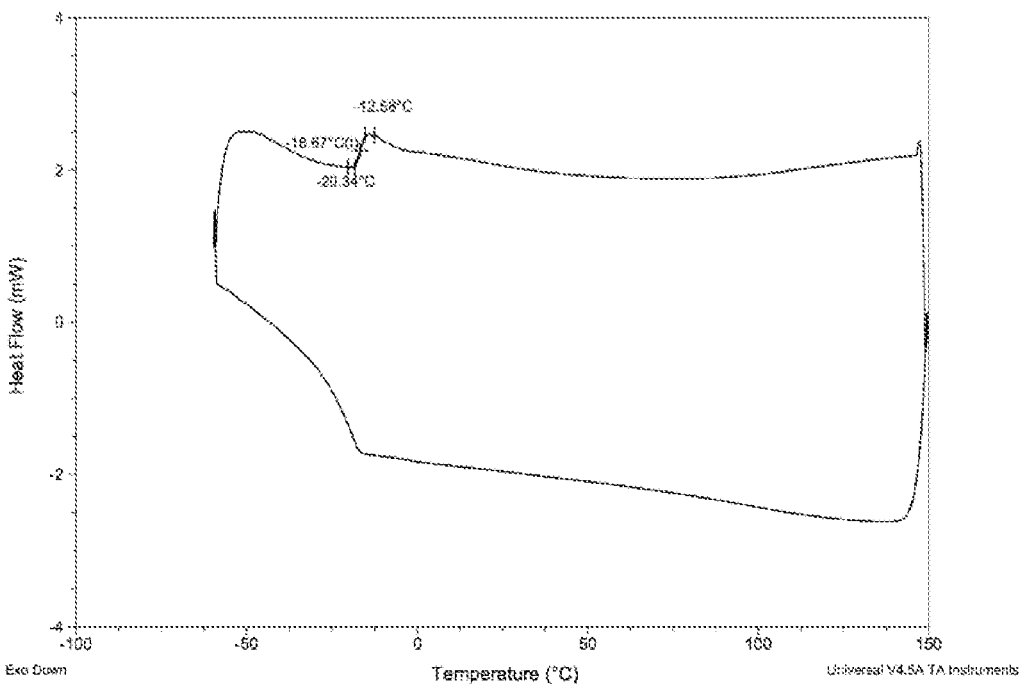
Figure 10C:
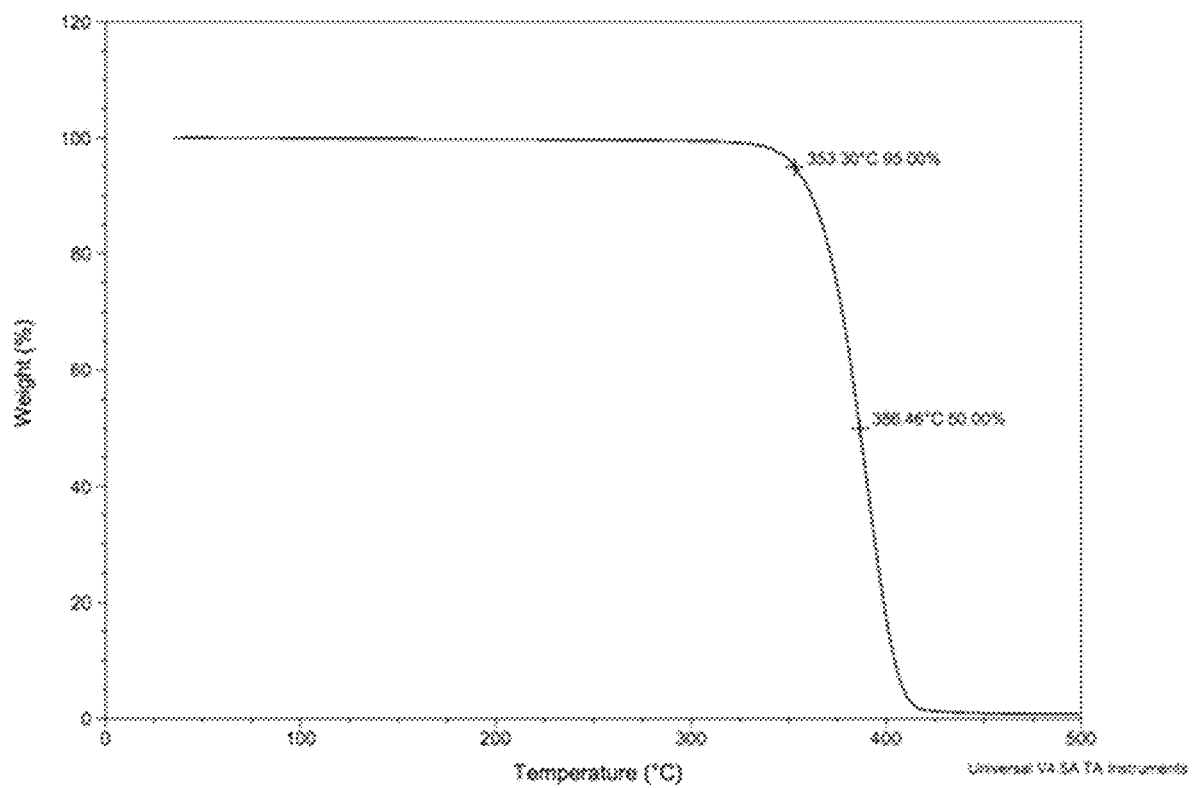
Figure 10D:
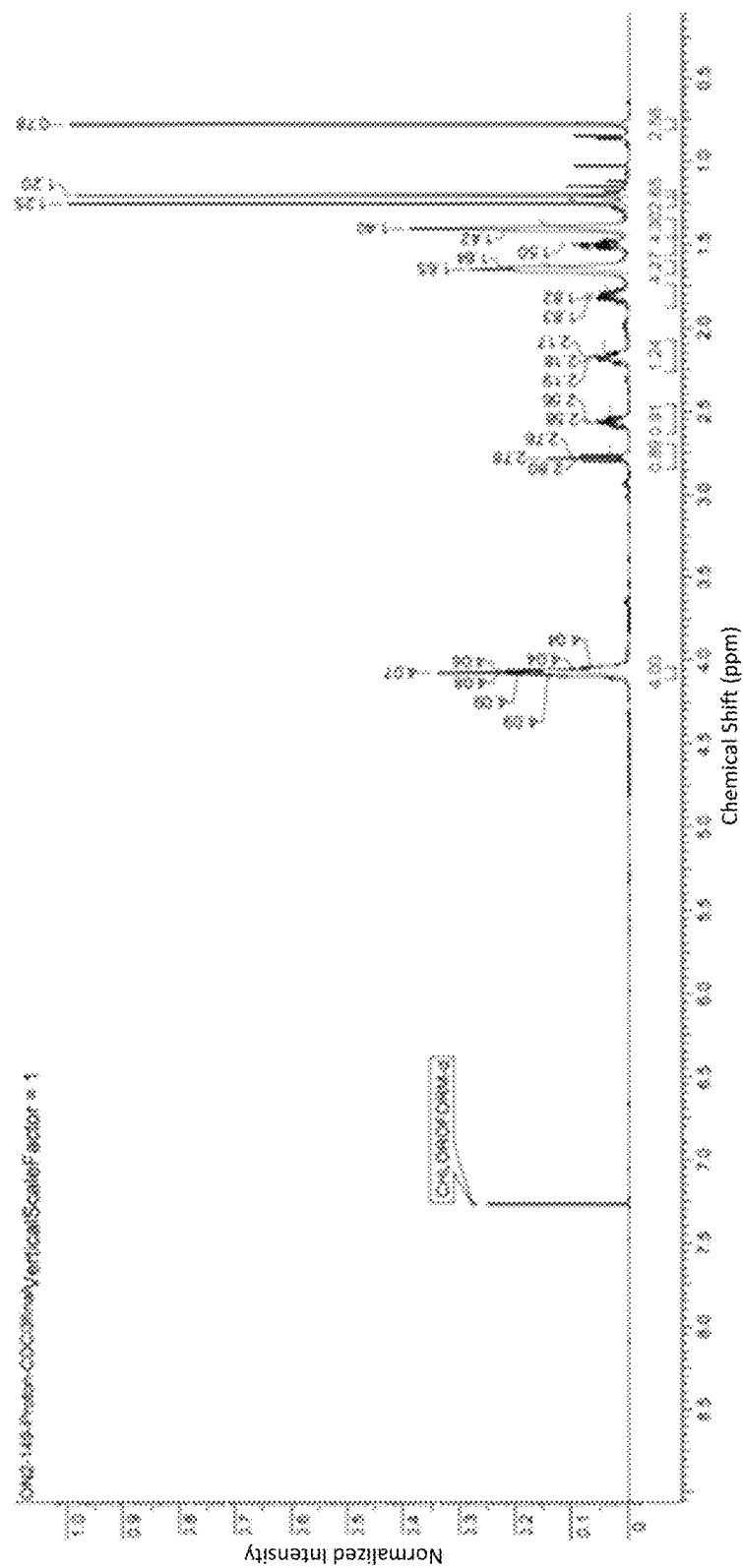
Figure 10E:
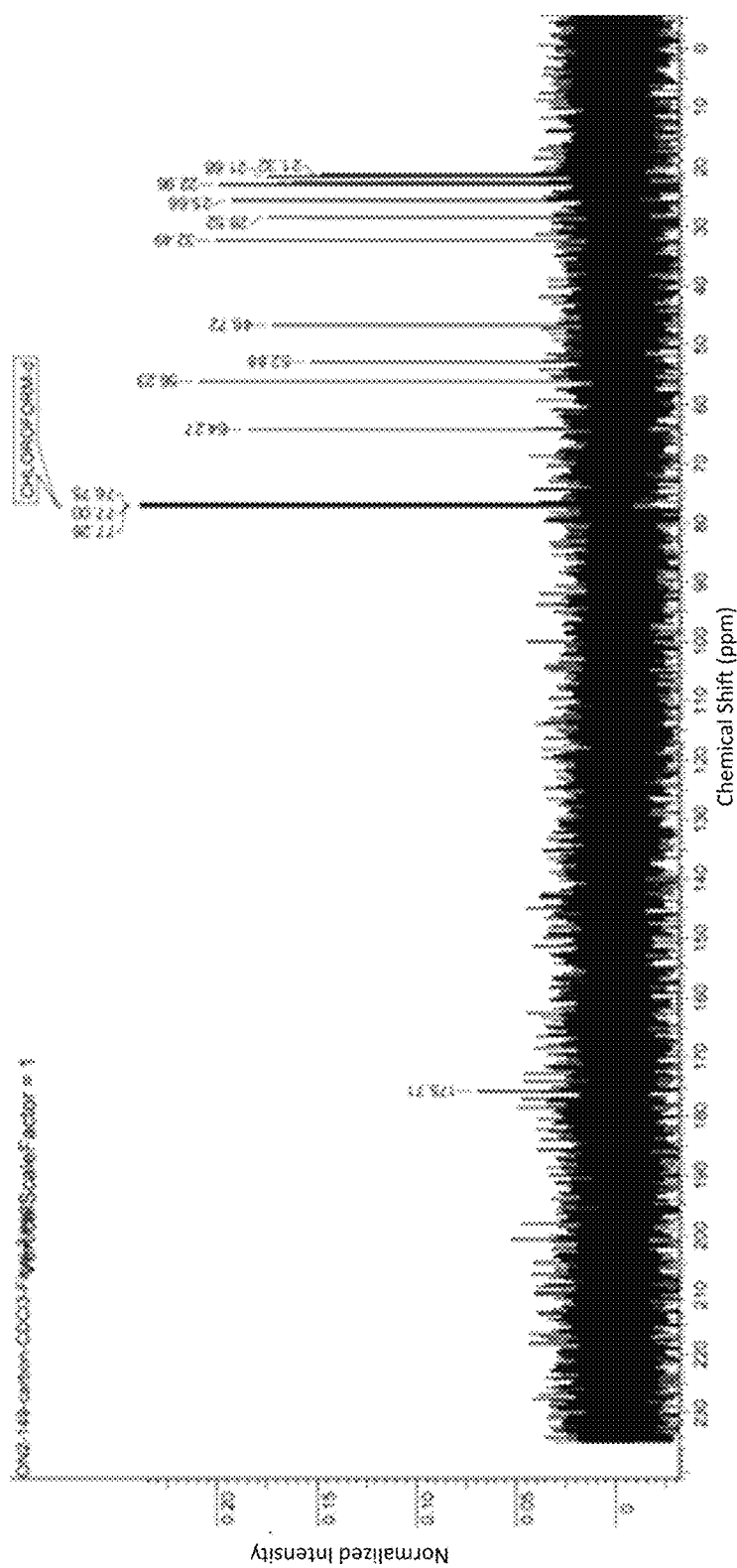
Figure 11A:
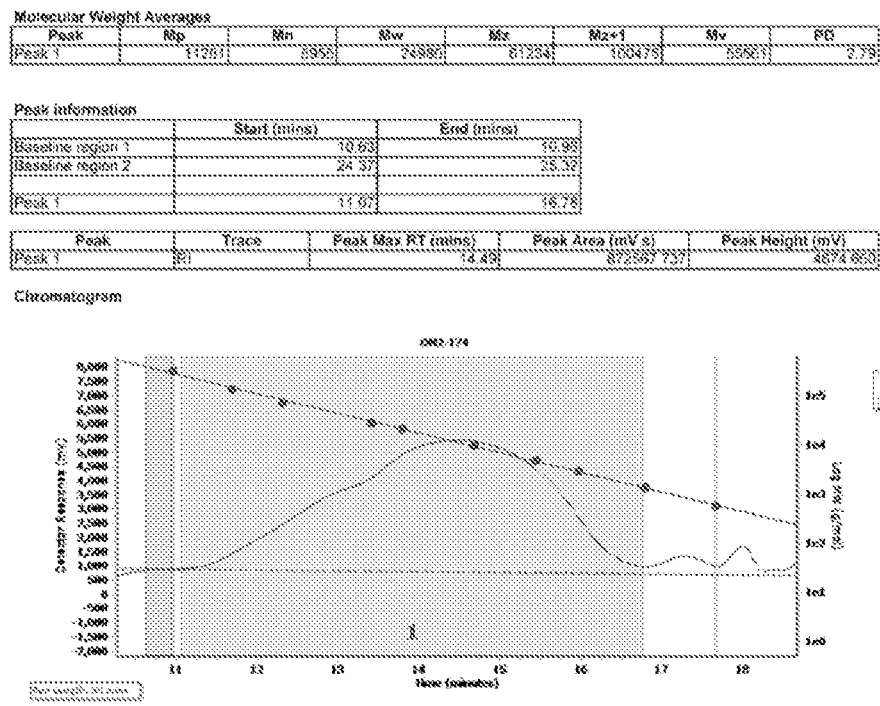
FIGS. 11A-E show characterization of polyerythritan camphorate.
Figure 11B:
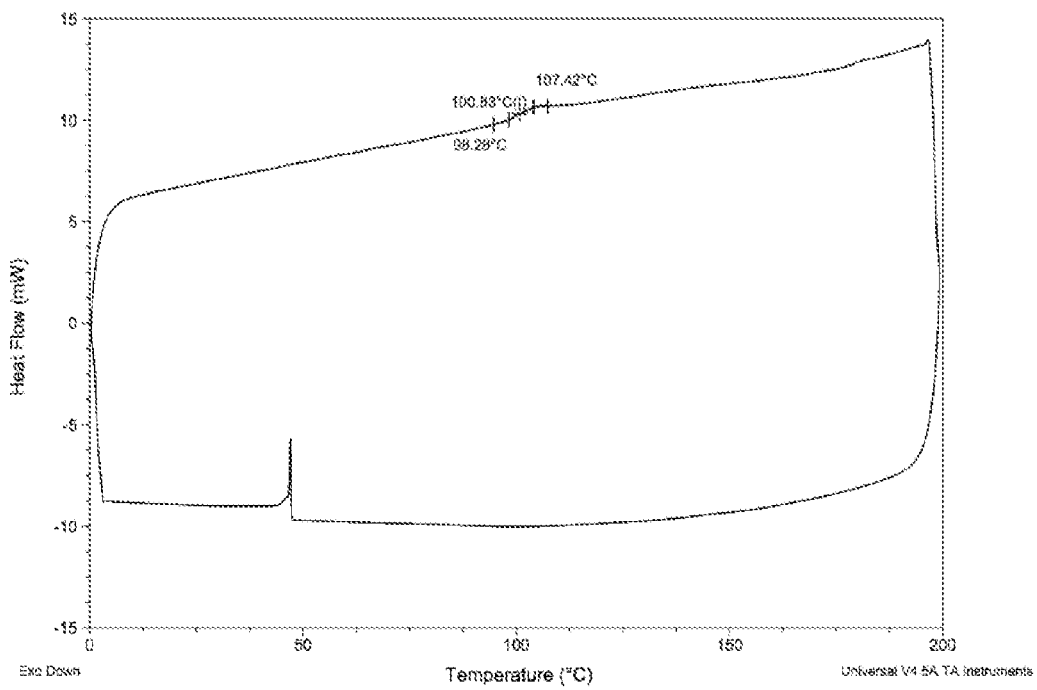
Figure 11C:
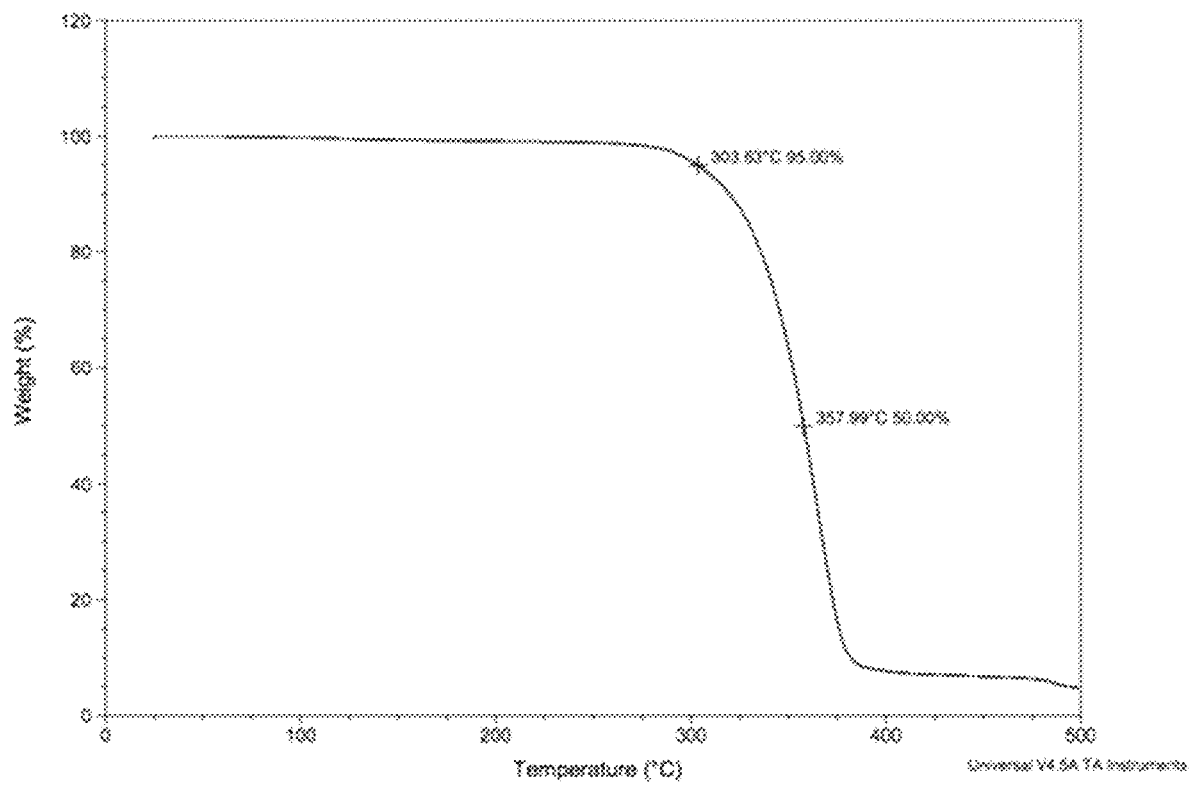
Figure 11D:
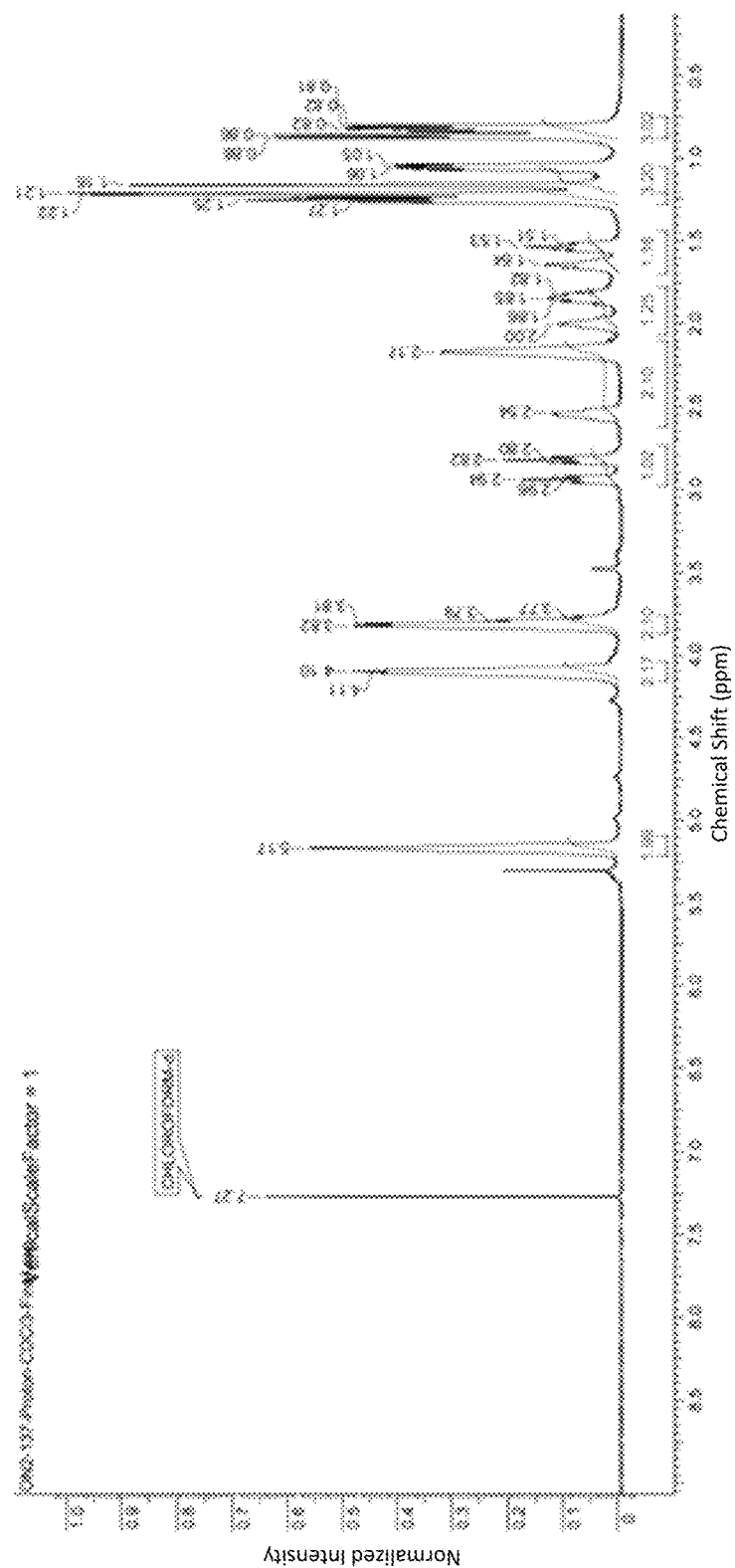
Figure 11E:
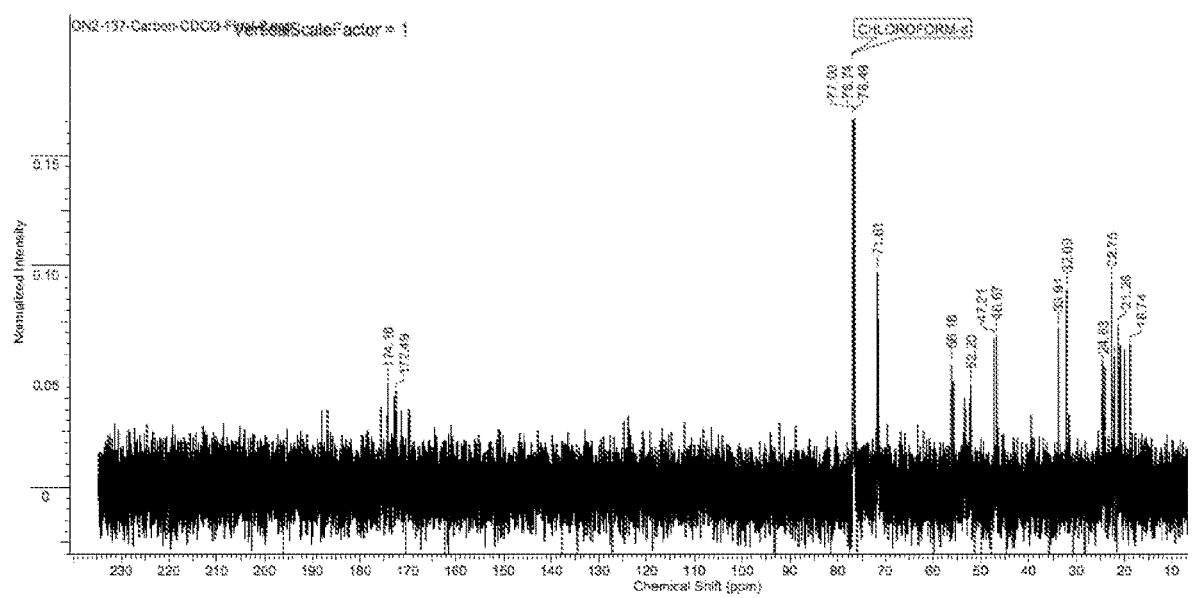
Figure 12A:
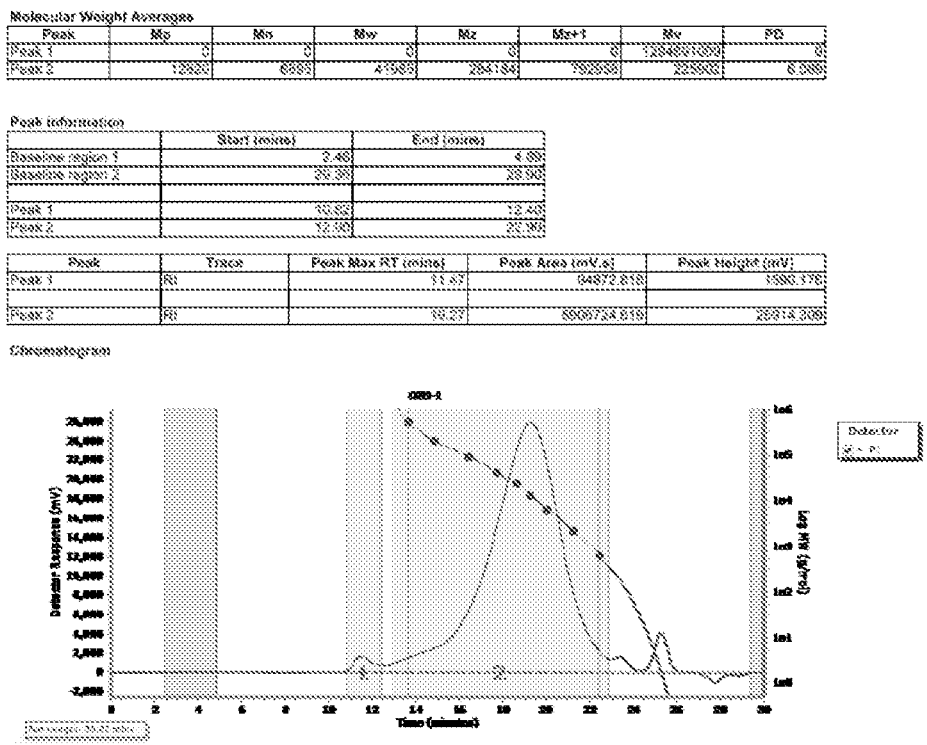
FIGS. 12A-E show characterization of polyisosorbide camphorate.
Figure 12B:
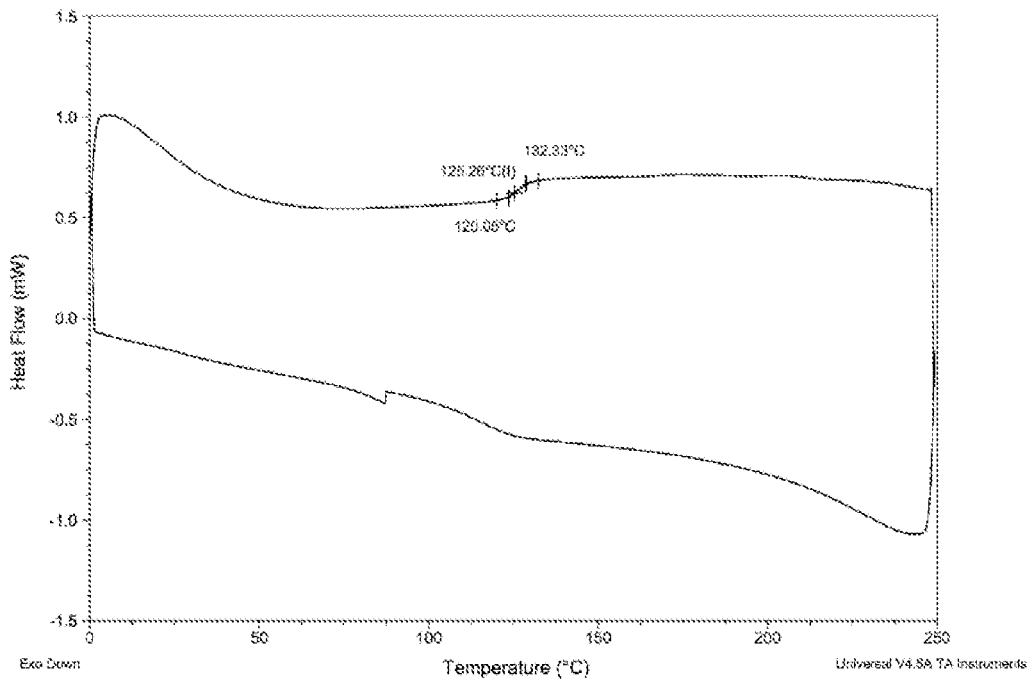
Figure 12C:
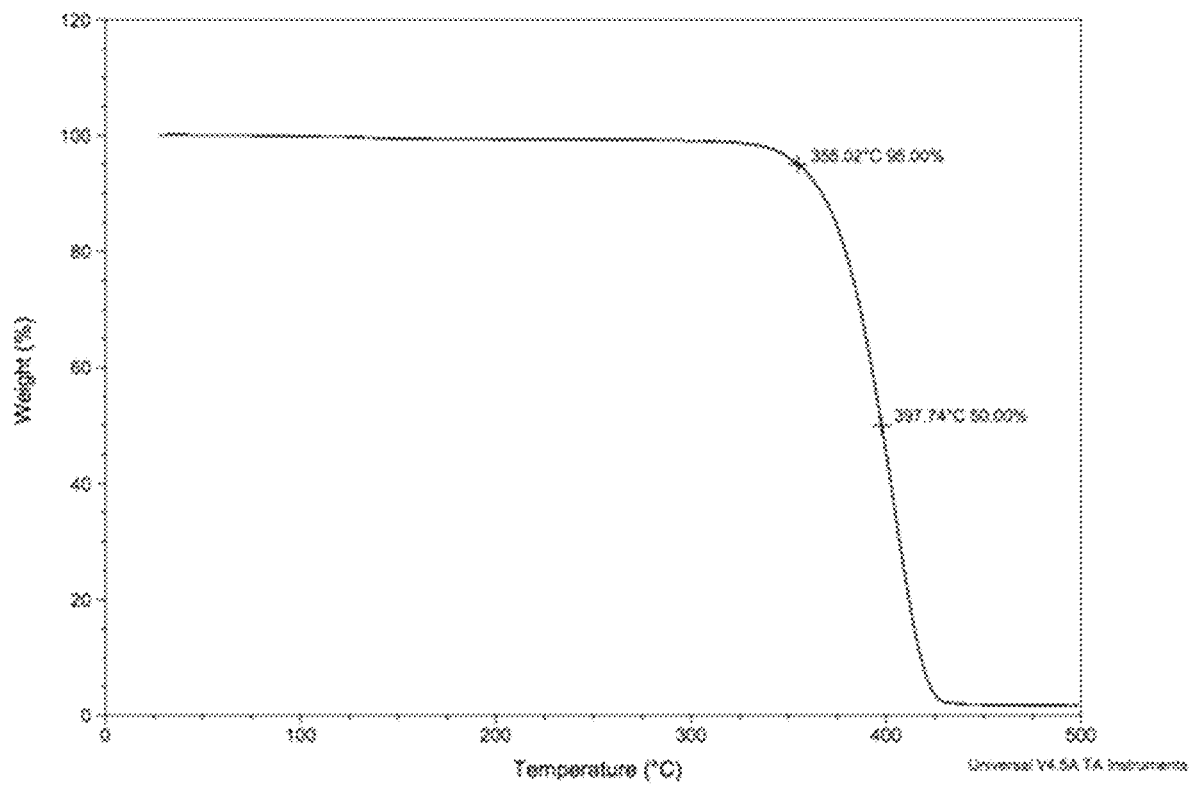
Figure 12D:
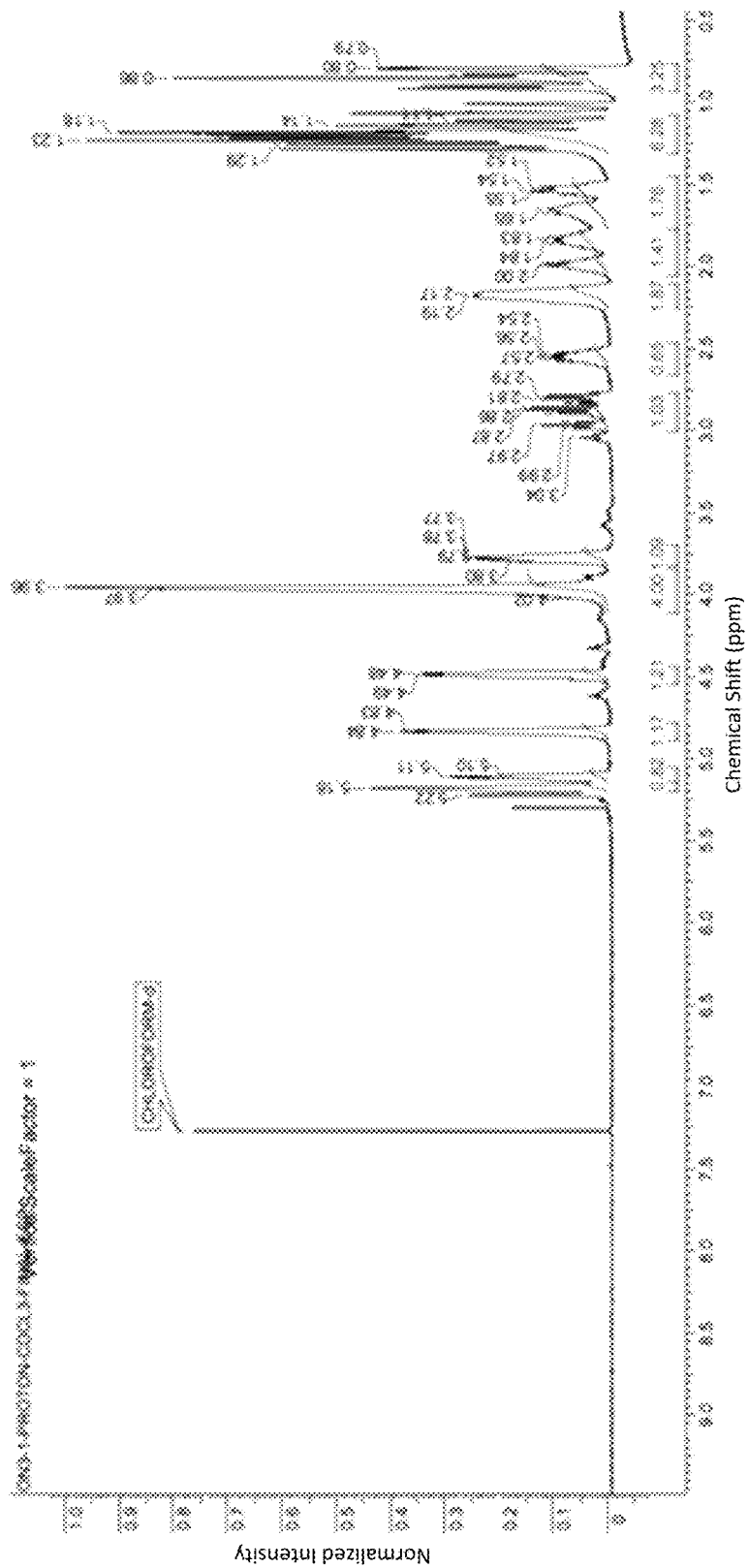
Figure 12E:
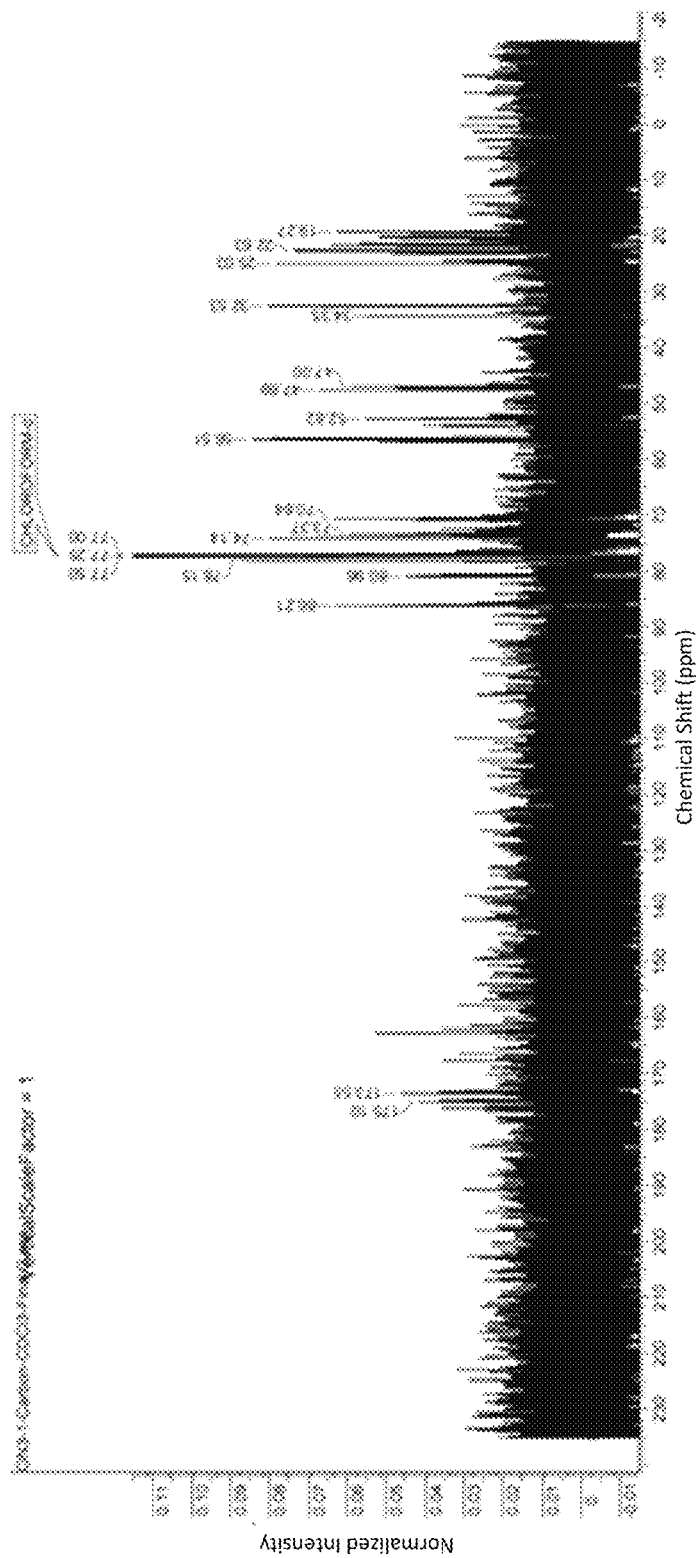
Figure 13A:
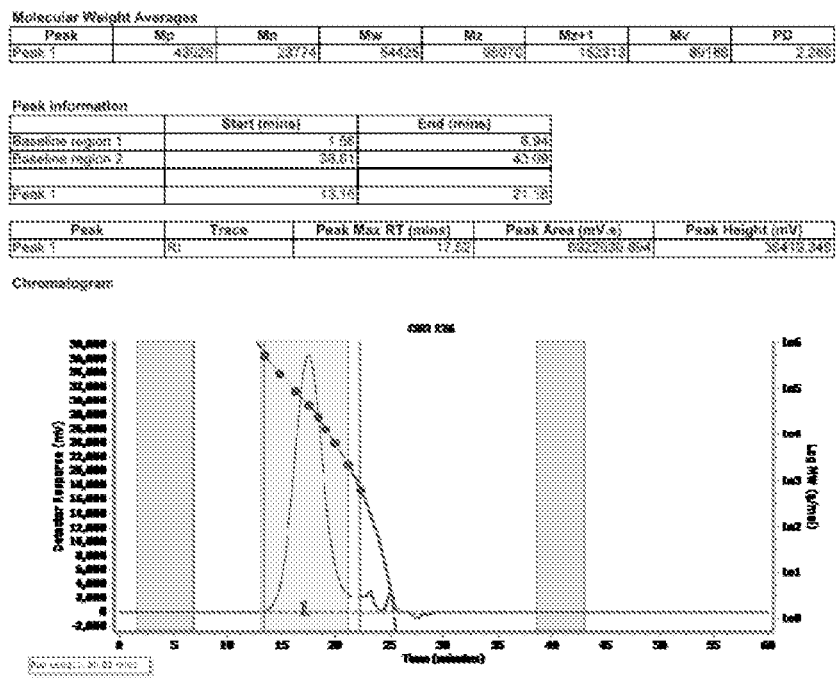
FIGS. 13A-E show characterization of polyBHEC (where BHEC is bis(2-hydroxyethyl) camphorate).
Figure 13B:
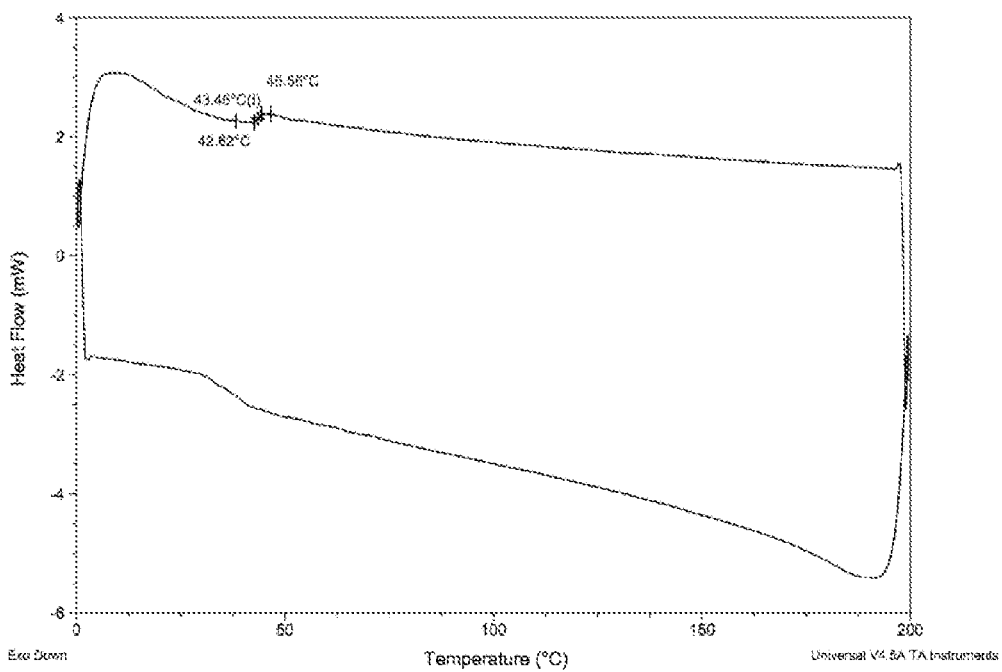
Figure 13C:
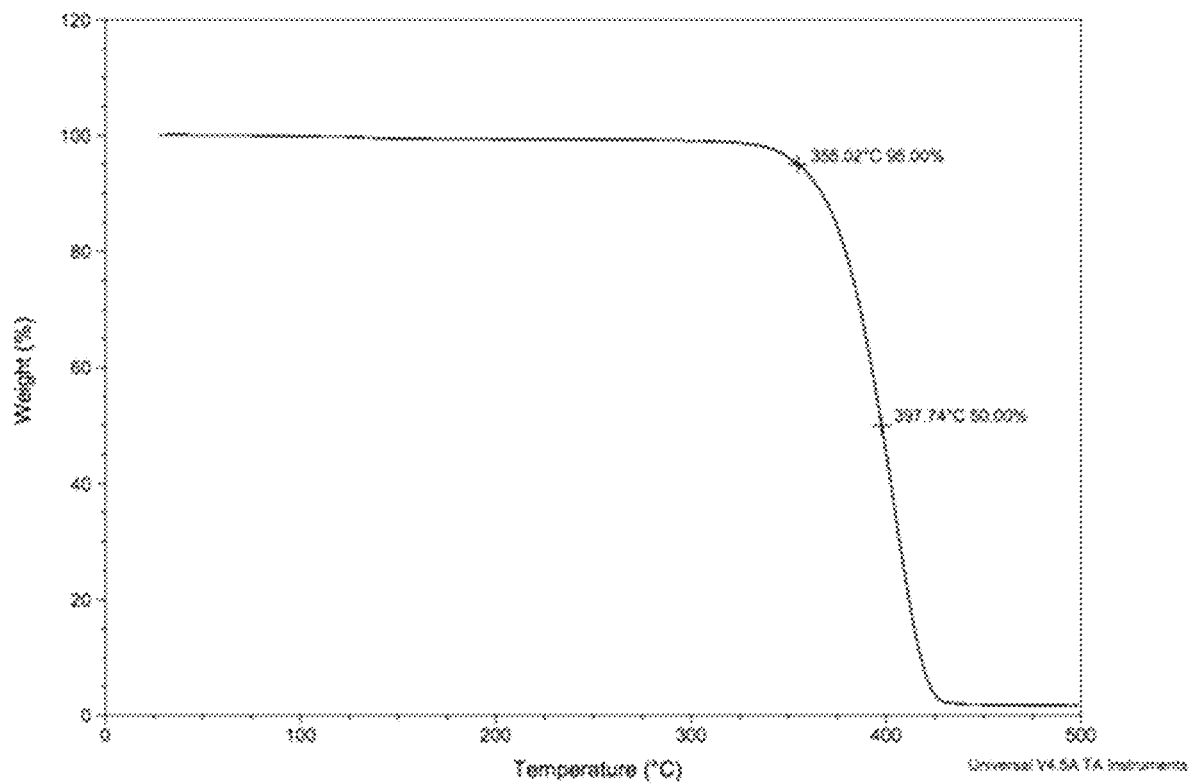
Figure 13D:
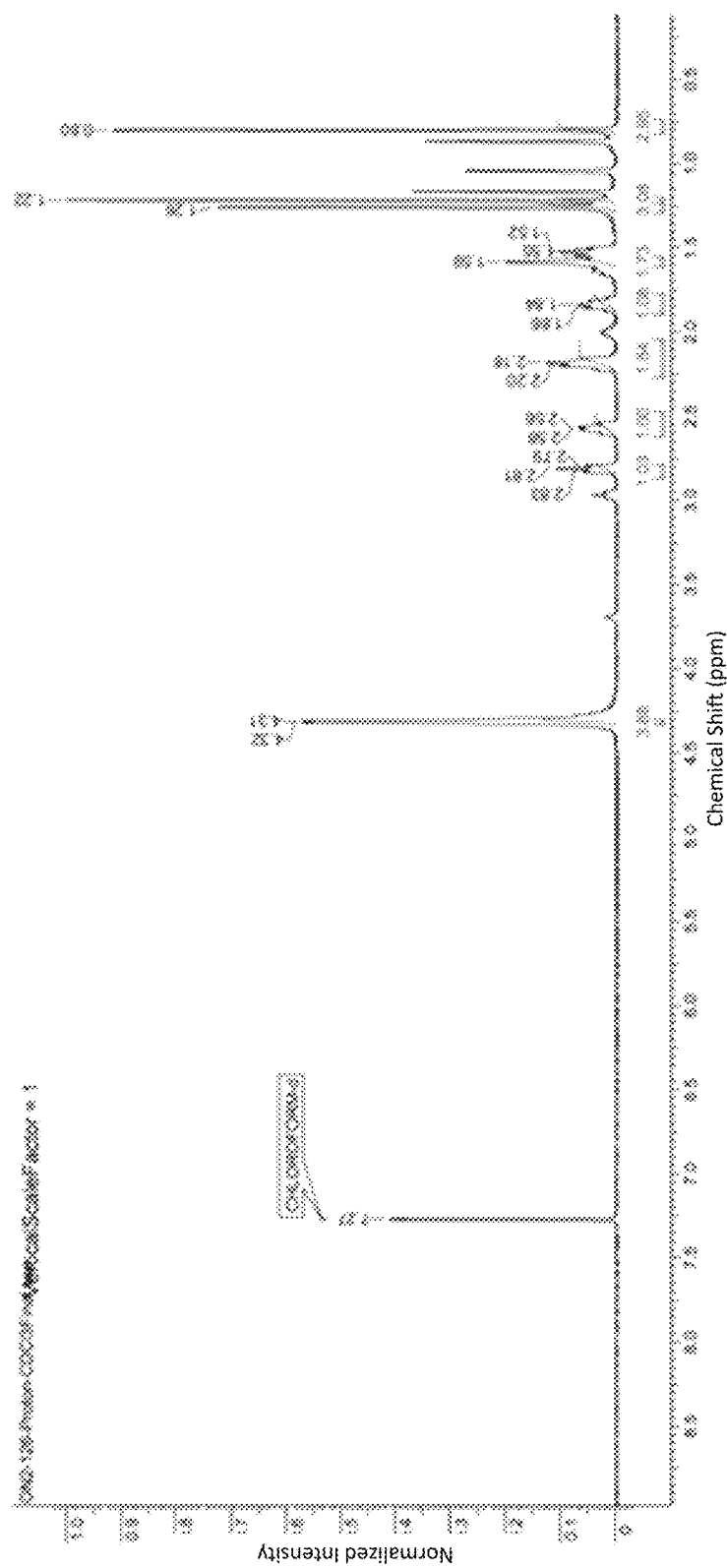
Figure 13E:
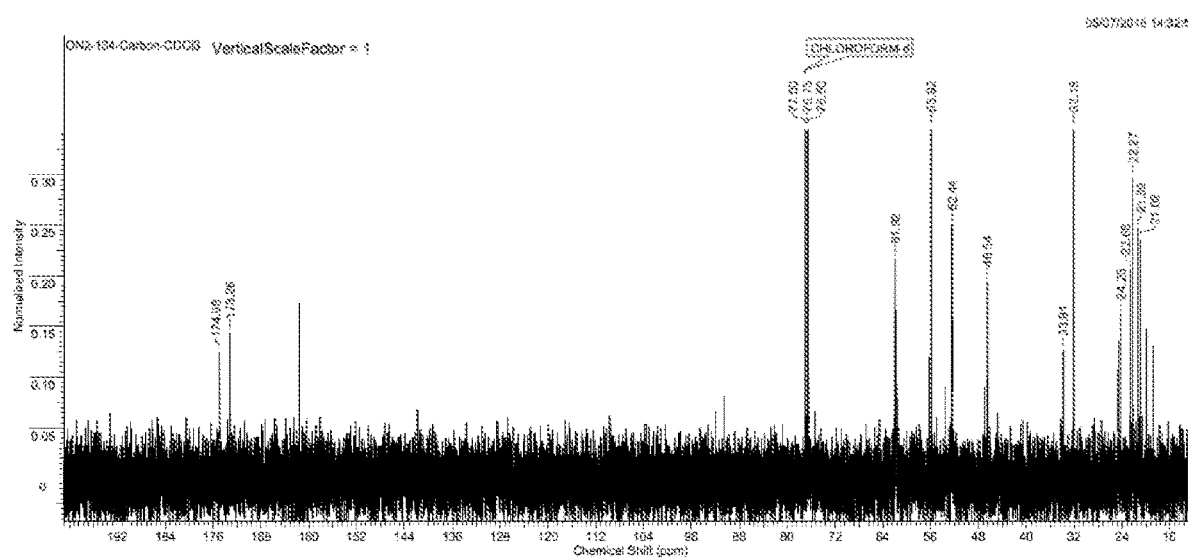
Figure 14A:
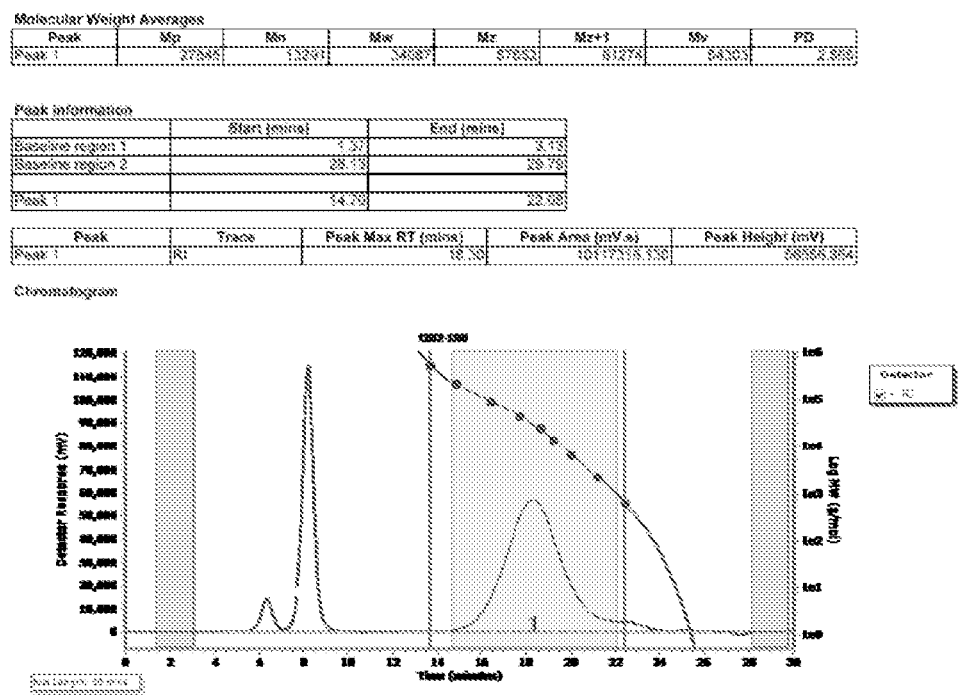
Figure 14B:
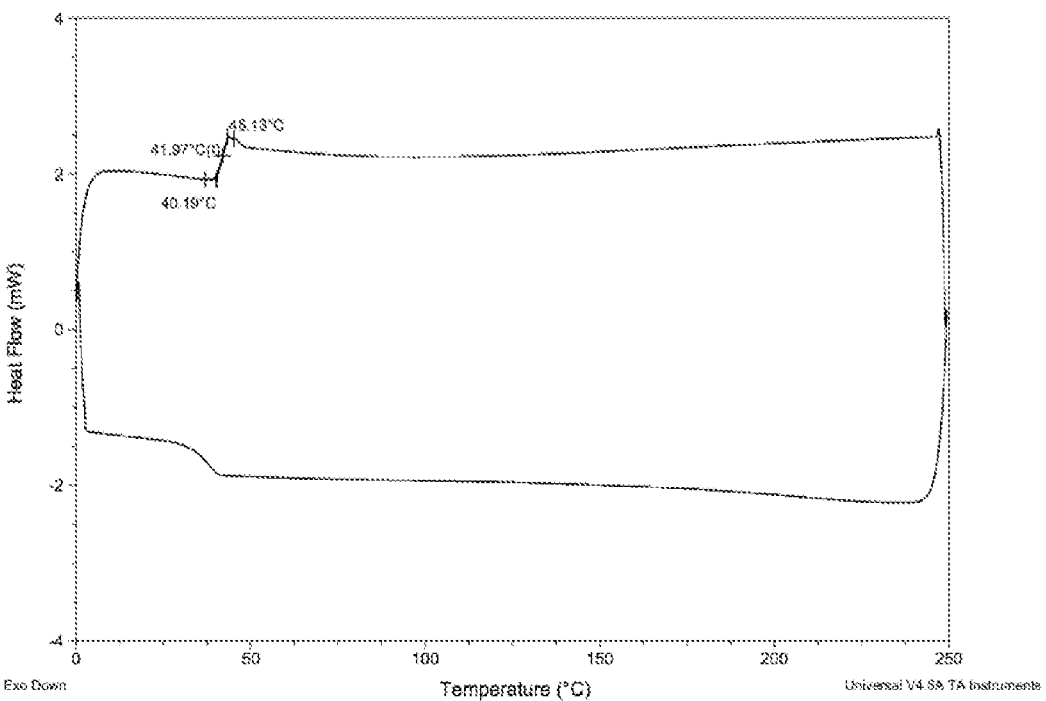
Figure 14C:
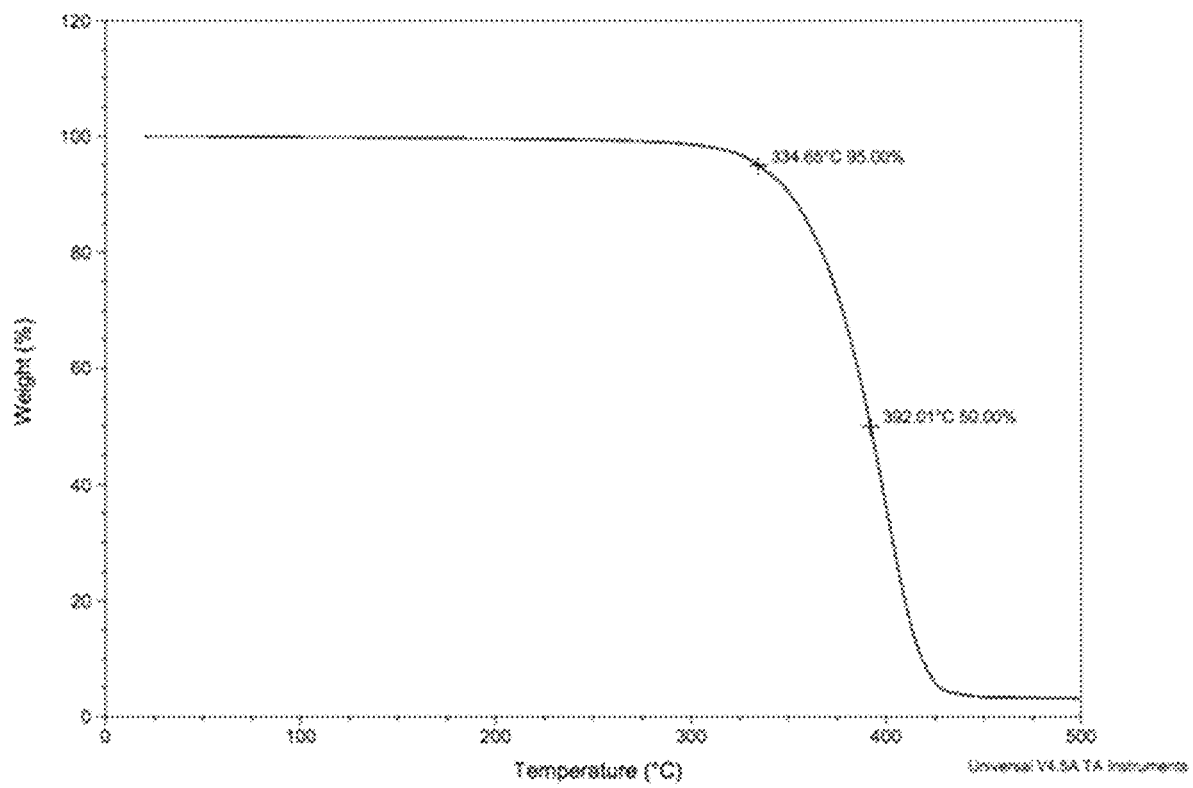
Figure 15A:
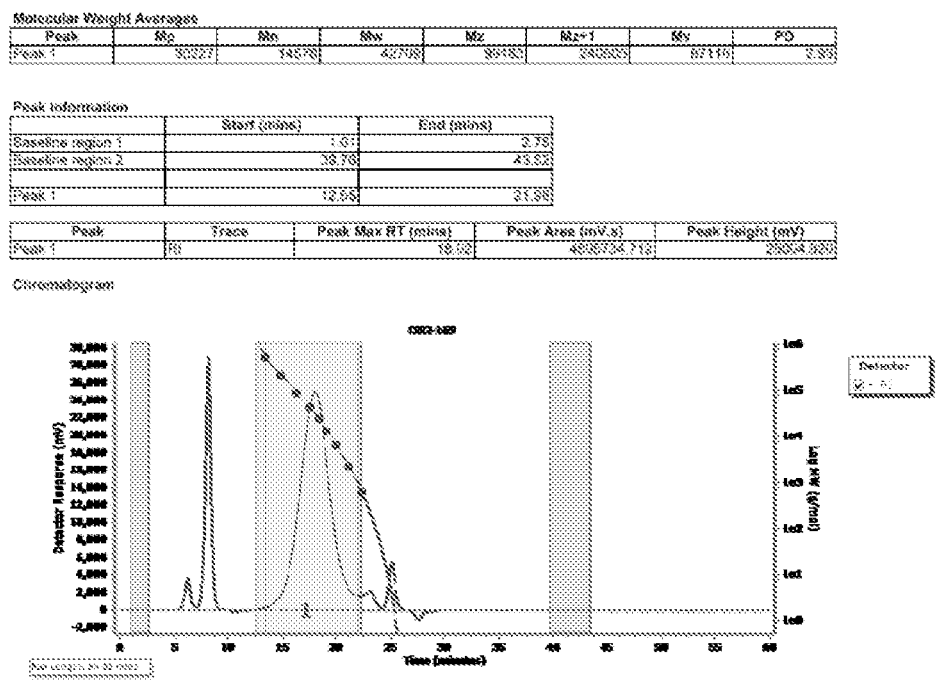
FIGS. 15A-E show characterization of poly(BHEC/BHET) with 80% BHEC.
Figure 15B:
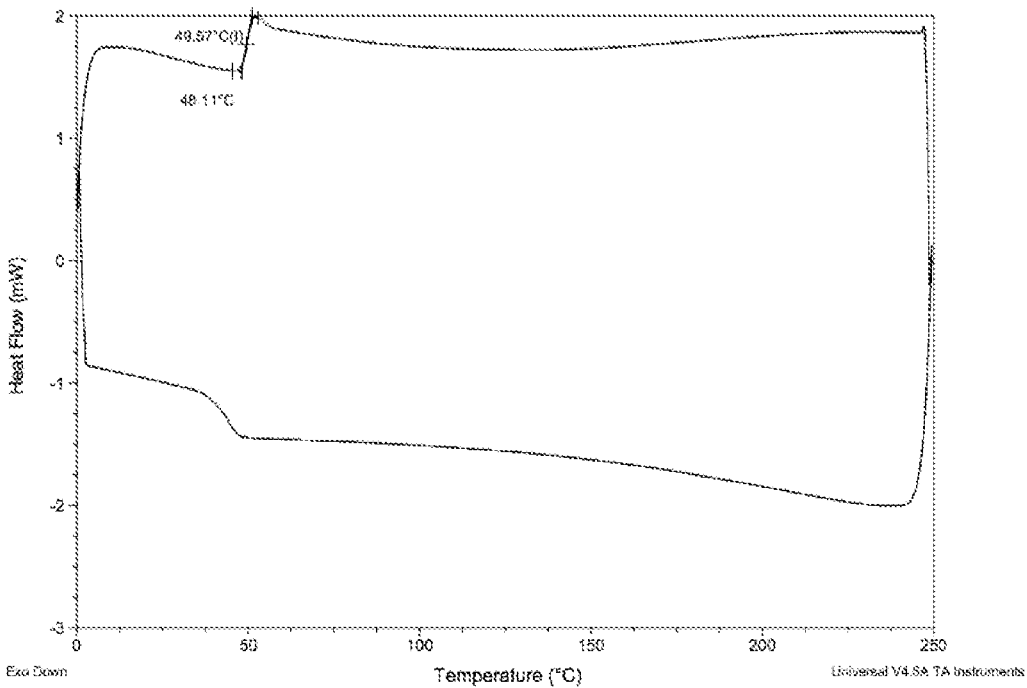
Figure 15C:
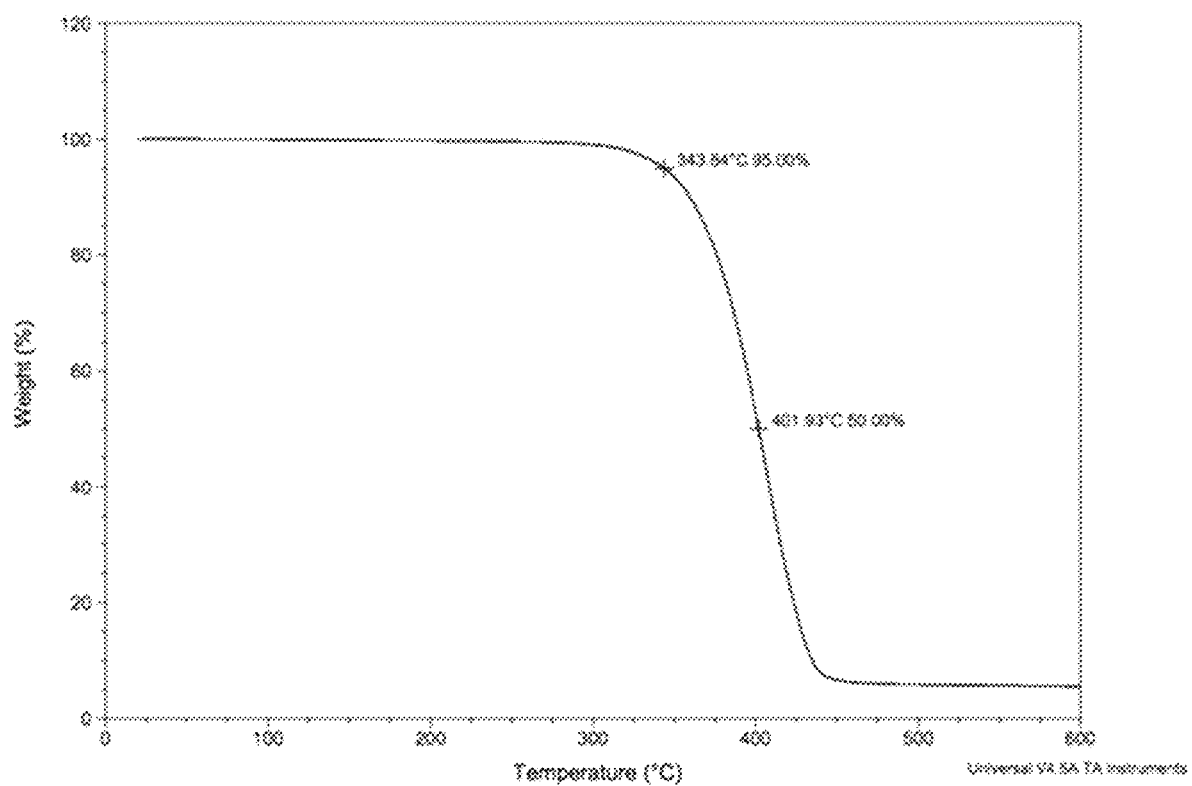
Figure 15D:
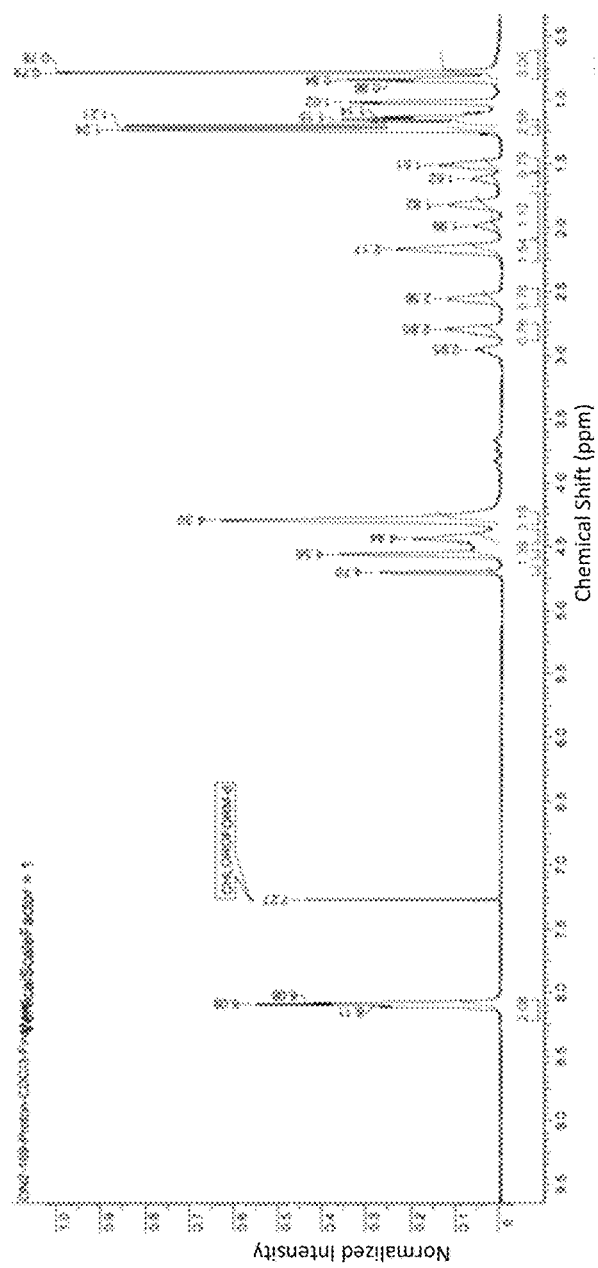
Figure 15E:
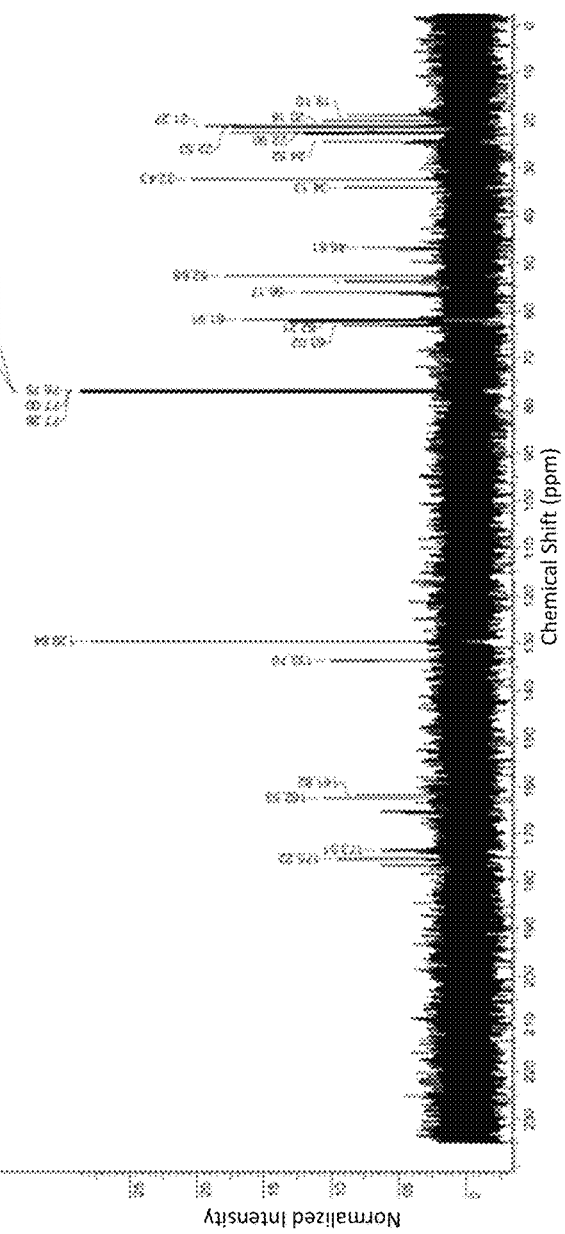
Figure 16A:
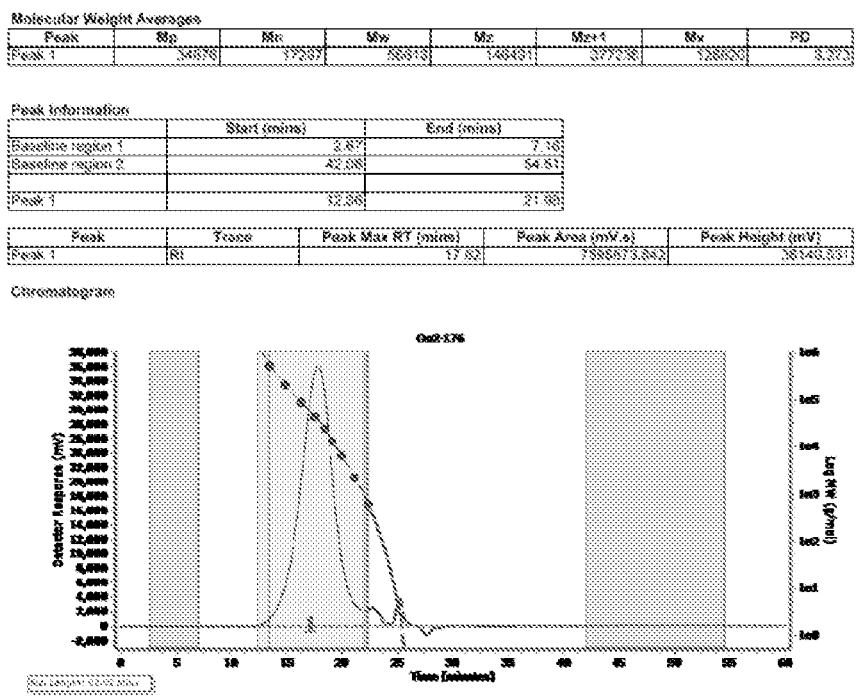
FIGS. 16A-E show characterization of poly(BHEC/BHET) with 70% BHEC.
Figure 16B:
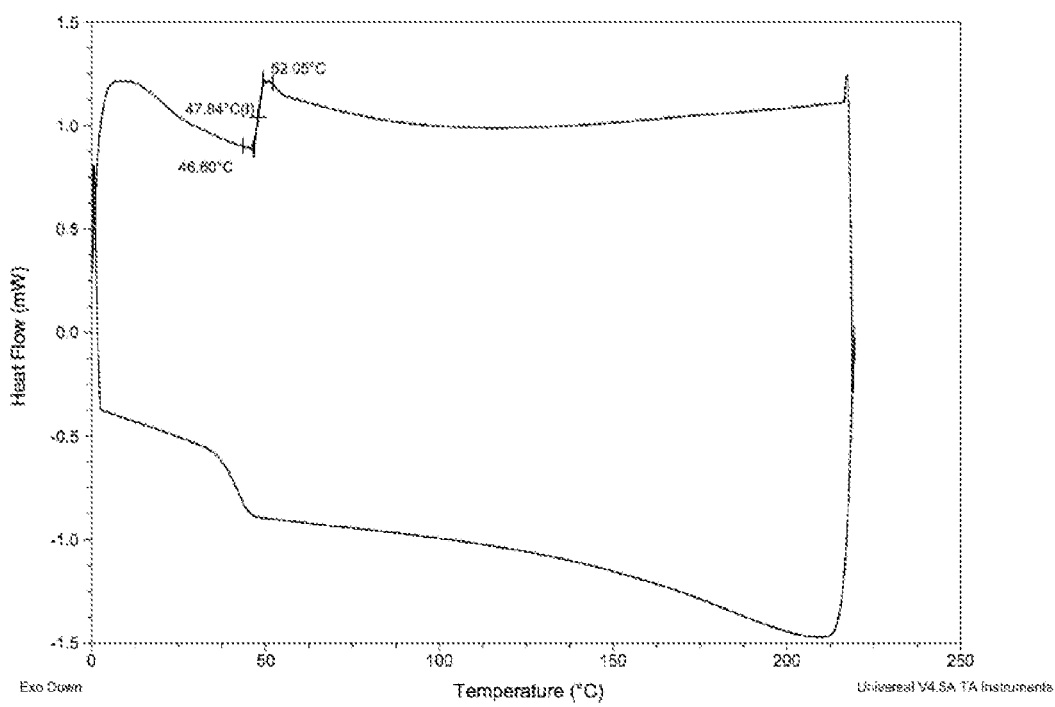
Figure 16C:
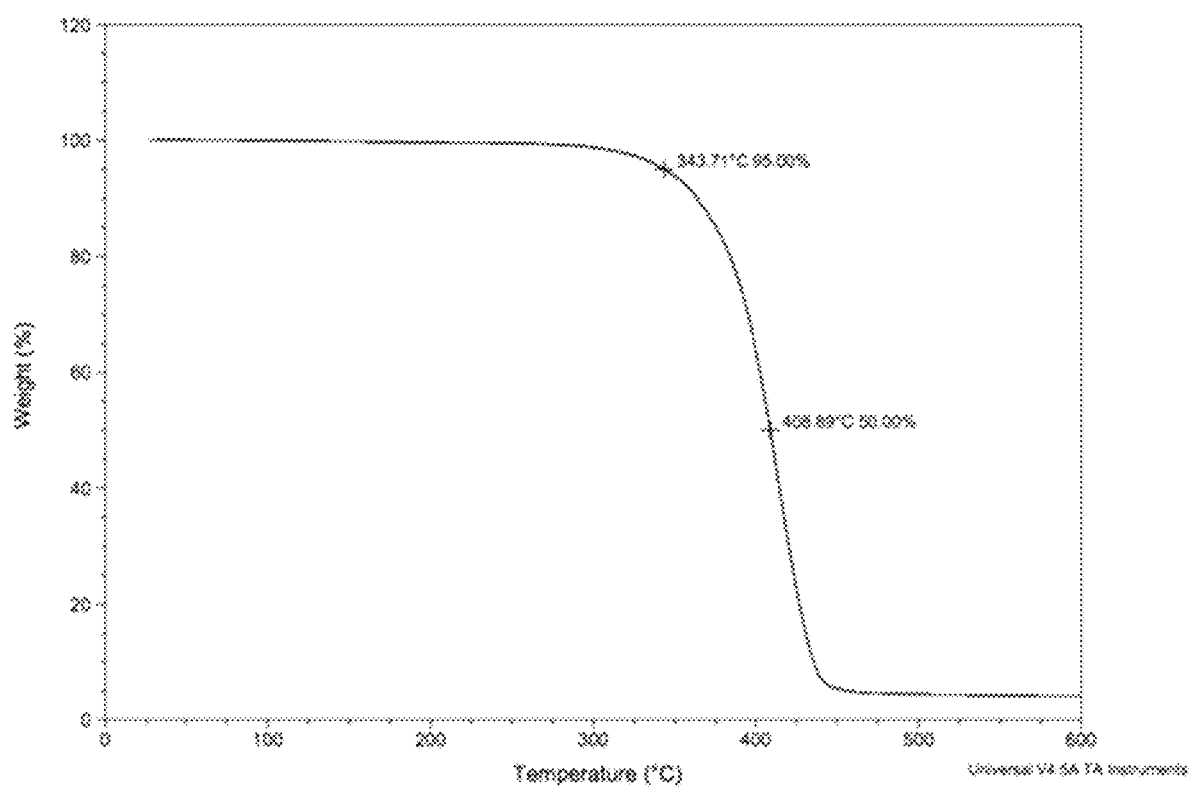
Figure 16D:
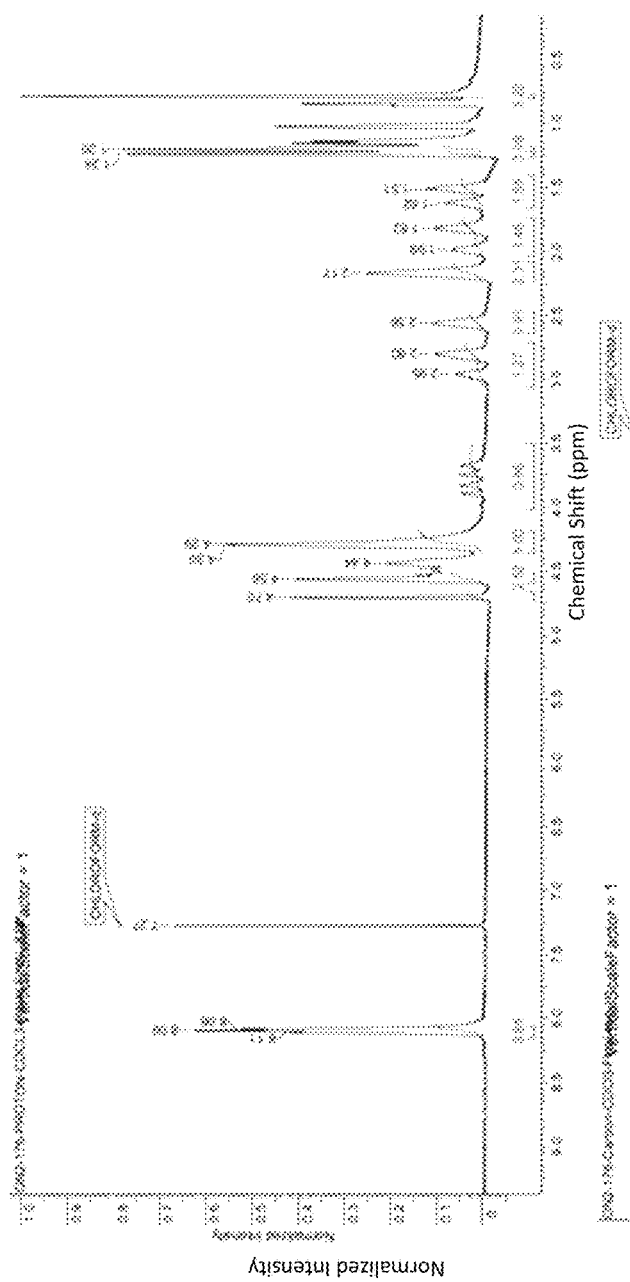
Figure 16E:
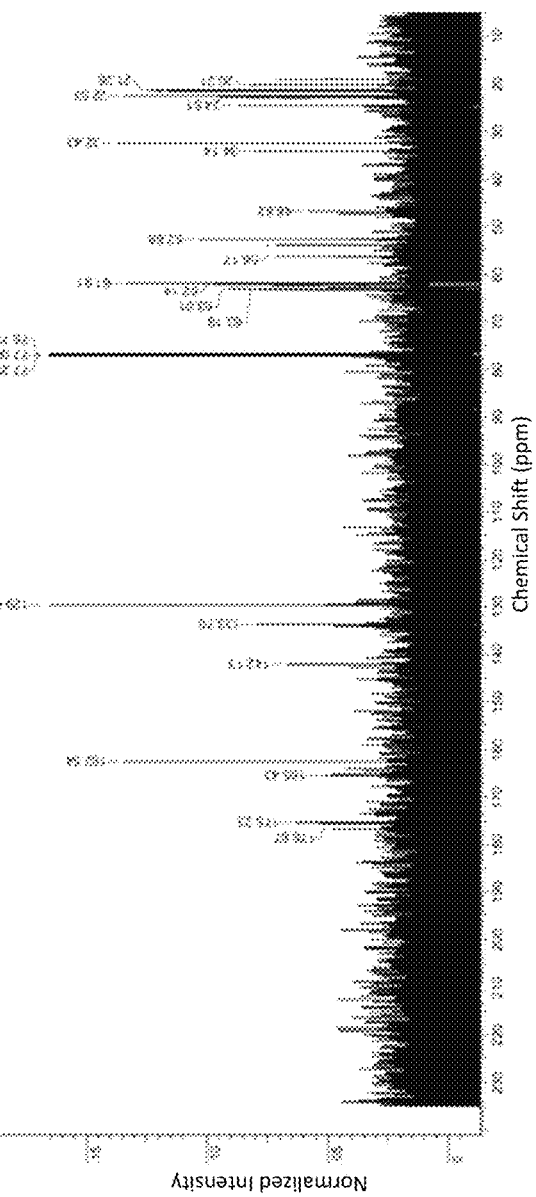
Figure 17A:
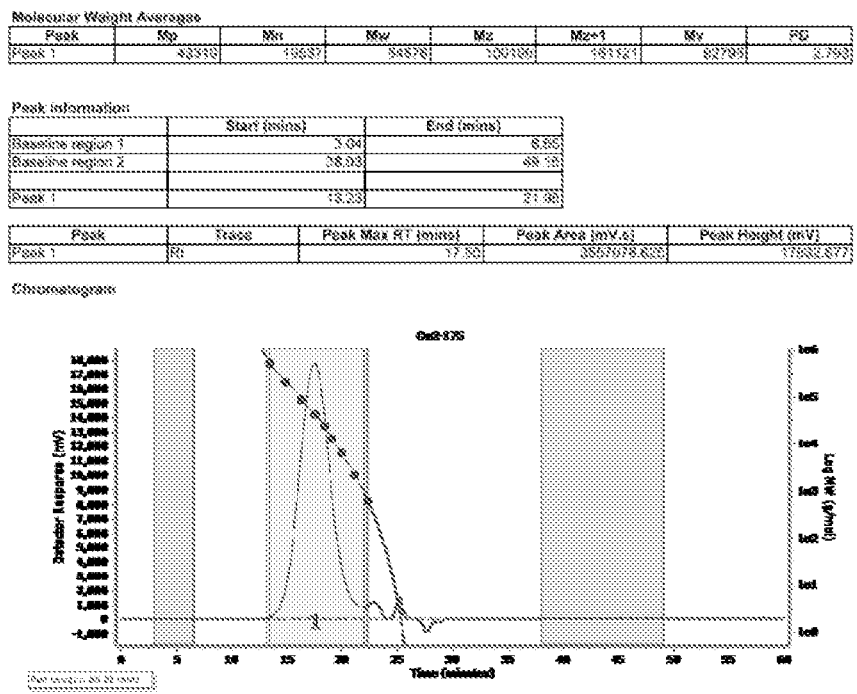
FIGS. 17A-E show characterization of poly(BHEC/BHET) with 60% BHEC.
Figure 17B:
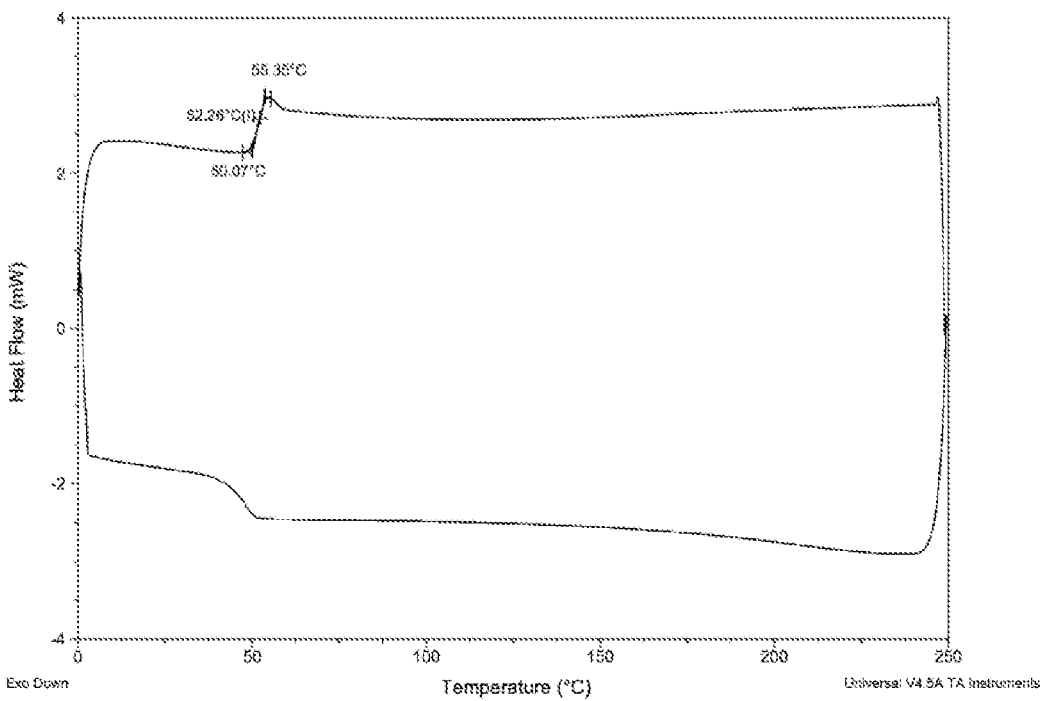
Figure 17C:
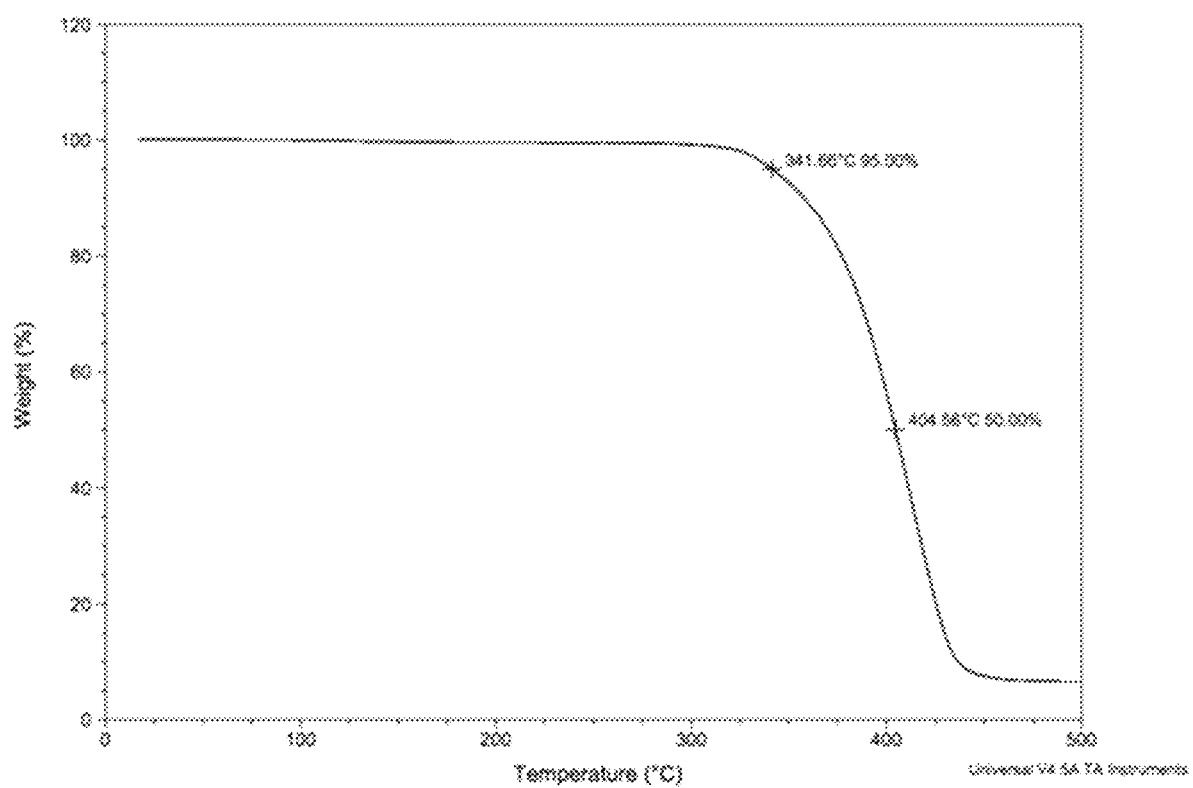
Figure 17D:
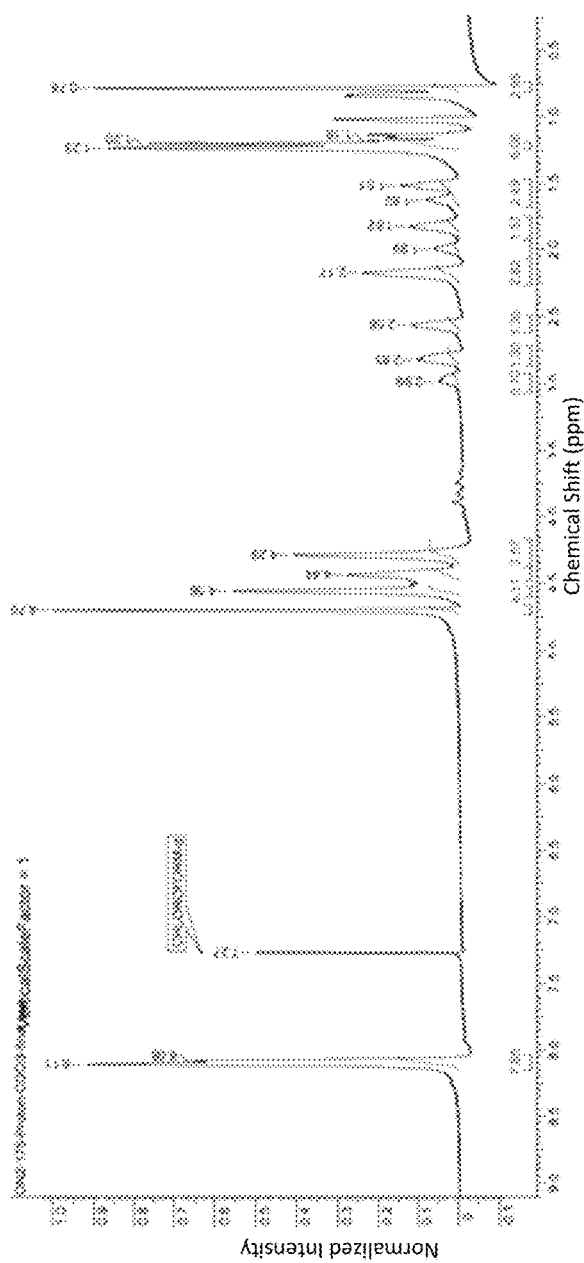
Figure 17E:
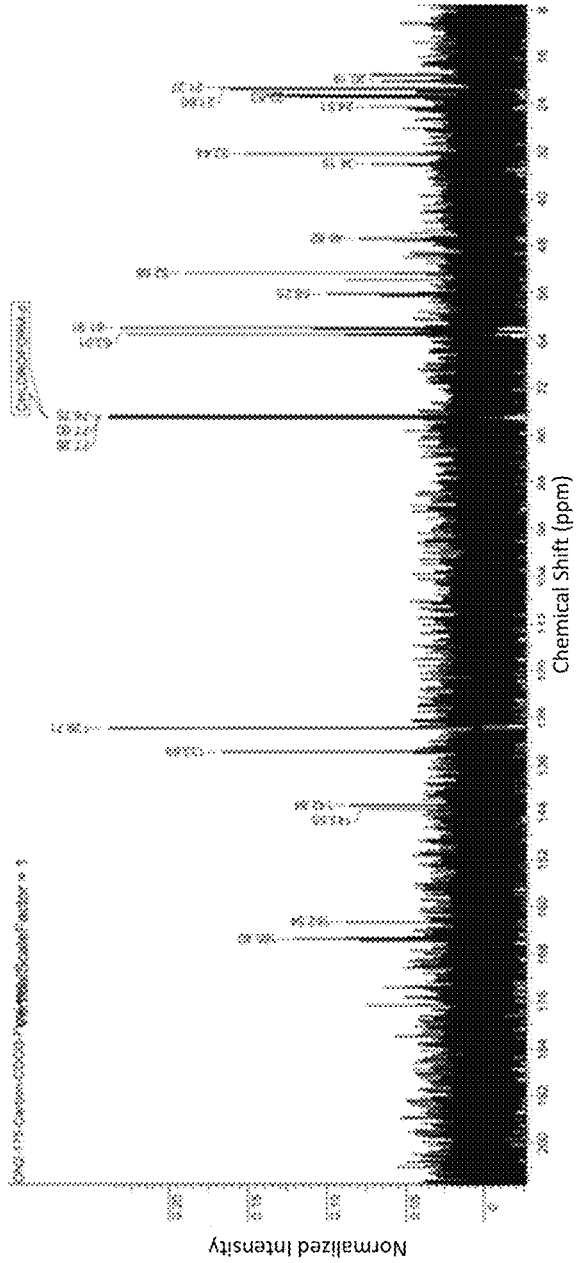
Figure 18A:
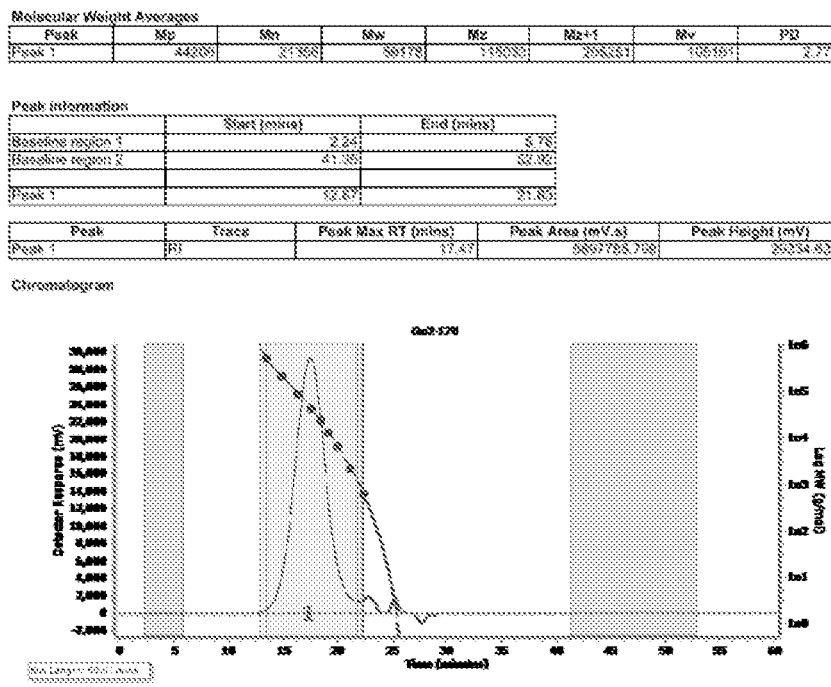
Figure 18B:
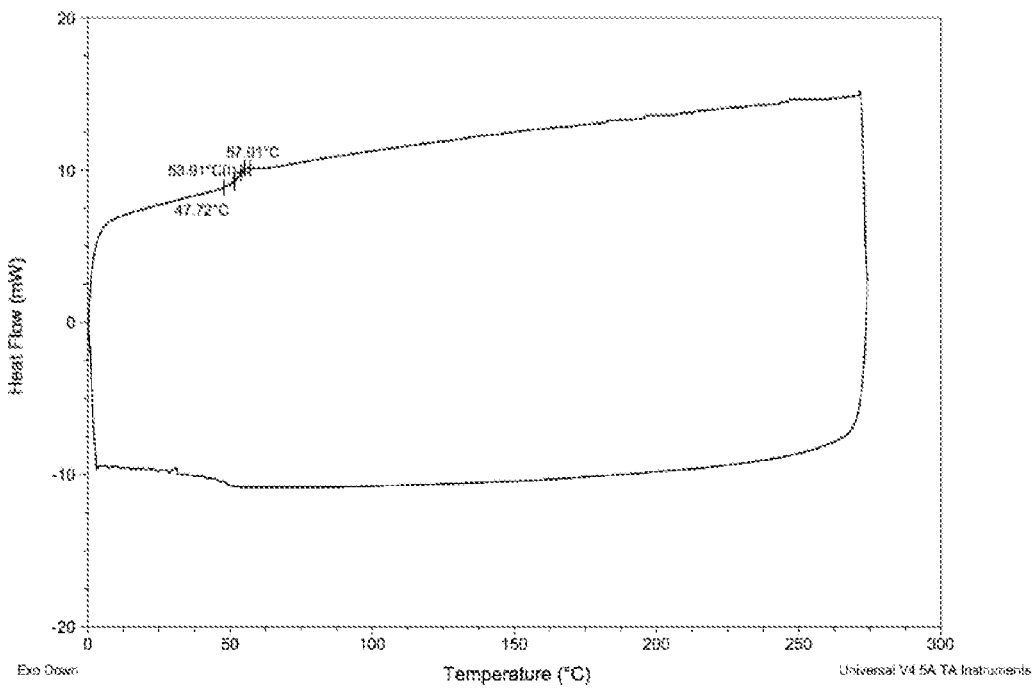
Figure 18C:
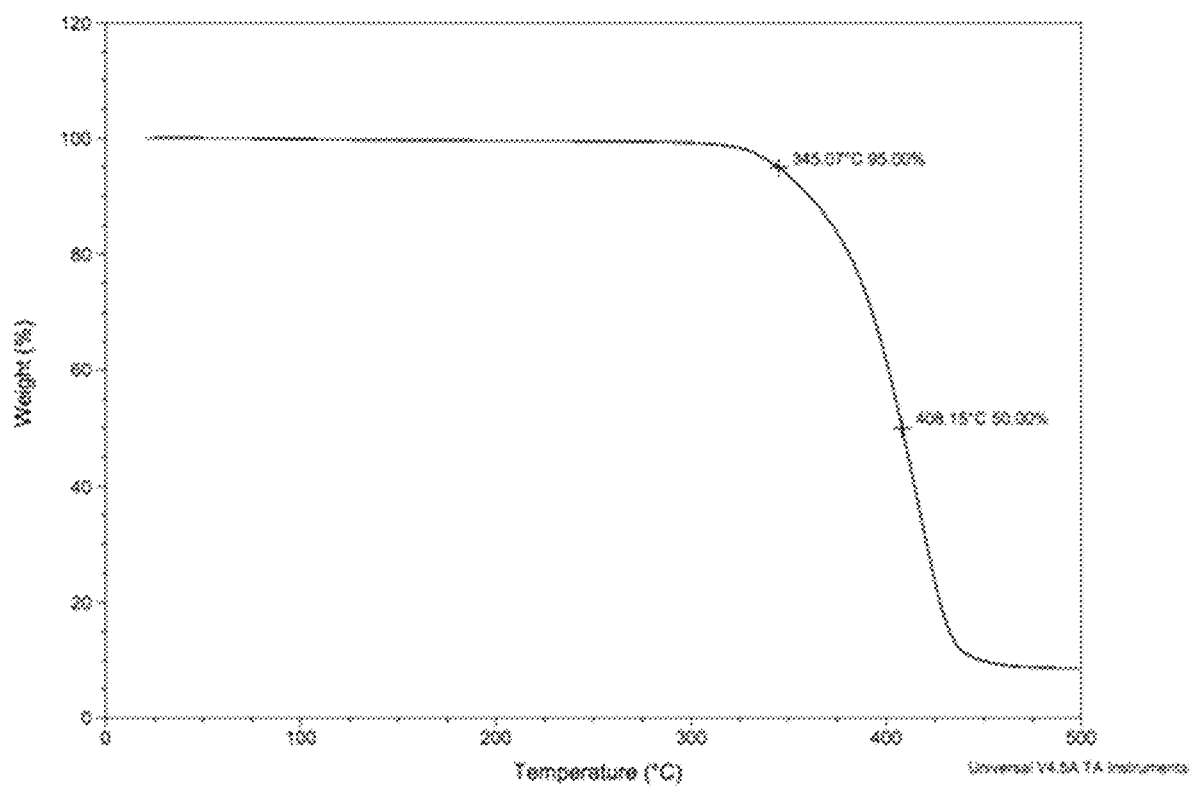
Figure 19A:
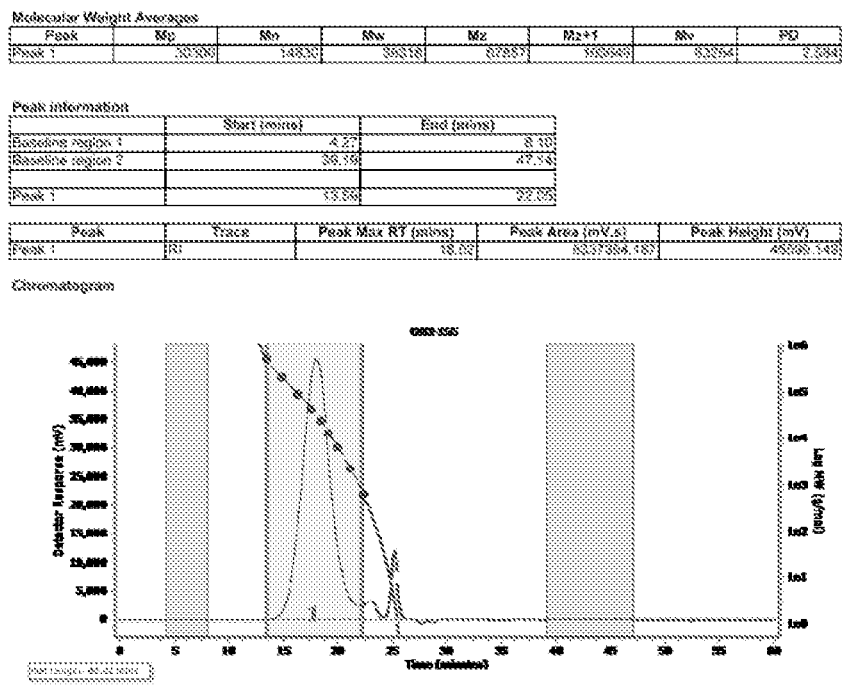
FIGS. 19A-E show characterization of poly(BHEC/BHET) with 40% BHEC.
Figure 19B:
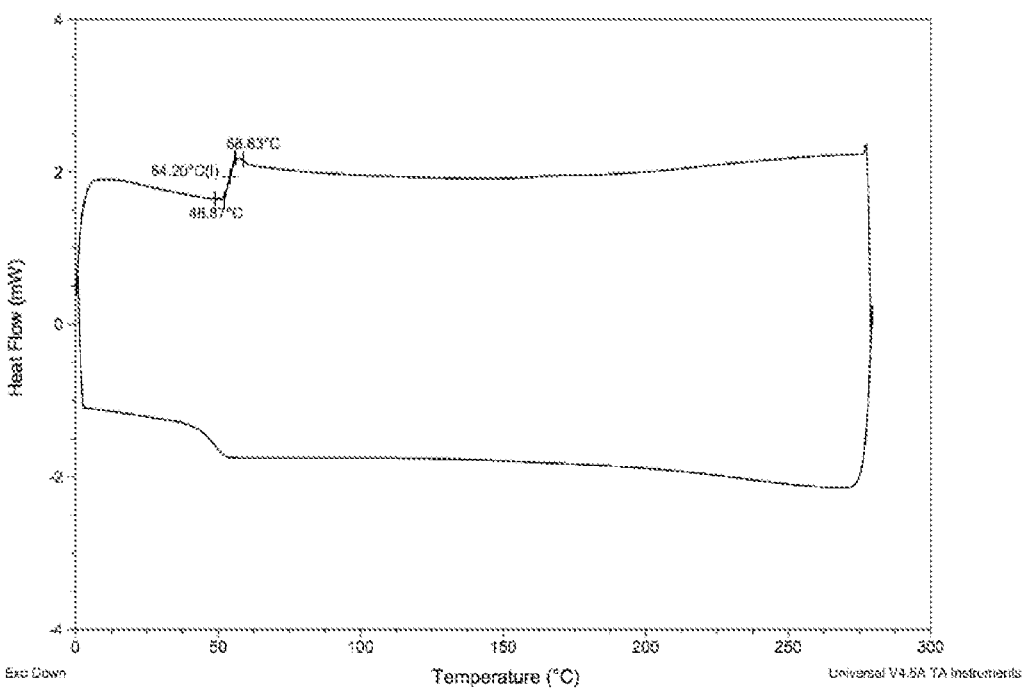
Figure 19C:
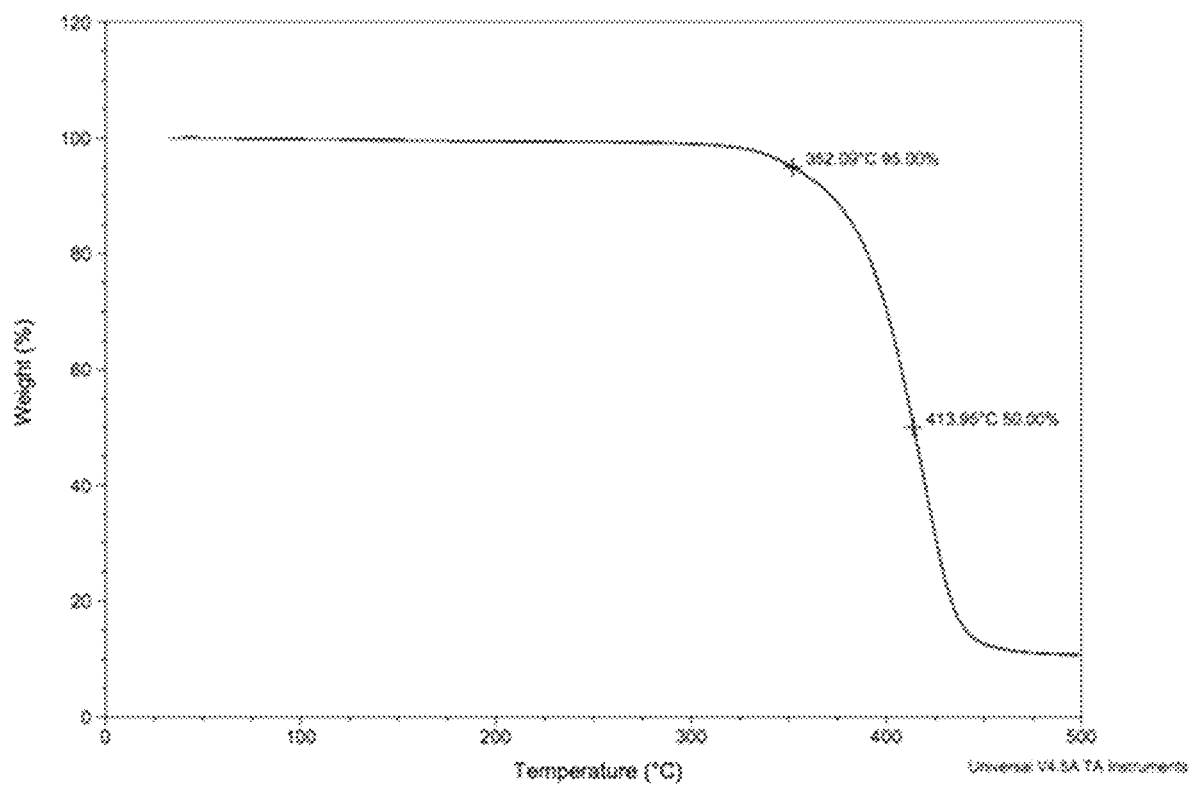
Figure 19D:
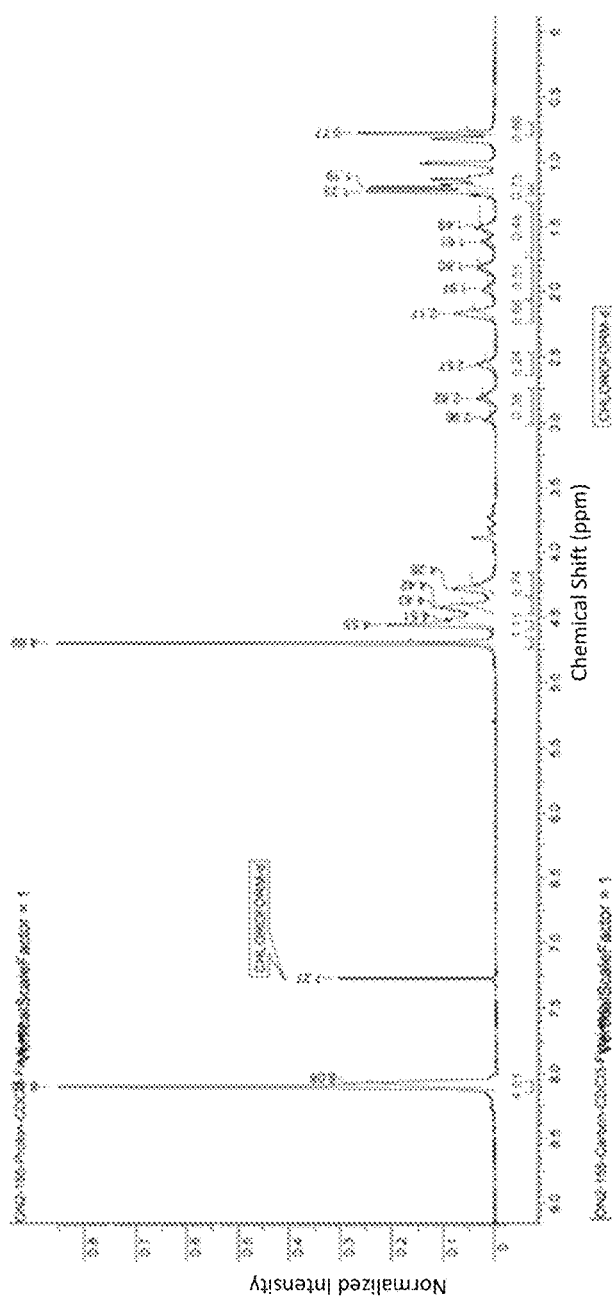
Figure 19E:
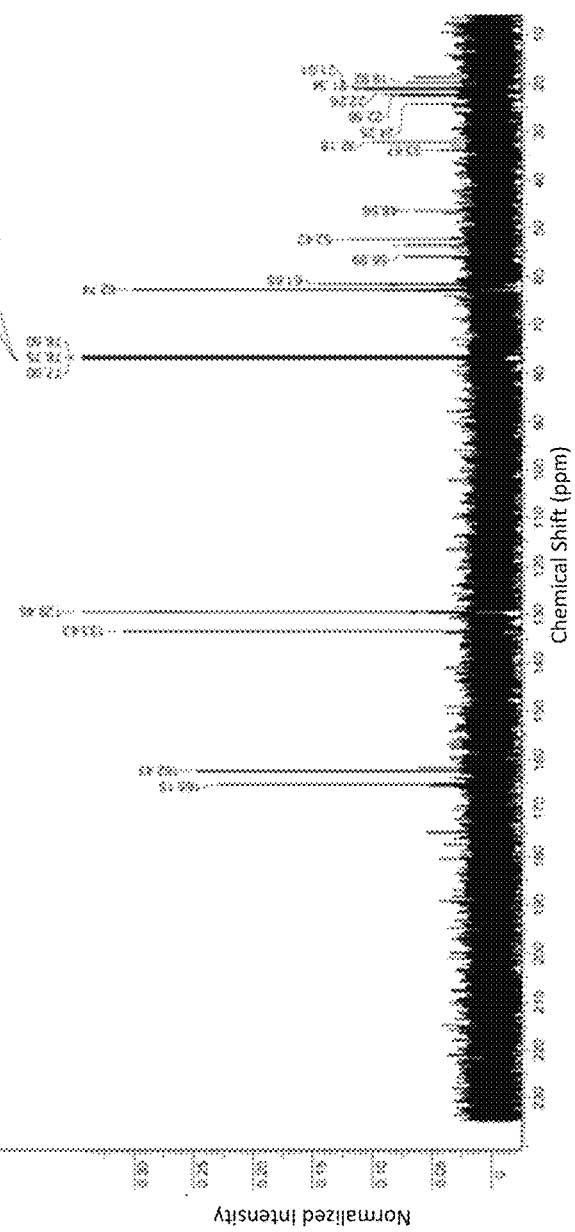
Figure 20A:
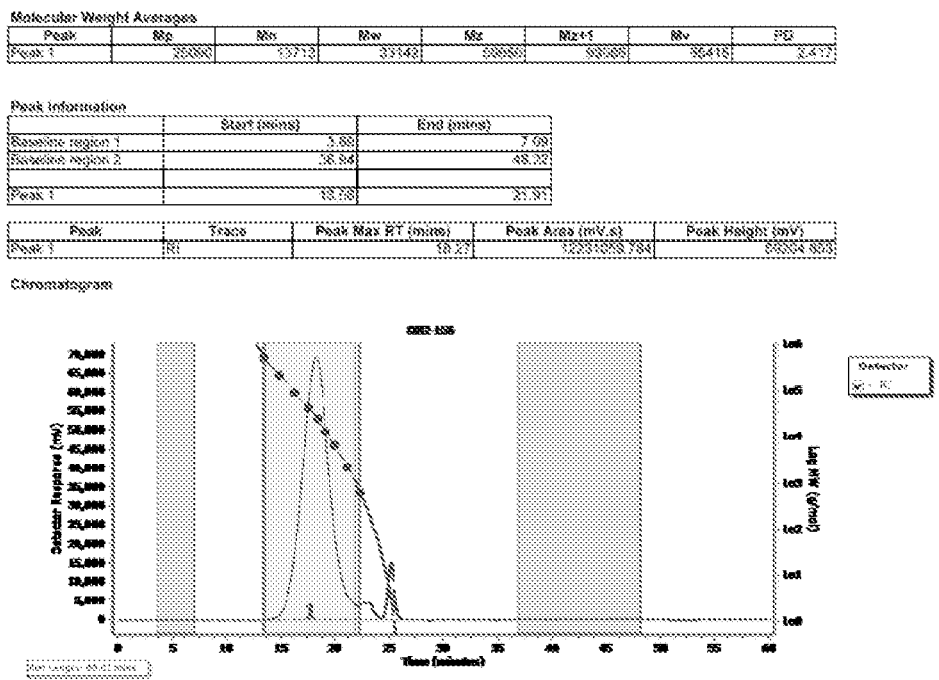
FIGS. 20A-E show characterization of poly(BHEC/BHET) with 30% BHEC.
Figure 20B:
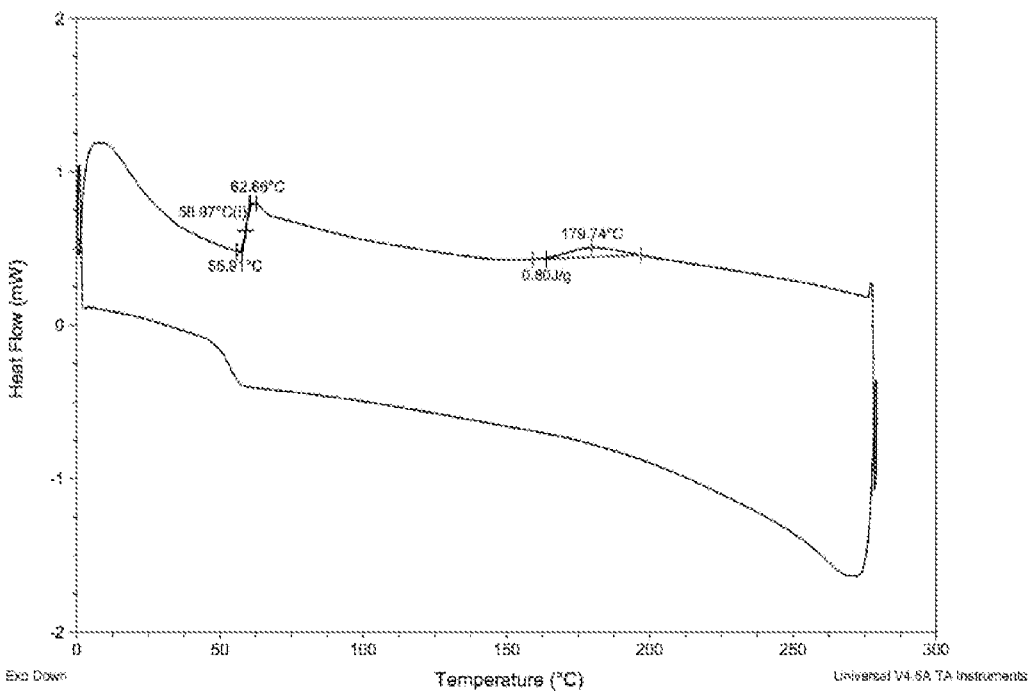
Figure 20C:
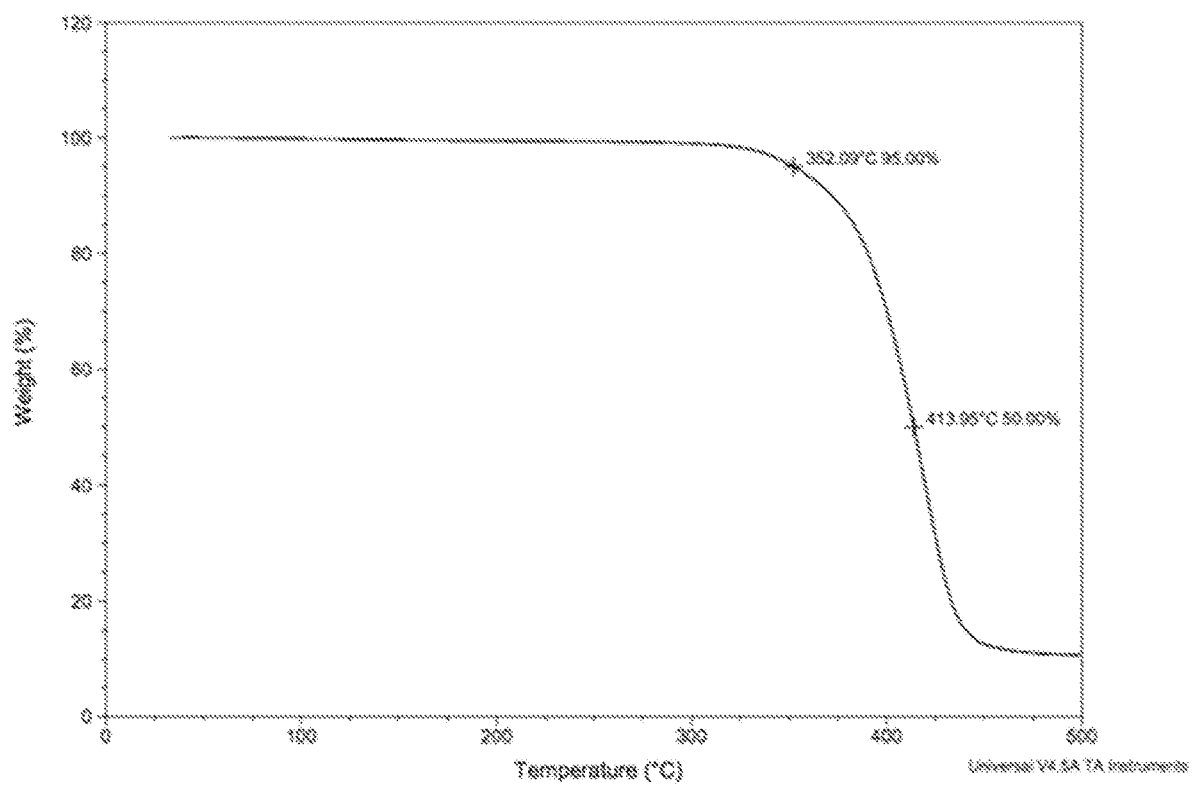
Figure 20D:
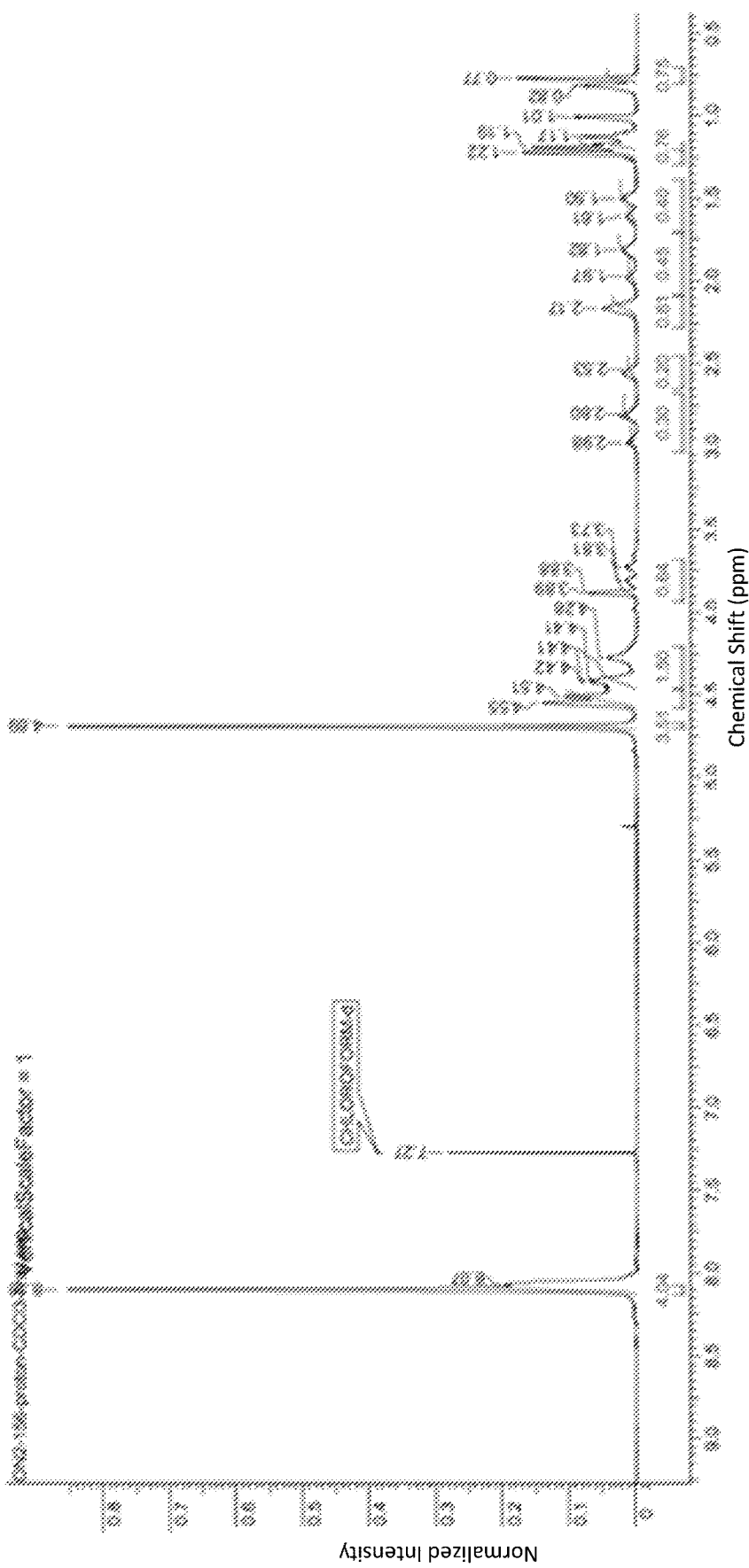
Figure 20E:
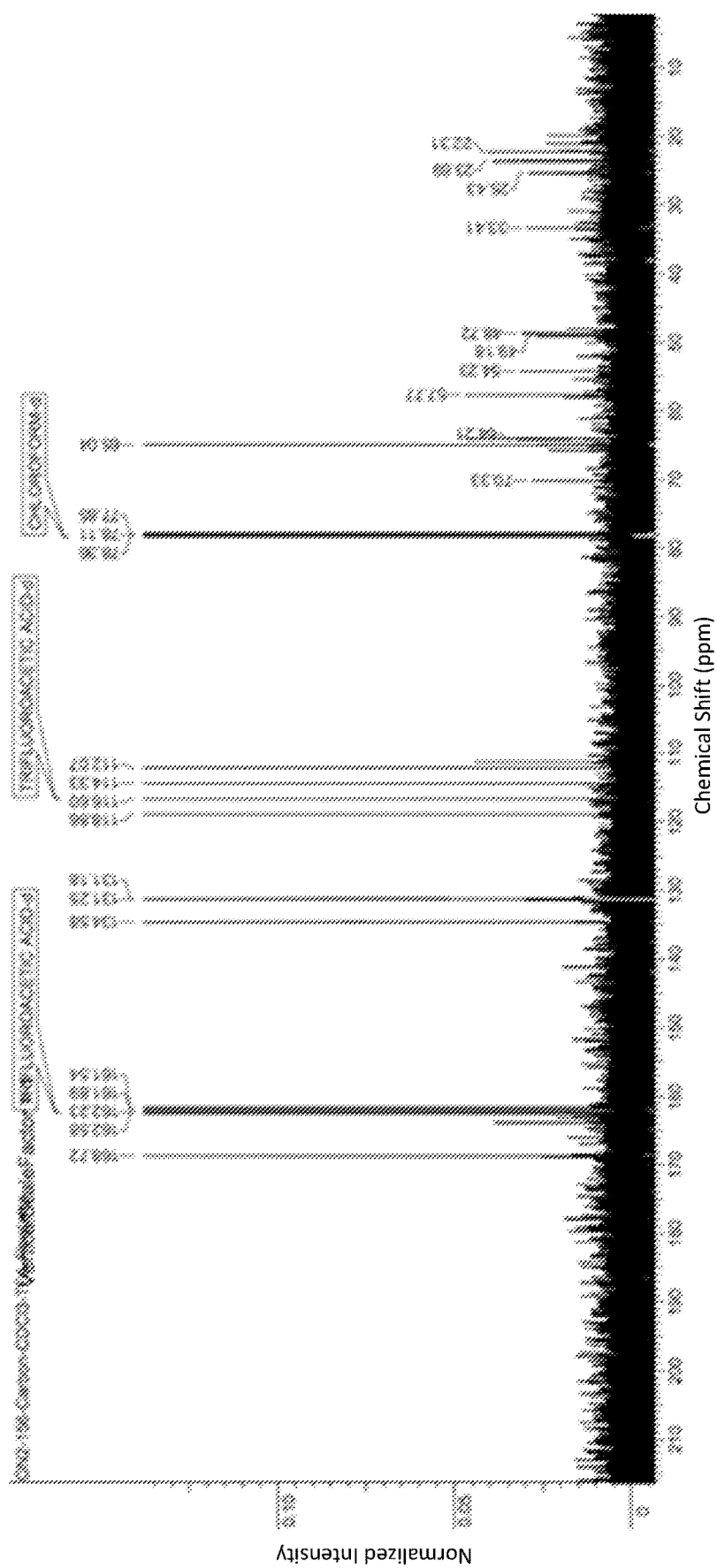
Figure 21A:
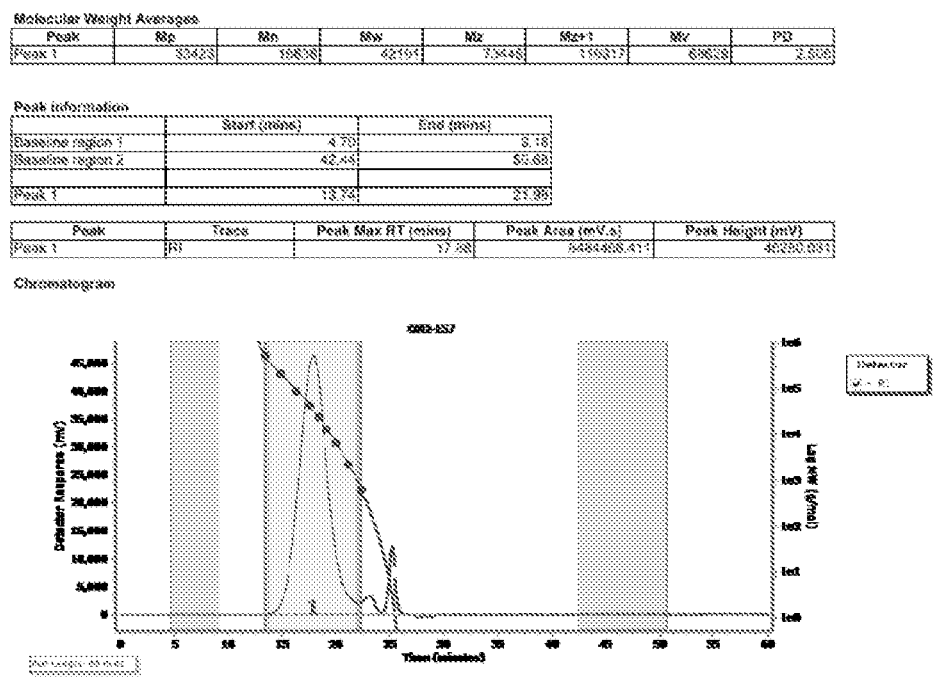
FIGS. 21A-E show characterization of poly(BHEC/BHET) with 20% BHEC.
Figure 21B:
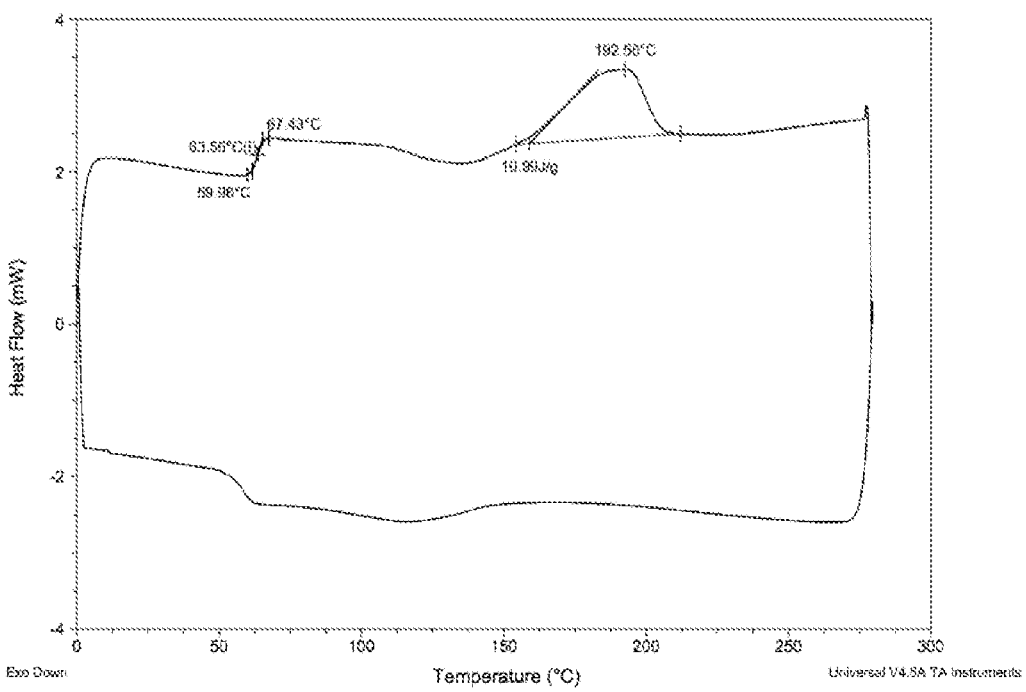
Figure 21C:
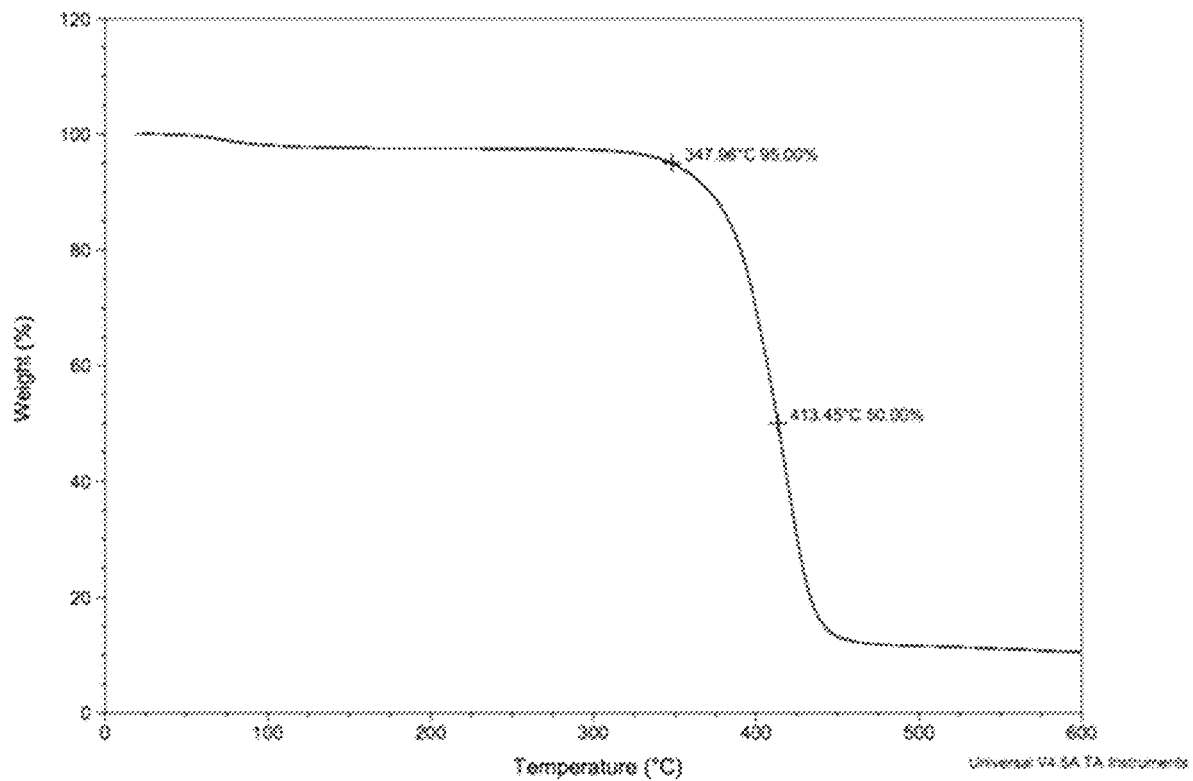
Figure 21D:
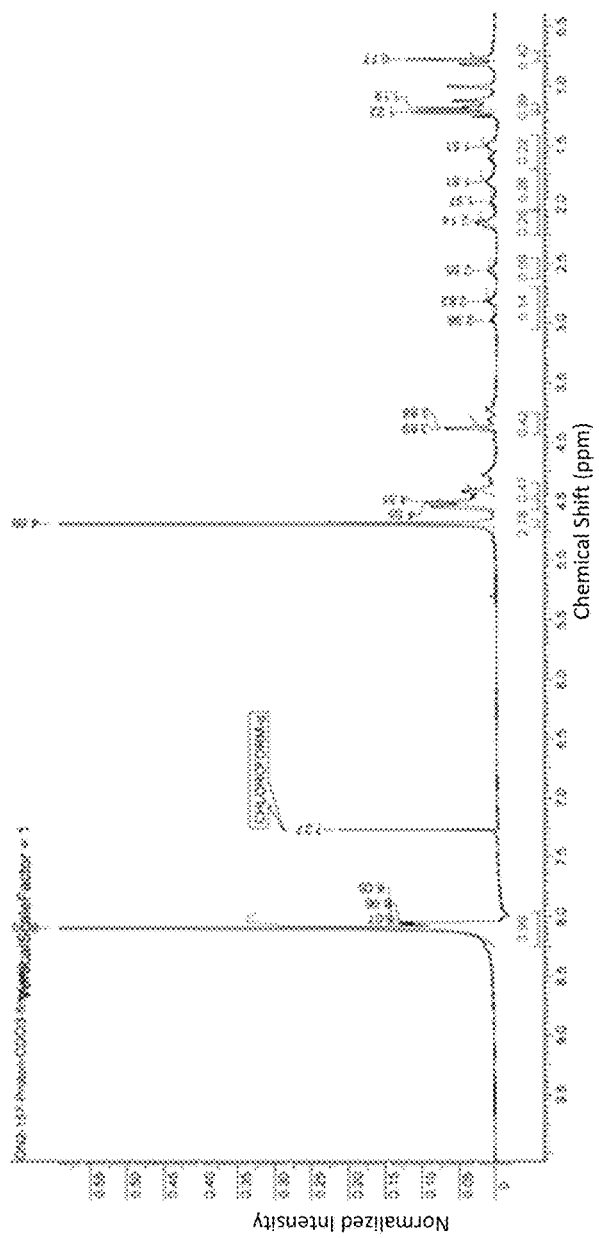
Figure 21E:
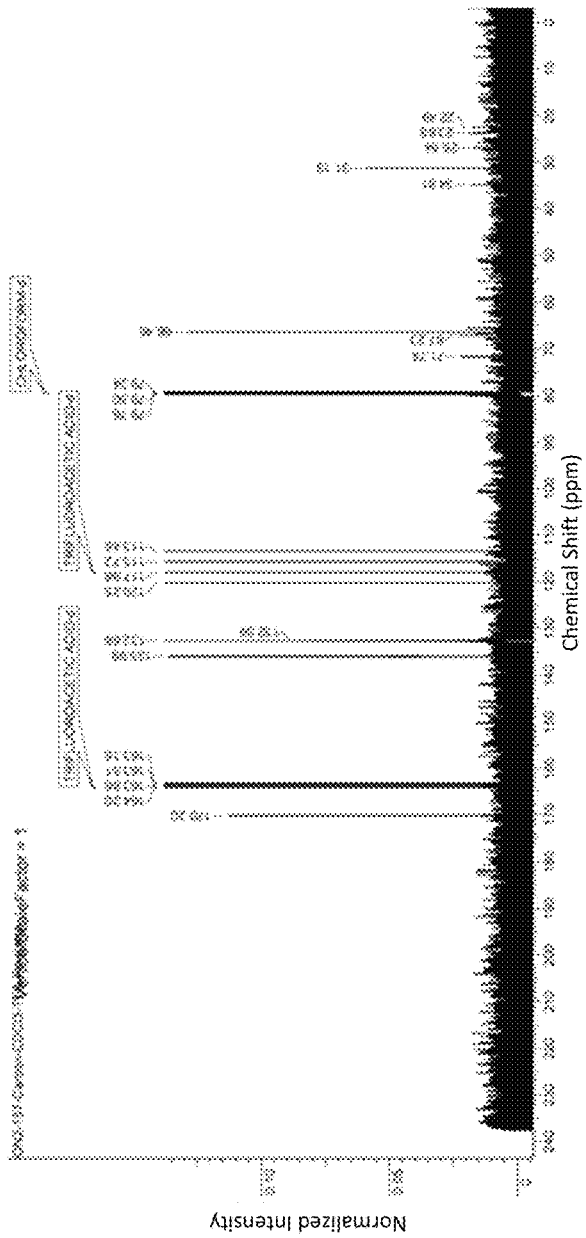
Figure 22A:
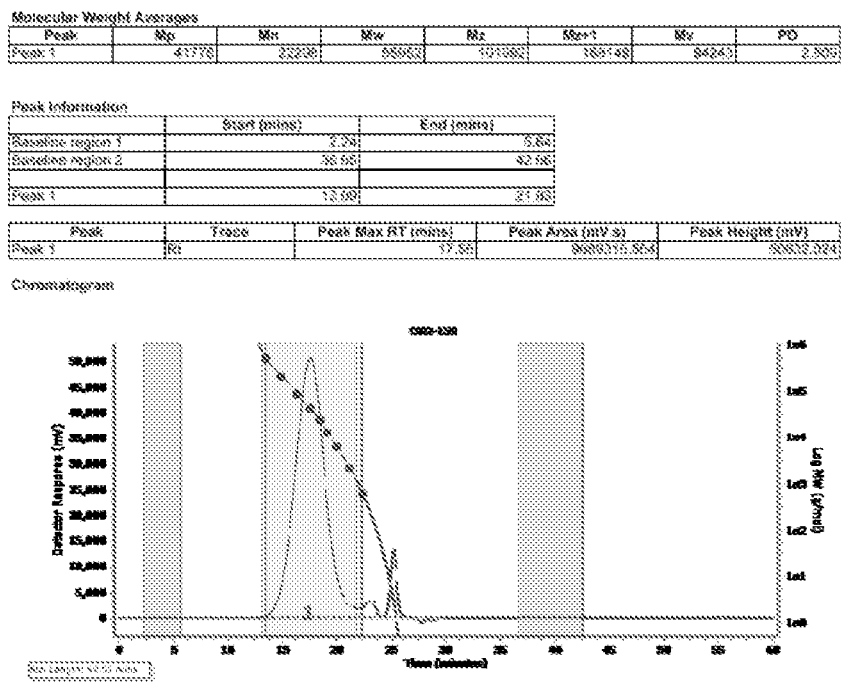
Figure 22B:
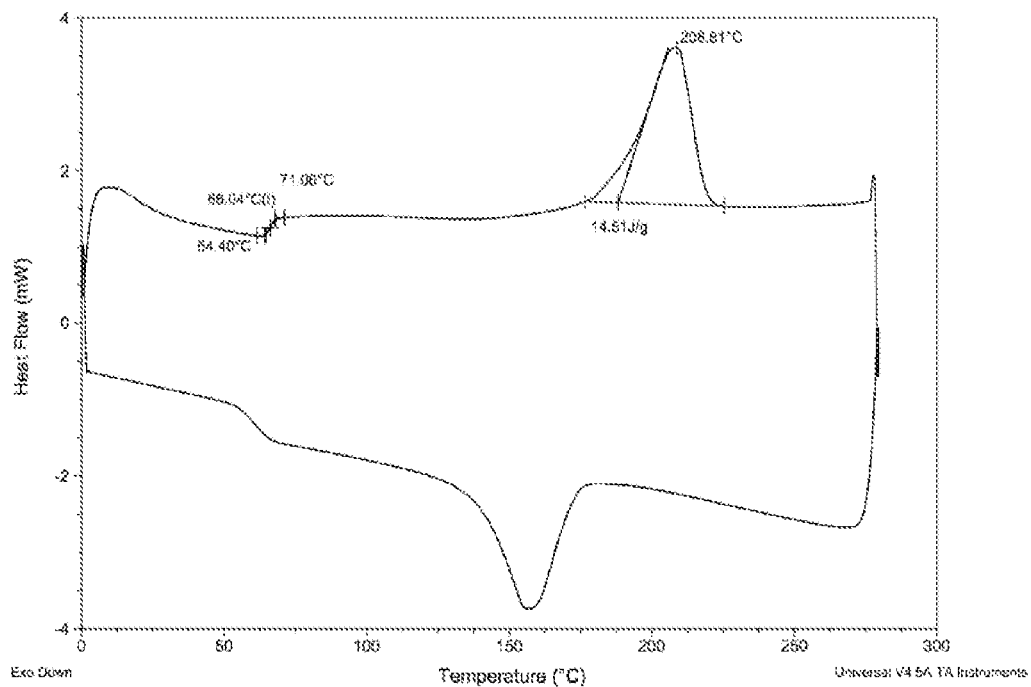
Figure 22C:
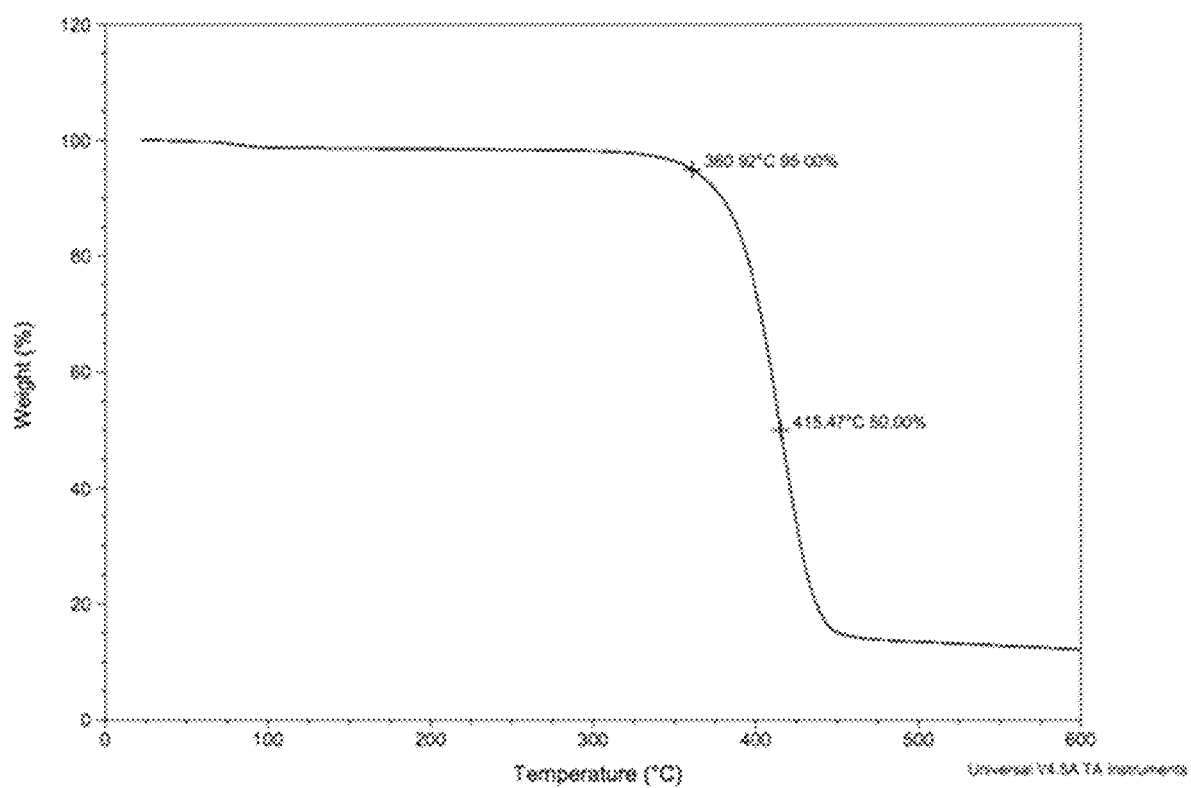
Figure 23A:
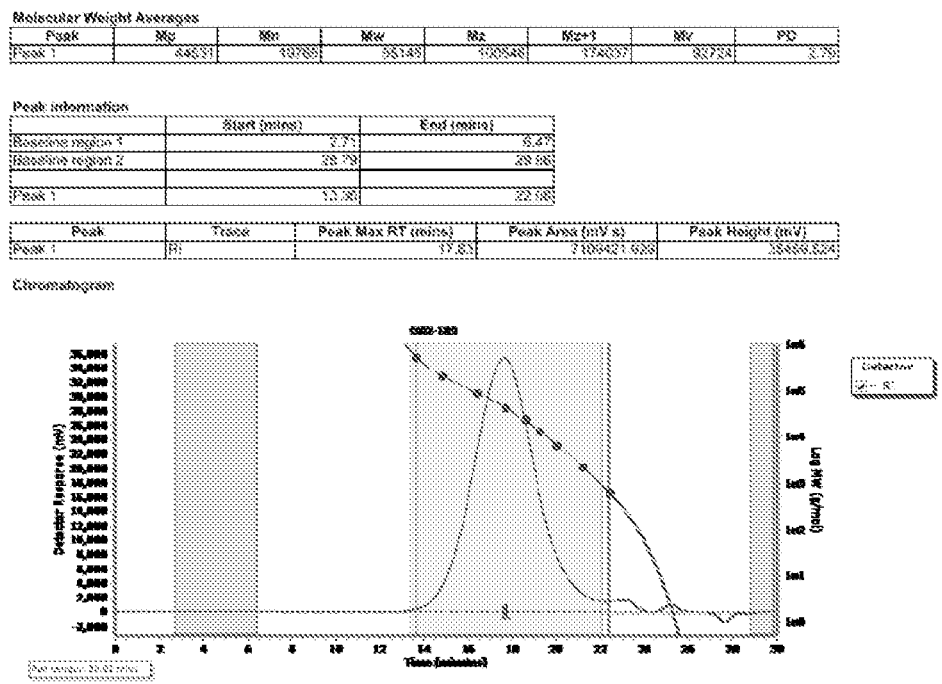
Figure 23B:
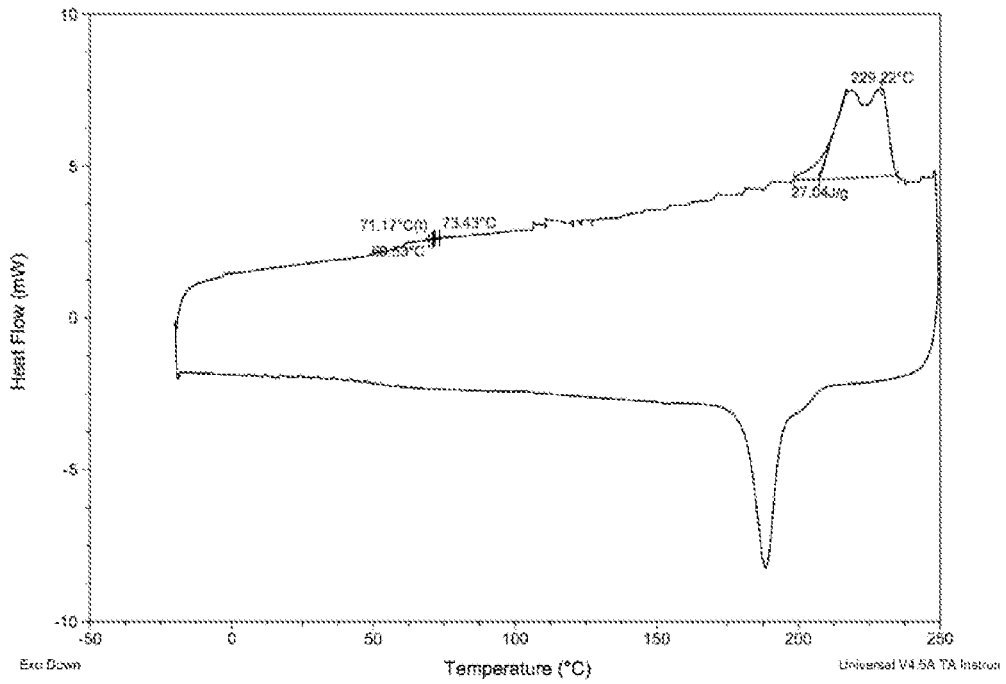
Figure 23C:
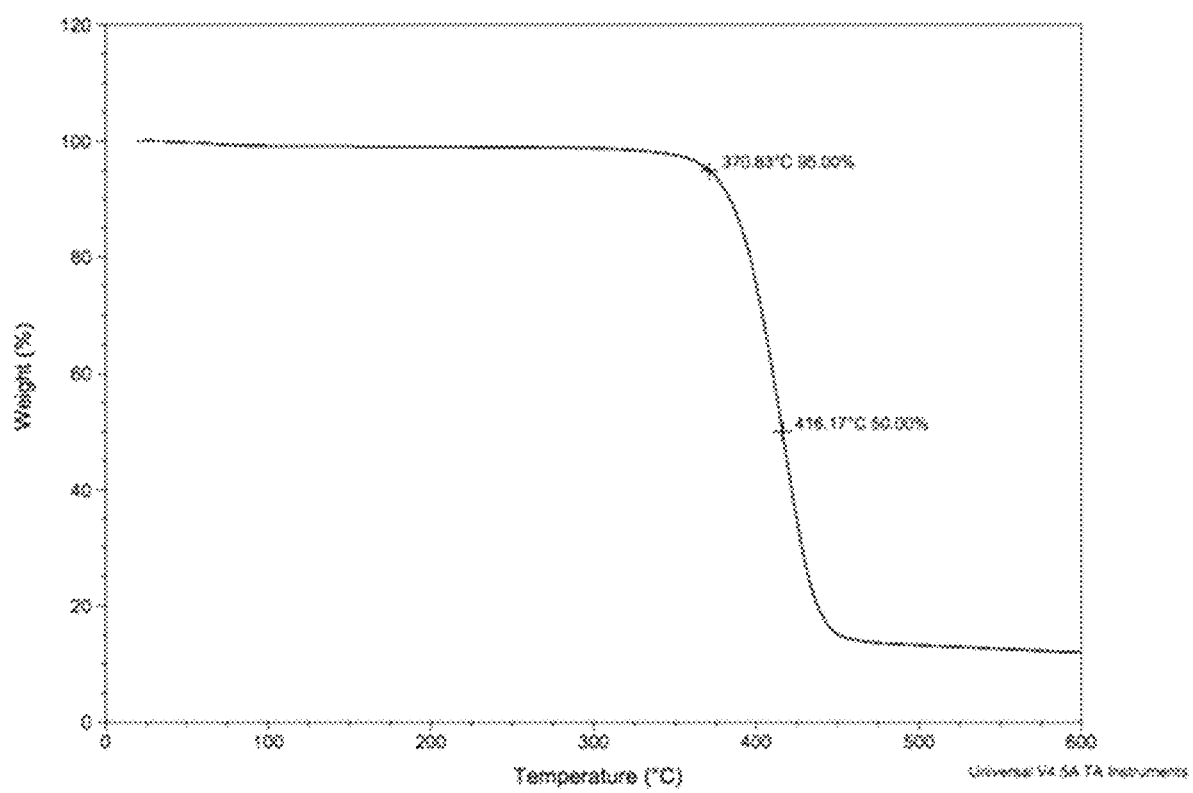

Suitably high molecular weight copolymers were obtained (Table 3) by the methods disclosed herein and shown in Scheme 2 (FIG. 4B), with Mn ranging between 13,300 and 23,800 Da and an average of about 17,900 Da. All but one of the dispersity values were found between 2.3 and 2.9. Copolymer $T_g$ values ranged between 41 and 71° C., with an observed trend that BHEC lowered the $T_g$ while BHET raised the $T_g$. Hence, BHEC incorporation increases the biobased content of the copolymer, but also lowers the $T_g$. Note the biobased content is about 25% (Table 3, Entry 6) when the copolymer has a $T_g$ competitive with that of PLA (54° C.). For this polymer, the biobased content would measure about 55% if the ethylene glycol were biosourced. When the BHET incorporation fraction was 80% or greater, then the materials exhibited crystallinity and a melting temperature in the range of 180 to 229° C. According to thermogravimetric analysis under nitrogen, the 5% decomposition temperatures (T5) were high, ranging from 335 to 371° C.

TABLE 3

| Entry | BHEC % Feed | BHEC % Incorporation [b] | Biobased Content (%) [c] | Yield (%) | $M_n$ (Da) [d] | $M_w$ (Da) [d] |
|---|---|---|---|---|---|---|
| 1 | 100 | 100.0 | 73.5 | 84 | 23,800 | 54,400 |
| 2 | 90 | 82.9 | 62.5 | 64 | 13,300 | 34,100 |
| 3 | 80 | 65.8 | 51.0 | 74 | 14,600 | 42,700 |
| 4 | 70 | 52.7 | 41.7 | 86 | 17,300 | 56,600 |
| 5 | 60 | 34.0 | 27.7 | 83 | 19,500 | 54,600 |
| 6 | 50 | 31.6 | 25.9 | 95 | 21,300 | 59,200 |
| 7 | 40 | 22.2 | 18.5 | 90 | 14,800 | 38,300 |
| 8 | 30 | 19.8 | 16.5 | 97 | 13,700 | 33,100 |
| 9 | 20 | 12.3 | 10.4 | 99 | 16,800 | 42,200 |
| 10 | 10 | 7.6 | 6.5 | 99 | 22,300 | 55,900 |
| 11 | 0 | 0.0 | 0.0 | 99 | 19,800 | 55,100 |

| Entry | Đ [d] | $T_g$ (° C.) [e] | $T_m$ (° C.) [e] | $T_5$ (° C.) [f] |
|---|---|---|---|---|
| 1 | 2.3 | 41 | n.o. | 343 |
| 2 | 2.6 | 42 | n.o. | 335 |
| 3 | 2.9 | 50 | n.o. | 344 |
| 4 | 3.3 | 46 | n.o. | 344 |
| 5 | 2.8 | 52 | n.o. | 342 |
| 6 | 2.7 | 54 | n.o. | 345 |
| 7 | 2.6 | 54 | n.o. | 351 |
| 8 | 2.4 | 59 | 180 | 352 |
| 9 | 2.5 | 64 | 193 | 348 |
| 10 | 2.5 | 66 | 207 | 361 |
| 11 | 2.8 | 71 | 229 | 371 |

[a] Polymerization conducted from 190 to 230° C. under dynamic vacuum with antimony oxide as a catalyst ($Sb_2O_3$, 1-2 mol %).
[b] BHEC and BHET % incorporation determined by $^1$H NMR by integrating the 1-methyl group of the camphoric acid ring (0.77 ppm) versus the aromatic protons (near 8.1 ppm).
[c] Calculated according to (166.22 × BHEC %) / [(226.27 × BHEC %) + (192.17 × BHET %)], where the numerical values represent the atoms contributed by camphoryl, oxyethyl camphoryl, and oxyethyl terephthaloyl, respectively.
[d] Gel Permeation Chromatography (GPC) in hexafluoroisopropanol (HFIP) at 40° C. vs polymethylmethacrylate standards.
[e] Determined by DSC; n.o. = not observed.
[f] Temperature at which 5% mass loss was observed under nitrogen, determined by TGA.

For the copolymers of Table 3, the BHEC incorporation percentage was determined by $^1$H NMR by integrating the 1-methyl group of the camphoric acid ring (near 0.77 ppm) versus the aromatic protons of the terephthalate ring (near 8.1 ppm). The integration values are given below in Table 4.

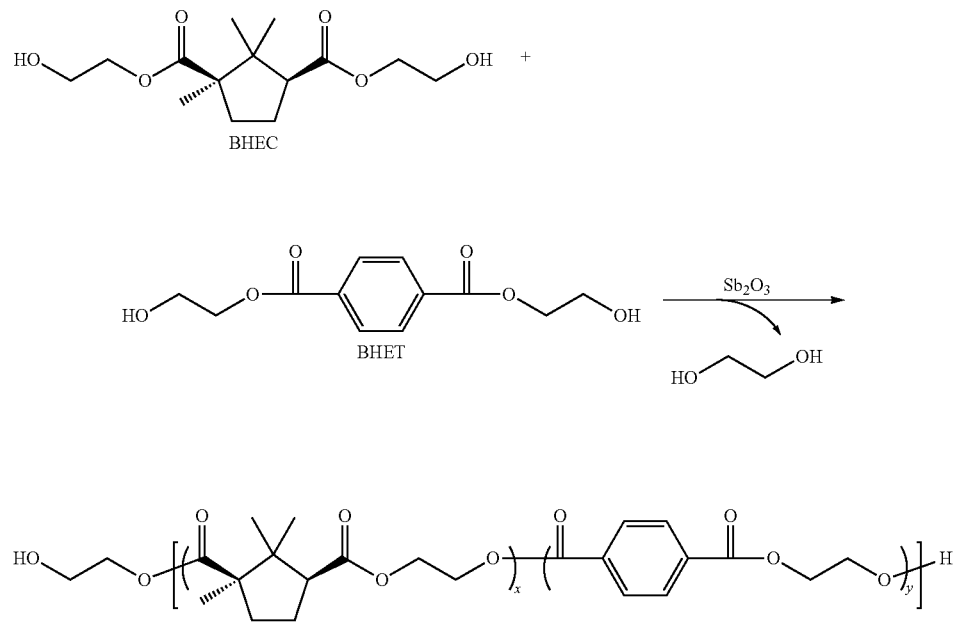

TABLE 4

| Entry | BHEC % Feed | BHEC methyl integration ($^1$H NMR) | BHET Ar-H integration ($^1$H NMR) | BHEC % Incorporation ($^1$H NMR) | BHET % Incorporation ($^1$H NMR) | BHEC % for $r_{BHEC} = 0.47$ $r_{BHET} = 2.26$ |
|---|---|---|---|---|---|---|
| 1 | 100 | 2.95 | 0.00 | 100.0 | 0.0 | 100.0 |
| 2 | 90 | 2.99 | 0.82 | 82.9 | 17.1 | 80.8 |
| 3 | 80 | 3.00 | 2.08 | 65.8 | 34.2 | 64.9 |
| 4 | 70 | 3.22 | 3.85 | 52.7 | 47.3 | 51.7 |
| 5 | 60 | 2.95 | 7.65 | 34.0 | 66.0 | 40.6 |
| 6 | 50 | 1.38 | 3.99 | 31.6 | 68.4 | 31.1 |
| 7 | 40 | 0.86 | 4.01 | 22.2 | 77.8 | 23.1 |
| 8 | 30 | 0.75 | 4.04 | 19.8 | 80.2 | 16.1 |
| 9 | 20 | 0.42 | 3.99 | 12.3 | 87.7 | 10.0 |
| 10 | 10 | 0.24 | 3.91 | 7.6 | 92.4 | 4.7 |
| 11 | 0 | 0.00 | 4.00 | 0.0 | 100.0 | 0.0 |

Since the methyl group bears 3 hydrogens and the aromatic phenylene component bears 4 hydrogens, the molar percent of BHEC in the copolymer is calculated according to $$BHEC\ \%\ \text{Incorporation} = \frac{[(BHEC\ \text{integration})/3]}{[(BHEC\ \text{integration})/3] + [(BHET\ \text{integration})/4]}$$

Figure 3:
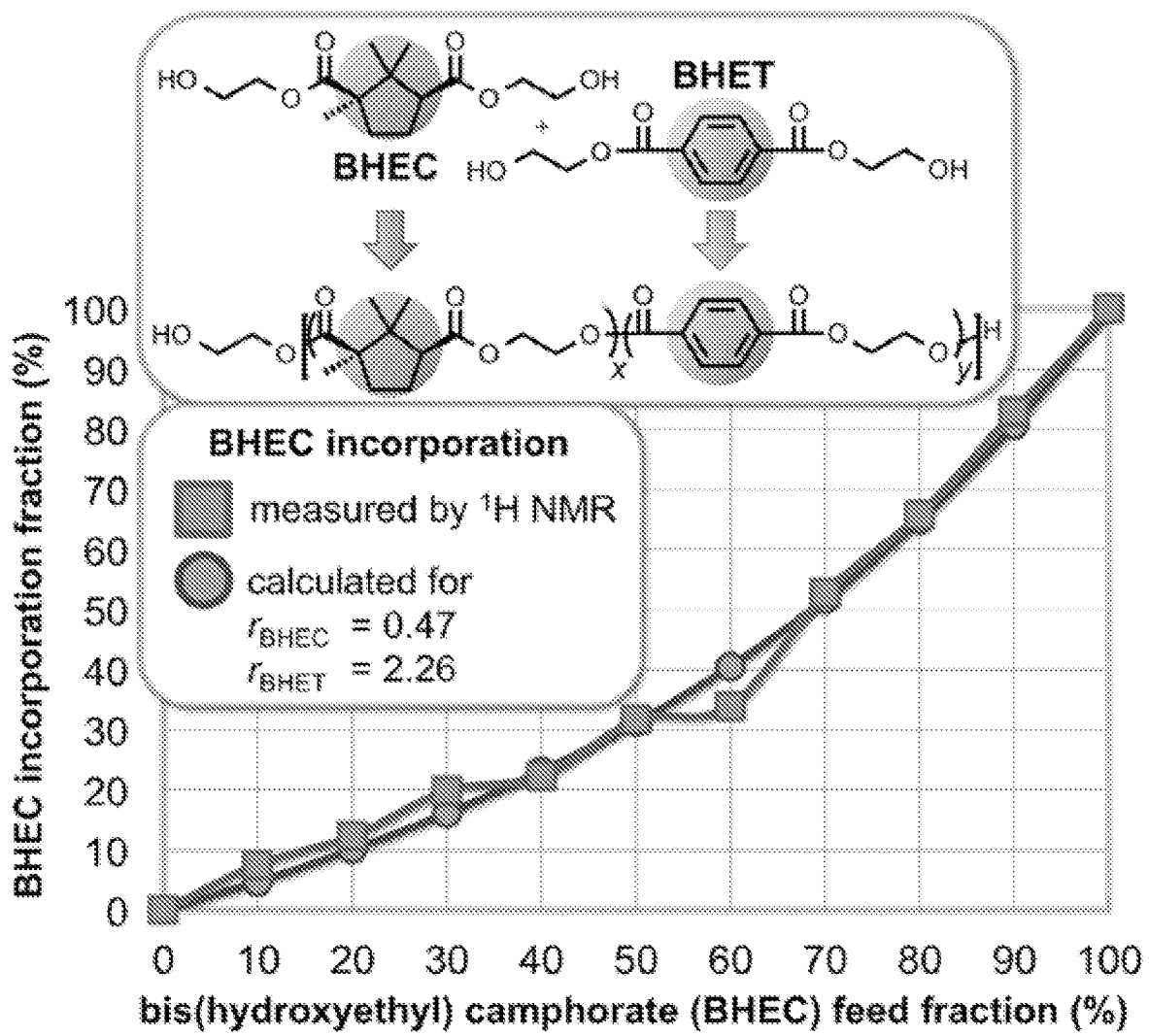
FIG. 3 shows representative data for the bis(hydroxyethyl)camphorate (BHEC) incorporation fraction versus the BHEC feed fraction. The data show that BHEC incorporation fraction is consistently lower than its feed fraction. Without wishing to be bound by a particular theory, it is possible that BHET is more easily incorporated into the disclosed formed polyethylene (camphorate/terephthalate) copolymers.

The reactivity ratios reported in FIG. 3 were calculated according to the copolymer molar composition equation usually applied to chain-growth copolymerization, but mathematically applicable to step-growth copolymerization as well:

$$F_C = \frac{r_C f_C^2 + f_C f_T}{r_C f_C^2 + 2 f_C f_T + r_T f_T^2}$$

where $r_C = r_{BHEC}$ = the reactivity ratio of bis(hydroxyethyl) camphorate, BHEC $r_T = r_{BHET}$ = the reactivity ratio of bis(hydroxyethyl) terephthalate, BHET $f_C$ = the feed fraction of bis(hydroxyethyl) camphorate, BHEC $f_T$ = the feed fraction of bis(hydroxyethyl) terephthalate, BHET $F_C = 1 - F_T$ = the composition fraction of bis(hydroxyethyl) camphorate, BHEC $F_T$ = the composition fraction of bis(hydroxyethyl) terephthalate, BHET Note in this copolymerization, $r_C = r_{BHEC} = k_{CC}/k_{CT}$ and $r_T = r_{BHET} = k_{TT}/k_{TC}$ However, the chain end for BHEC and BHET are nearly identical, with both ending in C(O)OCH$_2$CH$_2$OH. Thus, the following approximation applies:

$r_C = r_{BHEC} \sim k_C/k_T$ and $r_T = r_{BHET} \sim k_T/k_C$ where $k_C$ is the reaction rate constant of any chain end with BHEC and $k_T$ is the reaction rate constant of any chain end with BHET.

This suggests that $r_C$ and $r_T$ should bear a reciprocal relationship, which is essentially true:

$r_C = 0.47 \quad r_T = 2.26$ $1/0.47 = 2.12 \quad 1/2.26 = 0.44$

Figure 29A:
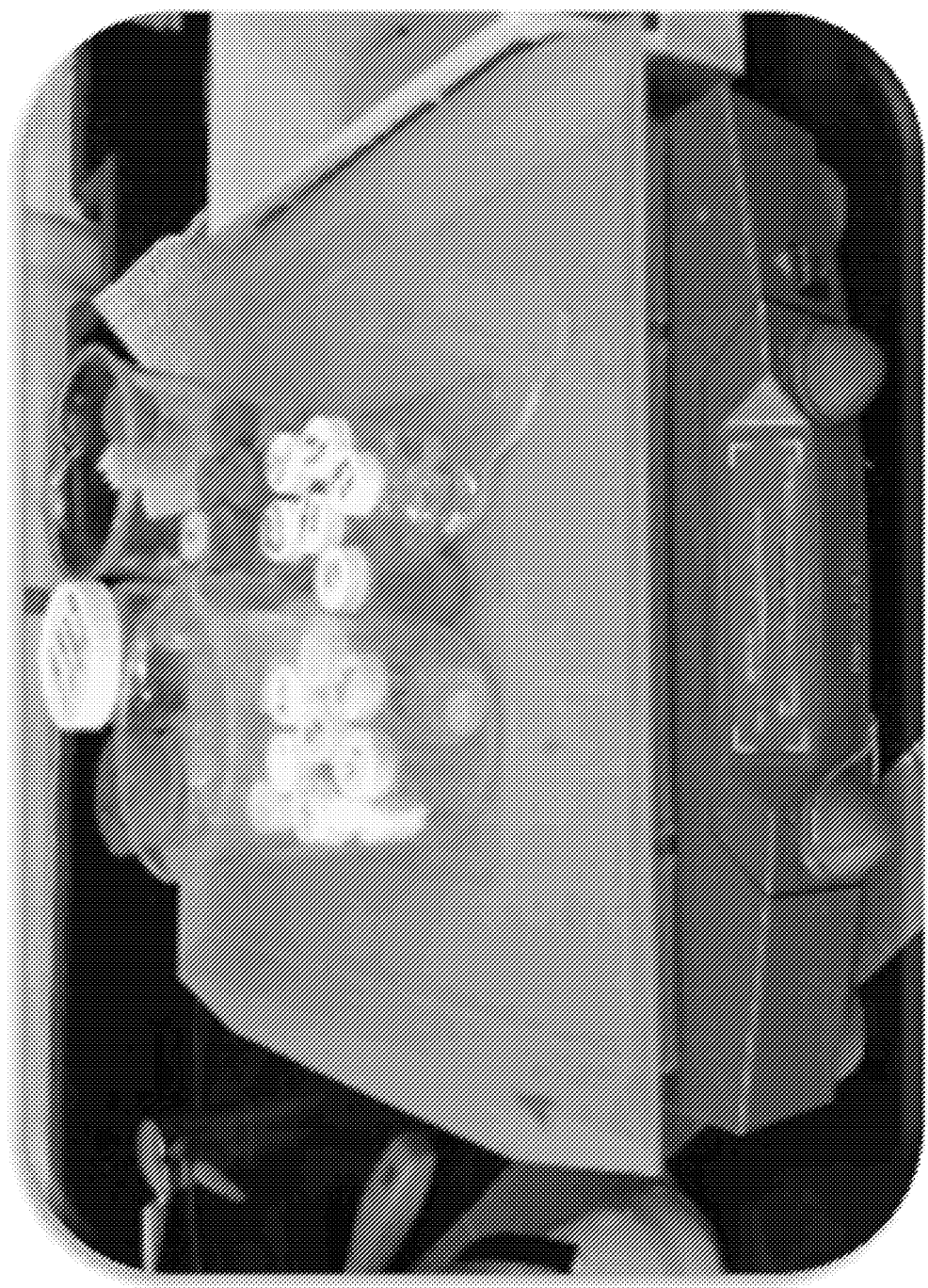
FIGS. 29A-C show gelation and degradation of polyethylene camphorate.
Figure 29B:
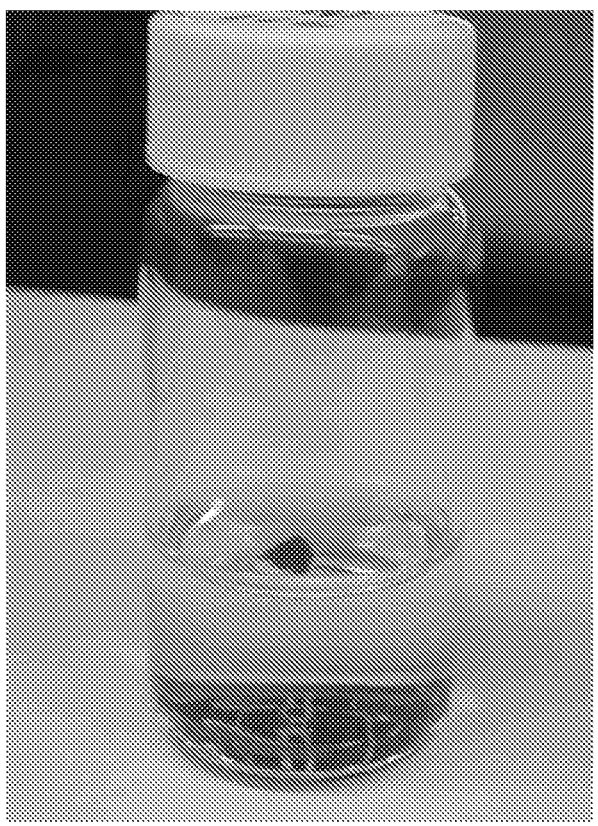
Figure 29C:
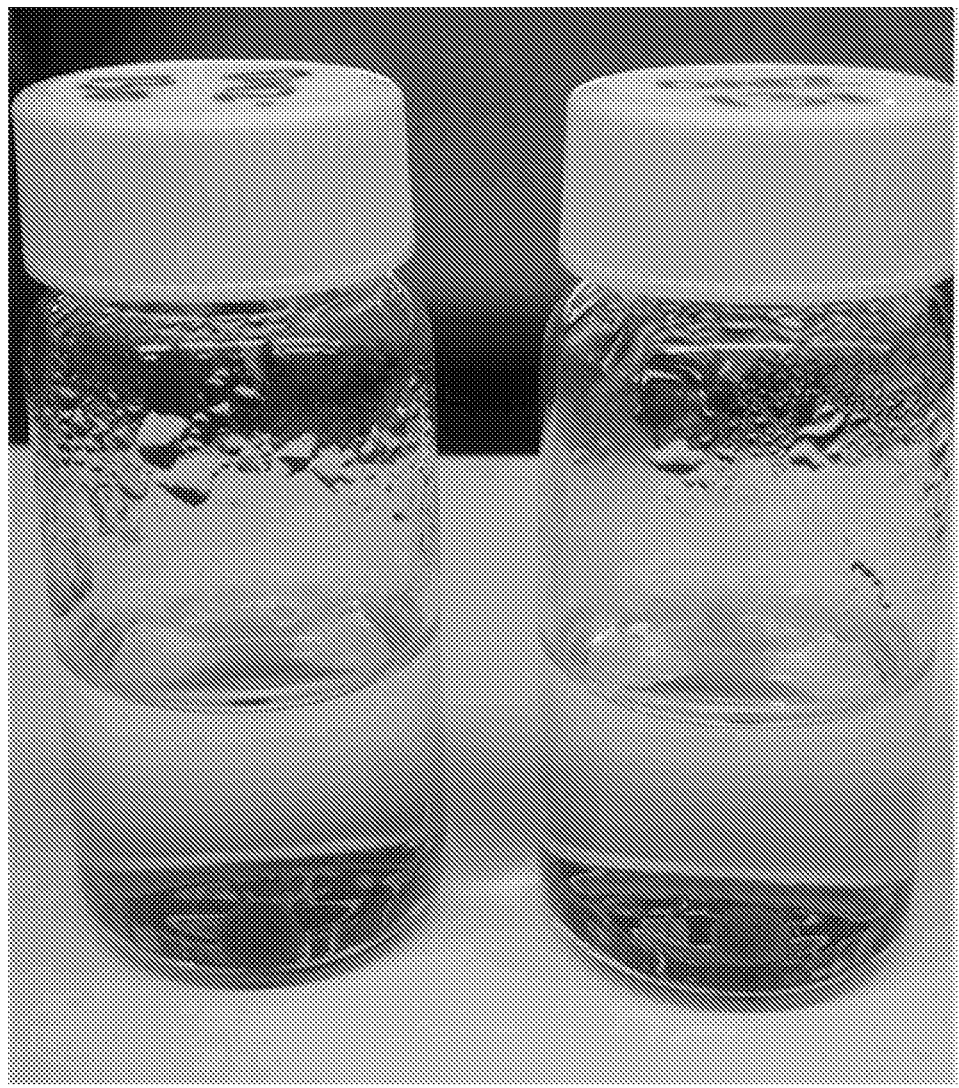
Figure 30A:
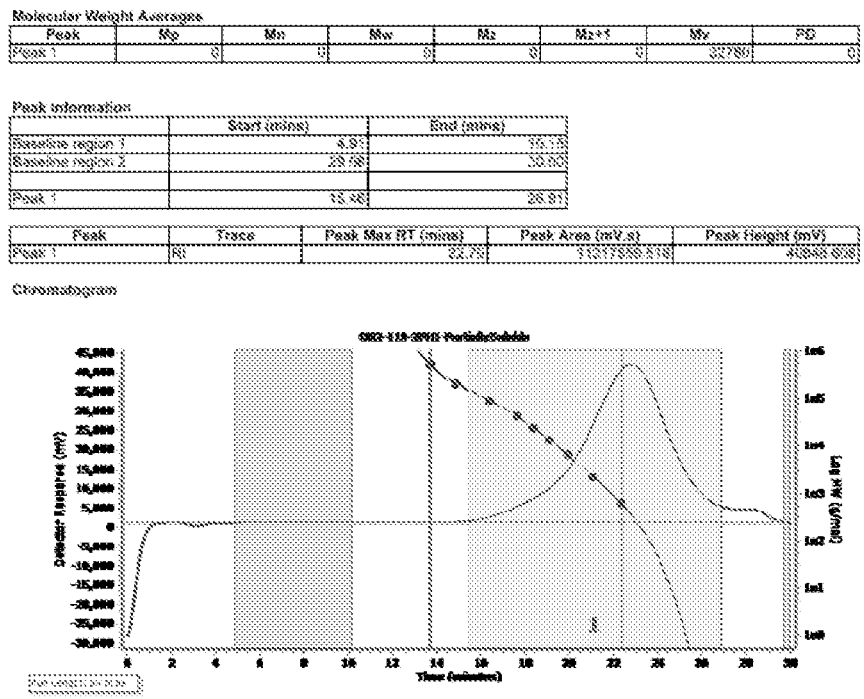
FIGS. 30A-B show gel permeation chromatograms for polyethylene camphorate in various pH conditions after 14 days.
Figure 30B:
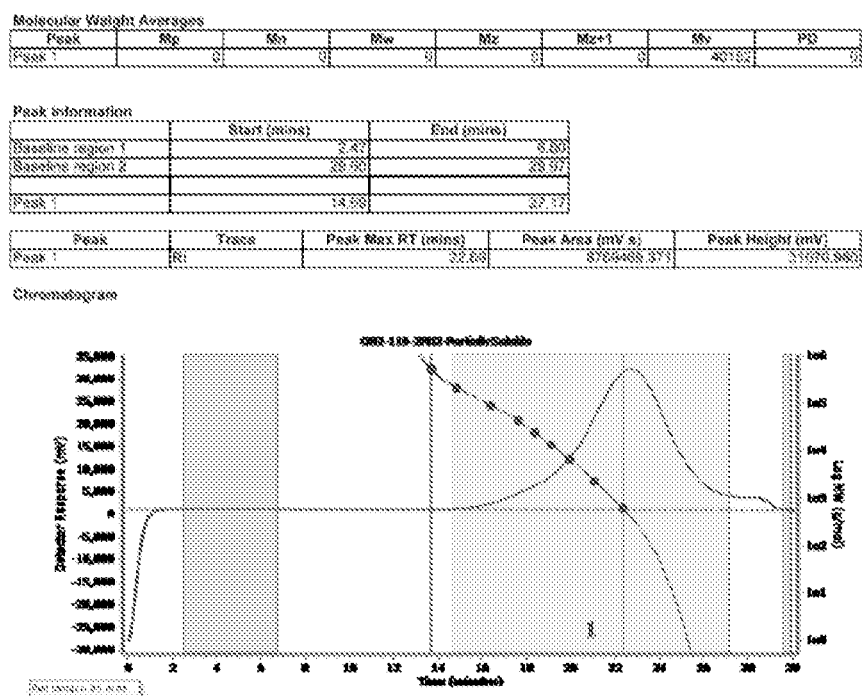
Figure 30C:
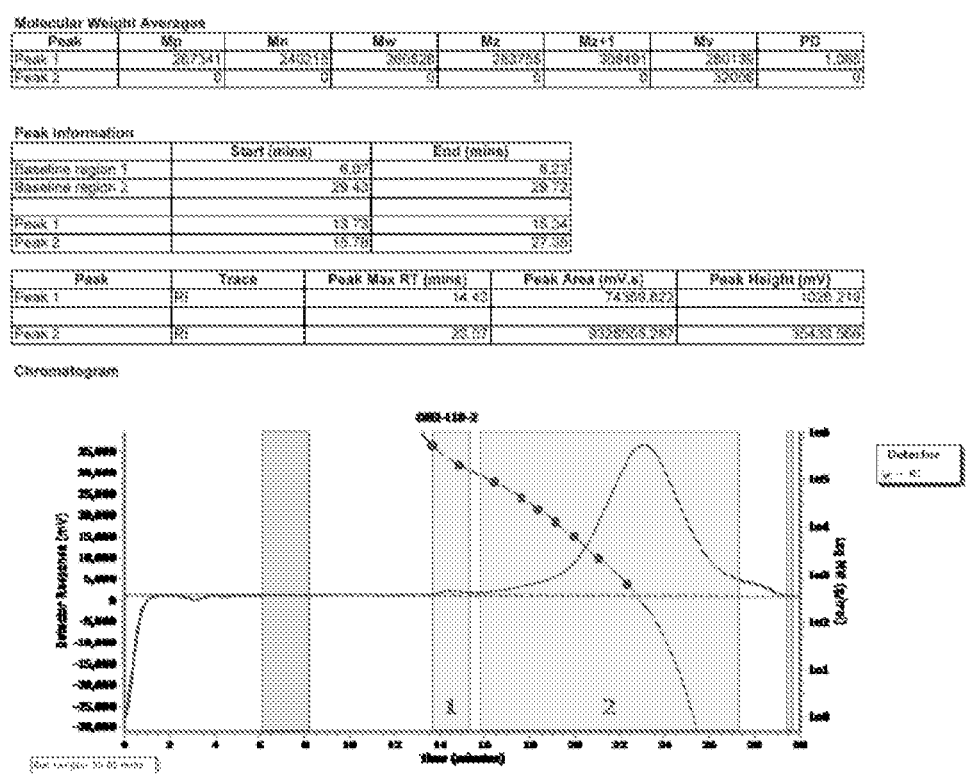
FIG. 30C shows polyethylene camphorate in aqueous solution (deionized water). The peak max (23.07 minutes) appears after the lowest molecular weight PMMA standard (22.4 minutes, 600 Da).

Polyethylene camphorate (PEC) with Mn=20,200 Da (Table 1, Entry 2) was subjected to heterogeneous degradation conditions on an orbital shaker at room temperature (FIGS. 29A-C): aqueous pH=1, aqueous pH=2, and deionized water with pH=7. After 14 days, GPC analysis of all three samples (FIGS. 30A-C) showed only a broad distribution of low molecular weight oligomers and monomers, with Mn<600 Da (the Mn of the lowest PMMA standard employed). Moreover, the physical appearance of the polymer changed significantly, transforming from an insoluble solid to a swollen gel. This is an important observation for PEC because it starkly contrasts the very slow hydrolysis observed with PLA, even at pH=1 over 45 days. Although polyglycolic acid is rather susceptible to hydrolytic degradation, more substituted polyesters generally resist hydrolysis. Preliminary computations suggest that camphorate esters possess a peculiar conformation with a sterically accessible carbonyl LUMO at the right ester as drawn in Table 1, Entry 2 (the less sterically hindered ester). Continuing studies will investigate the origins of this apparent sensitivity to hydrolysis (Scheme 1 shown in FIG. 4), along with characterization of the degradation products.

Novel polyesters were synthesized from biorenewable (+)-camphoric acid, derived from the abundantly available and inexpensive terpene (+)-camphor. As a diacid, camphoric acid was readily polymerized with a homologous series of linear diols or with cyclic diols. The observed glass transition temperature for polyethylene camphorate (PEC, $T_g$=51° C., from ethylene glycol) was comparable to that of polylactic acid (PLA, 55° C.), but the $T_g$ values decreased with increasing diol length. Cyclic diols erythritan and isosorbide, both derived from glucose, markedly increased the $T_g$ to 100 and 125° C., respectively. These are somewhat rare examples 9 of fully biobased polyesters possessing $T_g$ values surpassing that of polystyrene ($T_g$=95° C.). The polycondensation between camphoric acid and linear diols was catalyzed effectively with p-toluene sulfonic acid and proceeded without solvent, yielding the highest molecular weight for PEC (Mn=20,200). Camphoric acid was employed as an incremental replacement for the terephthalic acid of polyethylene terephthalate (PET). This copolymer was readily made via the solvent-free polymerization of bis(hydroxyethyl) camphorate (BHEC) with bis(hydroxyethyl) terephthalate (BHET), catalyzed by antimony oxide. Camphorate incorporation increased the biobased content of the resultant polymer, but also diminished the $T_g$ from that of PET itself; the $T_g$ dropped from 71 to 41° C. Preliminary degradation studies showed the unexpectedly facile degradation of PEC after 14 days of agitation in water at pH 1, 2, or 7 (see Table 5 below). The Mn dropped from 20,200 to <600 Da in all cases. The present disclosure and examples demonstrate that (+)-camphoric acid is a versatile monomer for synthesizing biobased polyesters with commercially attractive thermal properties and it will be a useful building block for constructing a variety of polymers with other architectures and functional groups, beyond the polyesters described herein.

standing of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A polyester copolymer having a structure represented by a formula:

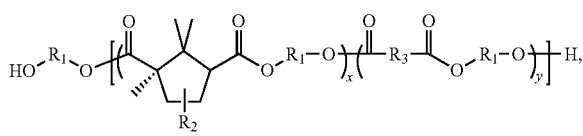

wherein $R_1$ is an erythritan group or an isosorbide group;
wherein each occurrence of $R_2$ is independently selected from hydrogen, C1-C12 alkanediyl, and C3-C12 cycloalkanediyl;
wherein $R_3$ is arylene, wherein the arylene has 6 to 14 carbon atoms; and

TABLE 5

| | | | | $M_n$ (Da) After 14 days | | |
|---|---|---|---|---|---|---|
| Entry | Polymer | Initial $M_n$ (Da) | $M_w$ (Da) | pH = 1 buffer | pH = 2 buffer | deionized water |
| 1 | | 20,200 | 60,800 | <600 | | |
| 2 | | 20,200 | 60,800 | | <600 | |
| 3 | | 20,200 | 60,800 | | | <600 |

[a] Gel permeation chromatography (GPC) in hexafluoroisopropanol (HFIP) at 40° C. vs polymethylmethacrylate standards.

It should be emphasized that the above-described embodiments of the present disclosure are merely possible examples of implementations set forth for a clear under-wherein x and y are not zero, wherein the polyester copolymer has a molecular weight Mw from about 5,000 Da to about 500,000 Da; and wherein the glass transition temperature of the polyester copolymer is at or above 100° C.

2. The polyester copolymer of claim 1, wherein $R_2$ is hydrogen.

* * * * *

UNITED STATES PATENT AND TRADEMARK OFFICE
CERTIFICATE OF CORRECTION

Page 1 of 1

PATENT NO. : 11,661,476 B2
APPLICATION NO. : 17/414173
DATED : May 30, 2023
INVENTOR(S) : Stephen A. Miller and Olivier Nsengiyumva It is certified that error appears in the above-identified patent and that said Letters Patent is hereby corrected as shown below:

In the Specification

At Column 1, delete Lines 8-22 and replace with:
--This application is the 35 U.S.C. § 371 national stage of PCT application having serial number PCT/US2020/018266, filed on Feb. 14, 2020. This application also claims priority to U.S. provisional application Nos. 62/805,875 and 62/953,695, respectively filed on Feb. 14, 2019 and Dec. 26, 2019, each of which is incorporated herein by reference in its entirety.

STATEMENT REGARDING FEDERALLY SPONSORED RESEARCH OR DEVELOPMENT This invention was made with U.S. Government support under grant number CHE-1607263, awarded by the National Science Foundation. The U.S. government has certain rights in the invention.--

Signed and Sealed this
Fifteenth Day of August, 2023

Katherine Kelly Vidal
*Director of the United States Patent and Trademark Office*